(12) United States Patent
Singh et al.

(10) Patent No.: US 9,040,527 B2
(45) Date of Patent: *May 26, 2015

(54) PYRIMIDINEDIAMINE KINASE INHIBITORS

(71) Applicant: Rigel Pharmaceuticals, Inc., South San Francisco, CA (US)

(72) Inventors: Rajinder Singh, Belmont, CA (US); Andy Atuegbu, Dublin, CA (US); John Ramphal, Union City, CA (US); Hui Li, Santa Clara, CA (US); Marina Gelman, San Francisco, CA (US); Jeffrey Clough, Redwood City, CA (US); Carlos Valdez, San Ramon, CA (US); Somasekhar Bhamidipati, Foster City, CA (US); Sambaiah Thota, Woburn, MA (US); Darren McMurtrie, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/948,342

(22) Filed: Jul. 23, 2013

(65) Prior Publication Data

US 2013/0309228 A1 Nov. 21, 2013

Related U.S. Application Data

(63) Continuation of application No. 13/610,569, filed on Sep. 11, 2012, now Pat. No. 8,518,937, which is a continuation of application No. 12/649,073, filed on Dec. 29, 2009, now Pat. No. 8,278,299.

(60) Provisional application No. 61/141,635, filed on Dec. 30, 2008.

(51) Int. Cl.
| | | |
|---|---|---|
| C07D 413/04 | (2006.01) | |
| C07D 498/04 | (2006.01) | |
| A61K 31/5415 | (2006.01) | |
| A61K 31/538 | (2006.01) | |
| C07D 413/14 | (2006.01) | |
| A61K 31/5383 | (2006.01) | |
| C07D 413/12 | (2006.01) | |
| C07D 417/12 | (2006.01) | |
| C07D 487/08 | (2006.01) | |
| A61K 45/06 | (2006.01) | |

(52) U.S. Cl.
CPC .......... *A61K 31/5383* (2013.01); *C07D 413/12* (2013.01); *C07D 413/14* (2013.01); *C07D 417/12* (2013.01); *C07D 487/08* (2013.01); *C07D 498/04* (2013.01); *A61K 45/06* (2013.01)

(58) Field of Classification Search
USPC ........................................ 514/230.5; 544/105
See application file for complete search history.

(56) References Cited

FOREIGN PATENT DOCUMENTS

| JP | A-2006-518386 | 8/2006 |
|---|---|---|
| WO | WO 03/032997 | 4/2003 |
| WO | WO 2004/014382 | 2/2004 |
| WO | WO 2004/074244 | 9/2004 |
| WO | WO 2005/012294 | 2/2005 |
| WO | WO 2005/013996 | 2/2005 |
| WO | WO 2005/016893 | 2/2005 |
| WO | WO 2006/021544 | 3/2006 |
| WO | WO 2010/078369 | 7/2010 |

OTHER PUBLICATIONS

Banker et al.., *Modern Pharmaceutics*, 3rd edition, pp. 451 and 596, Marcel Dekker, New York, New York, 1996.
Gavezzotti, "Are Crystal Structures Predictable?" *Accounts of Chemical Research* 27:309-314, 1994.
Vippagunta et al., "Crystalline Solids," *Advanced Drug Delivery Reviews* 48:3-26, 2001.
Wolff, *Burger's Medical Chemistry*, 5th edition, Part 1, pp. 975-977, John Wiley & Sons, 1995.

*Primary Examiner* — Kahsay Habte
(74) *Attorney, Agent, or Firm* — Travis Young; Klarquist Sparkman, LLP

(57) ABSTRACT

Disclosed embodiments provide pyrimidinediamine compounds useful for inhibiting kinase activity, including the activity of polo-like kinase 1 (PLK1). Also disclosed are pharmaceutical compositions comprising these compounds and methods of treating diseases associated with kinase activity, in particular enhanced PLK1 catalytic activity, such as diseases associated with abnormal cell proliferation, including neoplastic disorders.

11 Claims, No Drawings

PYRIMIDINEDIAMINE KINASE INHIBITORS

CROSS REFERENCE TO RELATED APPLICATIONS

This application is a continuation of U.S. patent application Ser. No. 13/610,569, filed on Sep. 11, 2012, which is a continuation of U.S. patent application Ser. No. 12/649,073, filed on Dec. 29, 2009, now issued as U.S. Pat. No. 8,278,299, which claims the benefit of the earlier filing date of U.S. Provisional Application Ser. No. 61/141,635, filed Dec. 30, 2008. These prior applications are incorporated herein by reference.

FIELD

The present invention relates generally to 2,4-pyrimidinediamine compounds that inhibit kinases, in particular polo-like kinase 1 (PLK1), pharmaceutical compositions which include the compounds, and methods of using the compounds and compositions for treatment of a variety of diseases and conditions associated with enhanced PLK1 activity, including hyperproliferative disorders.

BACKGROUND

Human polo-like kinase 1 (human PLK1) is a Serine/Threonine kinase, which belongs to a PLK family, named after a structurally similar polo kinase from *Drosophila melanogaster*. *Drosophila polo* mutants are defective in mitosis and have abnormal mitotic spindle poles. In mammals, four structurally homologous PLK proteins (PLK1, PLK2, PLK3, and PLK4) have been identified to date, all of them sharing a common architecture and having an N-terminal kinase catalytic domain and a C-terminal region containing either one (PLK4) or two (PLK1, PLK2, PLK3) polo-box domains. PLK1 is the most studied and best characterized member of the family. Specifically, PLK1 recapitulates most of the functions of polo kinase and is known to be a key regulator of mitosis in human cells.

PLK1 expression level and activity are strongly cell-cycle regulated, and peak around the time the cell enters into mitotic phase. Importantly, PLK1 transcripts are found only in proliferating tissues, while PLK2 (Serum-inducible kinase, SNK) and PLK3 (Proliferation-related, fibroblast growth factor inducible kinase, FNK) transcripts have broad tissue distribution, including post-mitotic neurons. PLK4/SAK is believed to function mostly in centriole biogenesis, and, like PLK1, is essential for cell viability.

PLK1 is essential for normal mitotic progression, and functions at multiple steps of mitosis. Specifically, PLK1 is necessary for entry into mitosis, for centrosomal maturation, mitotic spindle assembly and maintenance, exit from mitosis and for cytokinesis. At each of these steps PLK1 phosphorylates a distinct set of substrate proteins. Before entry into mitosis PLK1 phosphorylates and activates phosphatase cdc25c, which then translocates to the nucleus and, in turn, removes inhibitory phosphates from cyclin-dependent kinase CDK1. PLK1 also phosphorylates cyclin B1, the partner of CDK1. Together, activated CDK1/cyclin B complex initiates entry of the cell into mitosis.

PLK1 overexpression is believed to be strongly associated with neoplastic cells. Specifically, it has been shown that PLK1 RNA is expressed at high levels in lung and breast tumors, with little to no expression in adjacent normal tissue. Further, PLK1 overexpression was found to correlate with histological grade, and poor prognosis in several types of cancer, such as ovarian and endometrial cancers, esophageal carcinomas and non-small cell lung carcinomas.

Downregulation of PLK1 in tumor cells induces mitotic arrest and subsequent cell death. Therefore what is needed are compounds and compositions that inhibit PLK1 for use in treatment of disease states where the PLK1 pathway is involved.

SUMMARY

Aspects of the present disclosure relate to pyrimidinediamine compounds which are useful as kinase inhibitors. In particular, representative compounds include PLK1 inhibitors Also disclosed herein are methods for using these compounds in treating diseases and conditions associated with a kinase activity and in particular, enhanced PLK1 activity, such as hyperproliferative disorders, including neoplasms, and pharmaceutical compositions which include these compounds.

In one aspect, provided herein is a compound according to Formula I:

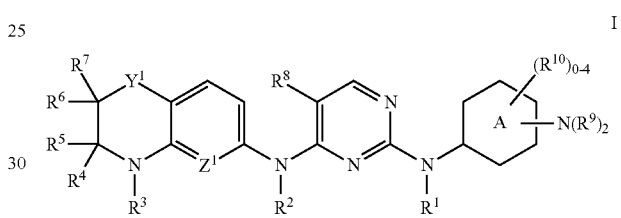

or a pharmaceutically acceptable salt, a solvate, an N-oxide, or a prodrug thereof, wherein:

$Y^1$ is O or S;

$Z^1$ is CH or N;

A is an aromatic ring;

$R^1$ is H;

$R^2$ and $R^3$ are each, independently of one another, H, (C1-C6) alkyl optionally substituted with one or more of the same or different $R^{11}$ groups, (C3-C8) cycloalkyl optionally substituted with one or more of the same or different $R^{11}$ groups, (C4-C11) cycloalkylalkyl optionally substituted with one or more of the same or different $R^{11}$ groups, (C5-C10) aryl optionally substituted with one or more of the same or different $R^{11}$ groups, (C6-C16) arylalkyl optionally substituted with one or more of the same or different $R^{11}$ groups, 2-6 membered heteroalkyl optionally substituted with one or more of the same or different $R^{11}$ groups, 3-8 membered cycloheteroalkyl, optionally substituted with one or more of the same or different $R^{11}$ groups, 4-11 membered cycloheteroalkylalkyl, optionally substituted with one or more of the same or different $R^{11}$ groups, 5-10 membered heteroaryl optionally substituted with one or more of the same or different $R^{11}$ groups or 6-16 membered heteroarylalkyl optionally substituted with one or more of the same or different $R^{11}$ groups;

In one embodiment, $R^2$, $R^3$, or both independently are phosphate ester progroups. Examples of such progroups have the formula $-(CR^dR^d)_y-O-P(O)(OH)(OR^e)$ or $-(CR^dR^d)_y-O-P(O)(OR^e)(OR^e)$, or a salt thereof, wherein each $R^e$ is, independently of the others, selected from substituted or unsubstituted lower alkyl, substituted or unsubstituted (C6-C14) aryl (e.g., phenyl, naphthyl, 4-loweralkoxyphenyl, 4-methoxyphenyl), substituted or unsubstituted (C7-C20) arylalkyl (e.g., benzyl, 1-phenylethan-1-yl, 2-phenylethan-1-yl), —(CR$^d$R$^d$)$_y$—OR$^f$, —(CR$^d$R$^d$)$_y$—O—C(O)R$^f$, —(CR$^d$R$^d$)$_y$—O—C(O)OR$^f$, —(CR$^d$R$^d$)$_y$—S—C(O)R$^f$, —(CR$^d$R$^d$)$_y$—S—C(O)OR$^f$, —(CR$^d$R$^d$)$_y$—NH—C(O)R$^f$, —(CR$^d$R$^d$)$_y$—NH—C(O)OR$^f$ and —Si(R$^d$)$_3$, wherein R$^d$, R$^f$ and y are as defined above. In a specific embodiment, each R$^d$ is selected from hydrogen and unsubstituted lower alkyl and/or each R$^e$ is an unsubstituted lower alkanyl or benzyl. Specific exemplary phosphate ester progroups include, but are not limited to, —CH$_2$—O—P(O)(OH)(OR$^e$), —CH$_2$CH$_2$—O—P(O)(OH)(OR$^e$), —CH$_2$—O—P(O)(OR$^e$)(OR$^e$) and —CH$_2$CH$_2$—O—P(O)(OR$^e$)(OR$^e$), where R$^e$ is selected from lower alkanyl, i-propyl and t-butyl.

In other embodiments, R$^2$, R$^3$, or both independently may be cyclic phosphate ester-containing progroups of the formula

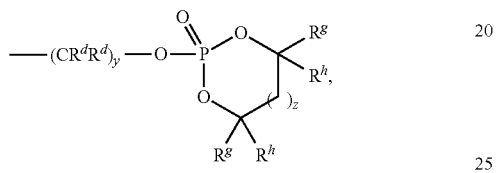

wherein each R$^g$ is, independently of the others, selected from hydrogen and lower alkyl; each R$^h$ is, independently of the others, selected from hydrogen, substituted or unsubstituted lower alkyl, substituted or unsubstituted lower cycloheteroalkyl, substituted or unsubstituted (C6-C14) aryl, substituted or unsubstituted (C7-C20) arylalkyl and substituted or unsubstituted 5-14 membered heteroaryl; z is an integer ranging from 0 to 2; and R$^d$ and y are as previously described. In a specific embodiment, a phosphate ester-containing progroup R$^2$, R$^3$, or both is a cyclic phosphate ester of the formula

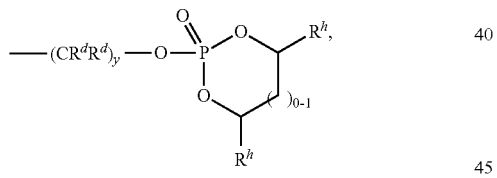

where R$^d$, R$^h$ and y are as previously defined.

Without being limited to any particular theory of operation, the mechanism by which cyclic phosphate ester prodrugs including such cyclic phosphate ester progroups metabolize in vivo to the active drug compound depends, in part, on the identity of the R$^h$ substituent. For example, cyclic phosphate ester progroups in which each R$^h$ is, independently of the others, selected from hydrogen and lower alkyl are cleaved in vivo by esterases. Thus, in some embodiments, the cyclic phosphate ester progroups are selected such that they are cleavable in vivo by esterases. Specific examples of such cyclic phosphate ester progroups include, but are not limited to, progroups selected from

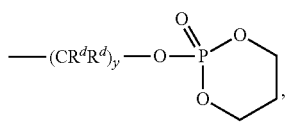

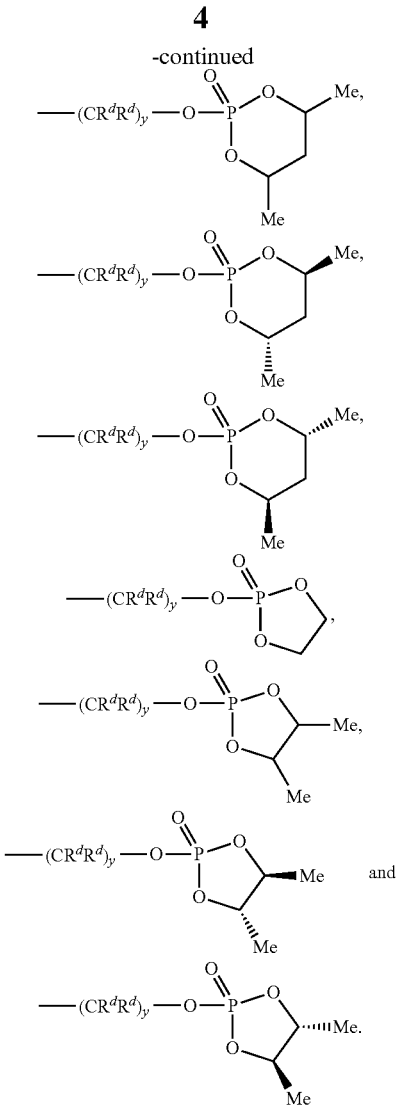

Alternatively, cyclic phosphate ester prodrugs having progroups in which the R$^h$ substituents are substituted or unsubstituted aryl, arylalkyl and heteroaryl groups, are not typically cleaved by esterases, but are instead metabolized to the active prodrug by enzymes, such as cytochrome P$_{450}$ enzymes, that reside in the liver. For example, a series of cyclic phosphate ester nucleotide prodrugs that undergo an oxidative cleavage reaction catalyzed by a cytochrome P$_{450}$ enzyme (CYP) expressed predominantly in the liver are described in Erion et al., 2004, J. Am. Chem. Soc. 126:5154-5163. In some embodiments, the cyclic phosphate ester progroups are selected such that they are cleavable by CYP enzymes expressed in the liver. Specific exemplary embodiments of such cyclic phosphate ester-containing progroups include, but are not limited to, progroups having the formula

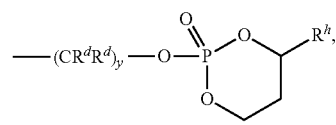

where R$^h$ is selected from phenyl, 3-chlorophenyl, 4-pyridyl and 4-methoxyphenyl;

$R^4$ and $R^5$ are each, independently of one another, H, (C1-C6) alkyl, (C1-C6) haloalkyl, (C1-C6) alkoxy, halogen, (C1-C6) haloalkoxy, (C1-C6) aminoalkyl or (C1-C6) hydroxyalkyl; or, alternatively, $R^4$ and $R^5$, taken together with the carbon atom to which they are bonded, form a spirocycloalkyl or a spirocycloheteroalkyl, or, alternatively, $R^4$ and $R^5$, taken together with the carbon atom to which they are bonded, form a C=O group;

$R^6$ and $R^7$ are each, independently of one another, H, (C1-C6) alkyl, (C1-C6) haloalkyl, (C1-C6) alkoxy, halogen, (C1-C6) haloalkoxy, (C1-C6) aminoalkyl or (C1-C6) hydroxyalkyl; or, alternatively, $R^6$ and $R^7$, taken together with the carbon atom to which they are bonded, form a spirocycloalkyl or a spirocycloheteroalkyl or, alternatively, $R^6$ and $R^7$, taken together with the carbon atom to which they are bonded, form a C=O group;

$R^8$ is H, halo, (C1-C6) alkyl optionally substituted with one or more of the same or different $R^{11}$ groups, (C1-C3) haloalkyloxy, —$OR^d$, —$SR^d$, —$NR^cR^c$, (C1-C3) haloalkyl, —C(O)$OR^d$, —CN, —NC, —OCN, —SCN, —NO or —$NO_2$;

two $R^9$, taken together with the nitrogen atom to which they are bonded, form a 4- to 8-membered monocyclic cycloheteroalkyl, 6- to 10-membered bridged bicyclic cycloheteroalkyl, or 6- to 12-membered bridged tricyclic cycloheteroalkyl, wherein each may optionally be substituted with one or more of the same or different $R^{11}$ groups, and wherein the substituted or unsubstituted mono-, bi- or tricyclic cycloheteroalkyl includes at least two nitrogen atoms;

each $R^{10}$ is independently $R^{11}$ or alternatively, two $R^{10}$ on vicinal carbons, taken together with the carbons to which they are bonded, form a ring fused to A, where the ring fused to A is a 5- to 8-membered cycloalkyl, a 5- to 8-membered cycloheteroalkyl, 5- to 6-membered aryl or a 5- to 6-membered heteroaryl, each optionally substituted with one or more of the same or different $R^{11}$ groups;

each $R^{11}$ is independently H, $R^e$, $R^b$, $R^e$ substituted with one or more of the same or different $R^a$ and/or $R^b$, —$OR^e$ substituted with one or more of the same or different $R^a$ and/or $R^b$, —$SR^e$ substituted with one or more of the same or different $R^a$ and/or $R^b$, —C(O)$R^e$ substituted with one or more of the same or different $R^a$ and/or $R^b$, —N($R^a$)$R^e$ where $R^e$ is substituted with one or more of the same or different $R^a$ and/or $R^b$, —S(O)$_2R^e$ substituted with one or more of the same or different $R^a$ and/or $R^b$, —N($R^a$)—S(O)$_2R^e$ where $R^e$ is substituted with one or more of the same or different $R^a$ and/or $R^b$, —B(O$R^a$)$_2$, —B(N($R^c$)$_2$)$_2$, —(C($R^a$)$_2$)$_m$—$R^b$, —O—(C($R^a$)$_2$)$_m$—$R^b$, —S—(C($R^a$)$_2$)$_m$—$R^b$, —O—(C($R^b$)$_2$)$_m$—$R^a$, —N($R^a$)—(C($R^a$)$_2$)$_m$—$R^b$, —O—(CH$_2$)$_m$—CH((CH$_2$)$_m$$R^b$)$R^b$, —C(O)N($R^a$)—(C($R^a$)$_2$)$_m$—$R^b$, —O—(C($R^a$)$_2$)$_m$—C(O)N($R^a$)—(C($R^a$)$_2$)$_m$—$R^b$, —N((C($R^a$)$_2$)$_m$$R^b$)$_2$, —S—(C($R^a$)$_2$)$_m$—C(O)N($R^a$)—(C($R^a$)$_2$)$_m$—$R^b$, —N($R^a$)—C(O)—N($R^a$)—(C($R^a$)$_2$)$_m$—$R^b$, —N($R^a$)—C(O)—(C($R^a$)$_2$)$_m$—C($R^a$)($R^b$)$_2$ or —N($R^a$)—(C($R^a$)$_2$)$_m$—C(O)—N($R^a$)—(C($R^a$)$_2$)$_m$—$R^b$;

each $R^a$ is independently H, deuterium, (C1-6)alkyl, (C3-8)cycloalkyl, (C4-11)cycloalkylalkyl, (C6-10)aryl, (C7-16)arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each $R^b$ is independently =O, —$OR^a$, —O—(C($R^a$)$_2$)$_m$—$OR^a$, (C1-3)haloalkyloxy, —$OCF_3$, =S, —$SR^a$, =$NR^a$, =$NOR^a$, —N($R^c$)$_2$, halo, —$CF_3$, —CN, —NC, —OCN, —SCN, —NO, —$NO_2$, =$N_2$, —$N_3$, —S(O)$R^a$, —S(O)$_2R^a$, —$SO_3R^a$, —S(O)N($R^c$)$_2$, —S(O)$_2$N($R^c$)$_2$, —OS(O)$R^a$, —OS(O)$_2R^a$, —OS$O_3R^a$, —OS(O)$_2$N($R^c$)$_2$, —C(O)$R^a$, —$CO_2R^a$, —C(O)N($R^c$)$_2$, —C(N$R^a$)—N($R^c$)$_2$, —C(NOH)—$R^a$, —C(NOH)—N($R^c$)$_2$, —OC(O)$R^a$, —OC(O)$OR^a$, —OC(O)N($R^c$)$_2$, —OC(NH)—N($R^c$)$_2$, —OC(N$R^a$)—N($R^c$)$_2$, —N($R^a$)—S(O)$_2$H, —[N($R^a$)C(O)]$_n$$R^a$, —[N($R^a$)C(O)]$_n$$OR^a$, —[N($R^a$)C(O)]$_n$($R^c$)$_2$ or —[N($R^a$)C(N$R^a$)]$_n$—N($R^c$)$_2$;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$OR^a$, —$OCF_3$, =S, —$SR^a$, =$NR^a$, =$NOR^a$, —N($R^a$)$_2$, halo, —$CF_3$, —CN, —NC, —OCN, —SCN, —NO, —$NO_2$, =$N_2$, —$N_3$, —S(O)$R^a$, —S(O)$_2R^a$, —$SO_3R^a$, —S(O)N($R^a$)$_2$, —S(O)$_2$N($R^a$)$_2$, —OS(O)$R^a$, —OS(O)$_2R^a$, —OS$O_3R^a$, —OS(O)$_2$N($R^a$)$_2$, —C(O)$R^a$, —$CO_2R^a$, —C(O)N($R^a$)$_2$, —C(N$R^a$)N($R^a$)$_2$, —C(NOH)$R^a$, —C(NOH)N($R^a$)$_2$, —$OCO_2R^a$, —OC(O)N($R^a$)$_2$, —OC(N$R^a$)N($R^a$)$_2$, —[N($R^a$)C(O)]$_n$$R^a$, —(C($R^a$)$_2$)$_n$—$OR^a$, —N($R^a$)—S(O)$_2R^a$, —C(O)—(C1-6)haloalkyl, —S(O)$_2$—(C1-6)haloalkyl, —OC(O)$R^a$, —O(C($R^a$)$_2$)$_m$—$OR^a$, —S(C($R^a$)$_2$)$_m$—$OR^a$, —N($R^a$)—(C1-6)haloalkyl, —P(O)(O$R^a$)$_2$, —N($R^a$)—(C($R^a$)$_2$)$_m$—$OR^a$, —[N($R^a$)C(O)]$_n$$OR^a$, —[N($R^a$)C(O)]$_n$N($R^a$)$_2$, —[N($R^a$)C(N$R^a$)]$_n$N($R^a$)$_2$ or —N($R^a$)C(O)(C1-6)haloalkyl; two $R^d$, taken together with the atom or atoms to which they are attached, combine to form a 3-10 membered partially or fully saturated mono or bicyclic ring, optionally containing one or more heteroatoms and optionally substituted with one or more $R^a$;

each $R^e$ is independently (C1-6)alkyl, (C3-8)cycloalkyl, (C4-11)cycloalkylalkyl, (C6-10)aryl, (C7-16)arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each m is independently an integer from 1 to 3; and
each n is independently an integer from 0 to 3;
provided the compound is not:
N4-(3,4-Dihydro-2H-benzo[1,4]oxazin-6-yl)-5-fluoro-N2-[3-(4-methyl-piperazin-1-yl)-phenyl]-pyrimidine-2,4-diamine;
4-{3-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid methyl ester;
N4-(3,4-Dihydro-2H-pyrido[3,2-b][1,4]oxazin-6-yl)-5-fluoro-N2-[3-(4-methyl-piperazin-1-yl)-phenyl]-pyrimidine-2,4-diamine;
4-{3-[4-(3,4-Dihydro-2H-pyrido[3,2-b][1,4]oxazin-6-ylamino)-5-fluoro-pyrimidin-2-ylamino]-phenyl}-piperazine-1-carboxylic acid ethyl ester;
1-(4-{3-[4-(3,4-Dihydro-2H-pyrido[3,2-b][1,4]oxazin-6-ylamino)-5-fluoro-pyrimidin-2-ylamino]-phenyl}-piperazin-1-yl)-ethanone;
6-{5-Fluoro-2-[3-(4-methyl-piperazin-1-yl)-phenylamino]-pyrimidin-4-ylamino}-2,2-dimethyl-4H-pyrido[3,2-b][1,4]oxazin-3-one;
6-{2-[3-(4-Acetyl-piperazin-1-yl)-phenylamino]-5-fluoro-pyrimidin-4-ylamino}-2,2-dimethyl-4H-pyrido[3,2-b][1,4]oxazin-3-one;
4-{3-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid ethyl ester;
6-{5-Fluoro-2-[3-(4-methyl-piperazin-1-yl)-phenylamino]-pyrimidin-4-ylamino}-4H-pyrido[3,2-b][1,4]oxazin-3-one;

6-{2-[3-(4-Acetyl-piperazin-1-yl)-phenylamino]-5-fluoro-pyrimidin-4-ylamino}-4H-pyrido[3,2-b][1,4]oxazin-3-one;

4-{3-[5-Fluoro-4-(3-oxo-3,4-dihydro-2H-pyrido[3,2-b][1,4]oxazin-6-ylamino)-pyrimidin-2-ylamino]-phenyl}-piperazine-1-carboxylic acid ethyl ester;

N4-(3,4-Dihydro-2H-pyrido[3,2-b][1,4]oxazin-6-yl)-5-fluoro-N2-[3-methyl-4-(4-methyl-piperazin-1-yl)-phenyl]-pyrimidine-2,4-diamine;

N2-[3-Chloro-4-(4-methyl-piperazin-1-yl)-phenyl]-N4-(3,4-dihydro-2H-pyrido[3,2-b][1,4]oxazin-6-yl)-5-fluoro-pyrimidine-2,4-diamine;

N4-(3,4-Dihydro-2H-pyrido[3,2-b][1,4]oxazin-6-yl)-5-fluoro-N2-[4-(4-methyl-piperazin-1-yl)-phenyl]-pyrimidine-2,4-diamine;

4-{4-[4-(3,4-Dihydro-2H-pyrido[3,2-b][1,4]oxazin-6-ylamino)-5-fluoro-pyrimidin-2-ylamino]-phenyl}-piperazine-1-carboxylic acid ethyl ester;

1-(4-{4-[4-(3,4-Dihydro-2H-pyrido[3,2-b][1,4]oxazin-6-ylamino)-5-fluoro-pyrimidin-2-ylamino]-phenyl}-piperazin-1-yl)-ethanone;

4-{4-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid ethyl ester;

4-{4-[5-Fluoro-4-(3-oxo-3,4-dihydro-2H-pyrido[3,2-b][1,4]oxazin-6-ylamino)-pyrimidin-2-ylamino]-phenyl}-piperazine-1-carboxylic acid ethyl ester;

6-{5-Fluoro-2-[4-(4-methyl-piperazin-1-yl)-phenylamino]-pyrimidin-4-ylamino}-2,2-dimethyl-4H-pyrido[3,2-b][1,4]oxazin-3-one;

6-{5-Fluoro-2-[4-(4-methyl-piperazin-1-yl)-phenylamino]-pyrimidin-4-ylamino}-4H-pyrido[3,2-b][1,4]oxazin-3-one;

6-{2-[4-(4-Acetyl-piperazin-1-yl)-phenylamino]-5-fluoro-pyrimidin-4-ylamino}-2,2-dimethyl-4H-pyrido[3,2-b][1,4]oxazin-3-one;

4-{4-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid methyl ester;

4-{4-[5-Fluoro-4-(3-oxo-3,4-dihydro-2H-pyrido[3,2-b][1,4]oxazin-6-ylamino)-pyrimidin-2-ylamino]-phenyl}-piperazine-1-carboxylic acid methyl ester; or 6-{2-[4-(4-Acetyl-piperazin-1-yl)-phenylamino]-5-fluoro-pyrimidin-4-ylamino}-4H-pyrido[3,2-b][1,4]oxazin-3-one.

In another aspect, the compound of Formula I is provided, wherein two $R^9$, taken together with the nitrogen atom to which they are bonded, form a 6- to 10-membered bridged bicyclic cycloheteroalkyl, which may be optionally substituted with one or more of the same or different $R^{11}$ groups, and wherein the substituted or unsubstituted bridged bicyclic cycloheteroalkyl includes at least two nitrogen atoms.

In yet another aspect, a pharmaceutical composition is provided, which includes a pharmaceutically acceptable carrier and a therapeutically effective amount of one or more of the pyrimidinediamine compounds provided herein, including pharmaceutically acceptable salts, solvates, and prodrugs thereof, e.g., a compound of Formula I. The exact nature of the carrier will depend upon the desired use for the composition, and may range from being suitable or acceptable for veterinary uses to being suitable or acceptable for human use.

The pyrimidinediamine compounds provided herein are potent inhibitors of PLK1 in in vitro assays. Accordingly, in yet another aspect, a method of treating a disease or condition associated with enhanced PLK1 catalytic activity in a mammal is provided. The method includes administering to a mammal in need thereof, a therapeutically effective amount of one or more of the pyrimidinediamine compounds disclosed herein, including pharmaceutically acceptable salts, solvates, prodrugs, and compositions thereof, e.g., a compound of Formula I disclosed above.

In yet another aspect, use of one or more of the pyrimidinediamine compounds disclosed herein, including pharmaceutically acceptable salts, solvates, and prodrugs thereof, in the manufacture of a medicament for treatment of a disease or condition associated with enhanced PLK1 catalytic activity, is provided.

In some embodiments, the disease or condition associated with enhanced PLK1 catalytic activity is a disease or condition associated with abnormal cell proliferation, e.g., a cancer or a neoplasm.

Examples of such diseases include without limitation leukemia, lymphoma (Hodgkin's and non-Hodgkin's), malignancies of the brain, bladder, breast, colon, lung, ovaries, pancreas, prostate, skin, and uterus, including solid tumors, such as carcinomas and sarcomas, as well as other proliferative conditions, such as benign tumors.

In certain embodiments, a method of inhibiting proliferation of a cell is provided, the method including contacting the cell with an effective amount of one or more of the pyrimidinediamine compounds disclosed herein, including pharmaceutically acceptable salts, solvates, and prodrugs thereof.

DETAILED DESCRIPTION

"Alkyl" by itself or as part of another substituent refers to a saturated or unsaturated branched, or straight-chain acyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, prop-1-en-1-yl, prop-1-en-2-yl, prop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, and the like. Where specific levels of saturation are intended, the nomenclature "alkanyl," "alkenyl" and/or "alkynyl" is used, as defined below. In some embodiments, the alkyl groups are (C1-C6) alkyl.

"Alkanyl" by itself or as part of another substituent refers to a saturated branched or straight-chain acyclic alkyl derived by the removal of one hydrogen atom from a single carbon atom of a parent alkane. Typical alkanyl groups include, but are not limited to, methanyl; ethanyl; propanyls such as propan-1-yl and propan-2-yl (isopropyl); butanyls such as butan-1-yl, butan-2-yl (sec-butyl), 2-methyl-propan-1-yl (isobutyl), 2-methyl-propan-2-yl (t-butyl), etc., and the like. In some embodiments, the alkanyl groups are (C1-C6) alkanyl.

"Alkenyl" by itself or as part of another substituent refers to an unsaturated branched or straight-chain acyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, and the like. In some embodiments, the alkenyl group is (C2-C6) alkenyl.

"Alkynyl" by itself or as part of another substituent refers to an unsaturated branched or straight-chain acyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, and the like. In some embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The location of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

A "bivalent linker" refers to a straight-chain or branched moiety which may be cyclic or acyclic that is capable of forming two bonds to the atoms that are to be linked. The bonds can originate from one atom, two vicinal atoms, or two terminal atoms. Examples of bivalent linkers include without limitation alkyldyil and alkyleno linkers, as well as bivalent aryls, heteroaryls, heteroalkyl, etc.

"Heteroalkyl," "Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen, (C1-C6) alkyl, or as specifically defined.

"Cycloalkyl" and "Heterocycloalkyl" (or "Cycloheteroalkyl") by themselves or as part of another substituent refer to cyclic versions of "alkyl" and "heteroalkyl" groups, respectively, including monycyclic, bicyclic, and tricyclic systems. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; bicyclic groups such as decalinyl, and norbornyl, and tricyclic groups such as adamantyl and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), 1,4-diazabicyclo-[2.2.2]octanyl, and the like.

"Bridged bicyclic heterocycloalkyl (or cycloheteroalkyl)" by itself or as part of another substituent refers to a bicyclic cycloalkyl, containing at least one bridge atom between two bridgehead atoms, where one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen, (C1-C6) alkyl, or as specifically defined. "Bridged bicyclic cycloheteroalkyl" is a type of "heterocycloalkyl". Examples of geometries of bridged bicyclic heteroalkyls include without limitation [3.3.3], [3.3.2], [3.3.1], [3.2.2], [3.2.1], [2.2.2], and [2.2.1]. Examples of bridged bicyclic cycloheteroalkyls containing two nitrogen atoms include without limitation:

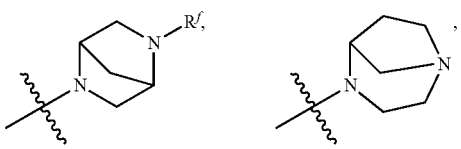

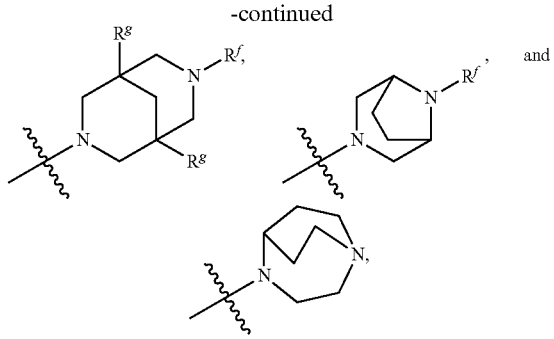

wherein $R^f$ and $R^g$ are each independently H, C1-C6 alkyl, or as specifically defined.

"Bridged tricyclic cycloheteroalkyl (or cycloheteroalkyl)" by itself or as part of another substituent refers to a tricyclic cycloalkyl, containing at least one bridge atom between two bridgehead atoms, where one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)₂—, —S(O)NR'—, —S(O)₂NR'—, and the like, including combinations thereof, where each R' is independently hydrogen, (C1-C6) alkyl, or as specifically defined. "Bridged bicyclic cycloheteroalkyl" is a type of "heterocycloalkyl". Examples of bridged bicyclic heteroalkyls containing two nitrogen atoms include all-bridged ring systems like diazaadamantyls, and bridged-fused ring systems, for example:

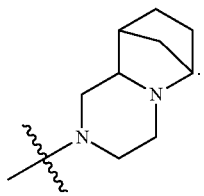 [SMILES: *N1CCN2C3CCC(C3)C2C1]

"Spirocycloalkyl and spirocycloheteroalkyl (or spiroheterocycloalkyl)" by itself or as part of another substituent refers to a polycyclic (e.g., bicyclic) cycloalkyl or heterocycloalkyl, or one cycle thereof, which contains a single quartenary carbon atom as a connection point between at least two rings. Spirocycloalkyl and spirocycloheteroalkyl may in fact describe the same ring system, e.g. a piperidine ring in a spirocyclic arrangement with the cyclohexane, as for example in the formula:

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is (C5-C15) aryl, such as (C5-C10) aryl. In some embodiments, preferred aryls are cyclopentadienyl, phenyl and naphthyl.

"Arylalkyl" by itself or as part of another substituent refers to an alkyl group in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, the arylalkyl group is (C6-C21) arylalkyl, e.g., the alkanyl, alkenyl or alkynyl moiety of the arylalkyl group is (C1-C6) and the aryl moiety is (C5-C15). In some embodiments the arylalkyl group is (C6-C13), e.g., the alkanyl, alkenyl or alkynyl moiety of the arylalkyl group is (C1-C3) and the aryl moiety is (C5-C10).

"Heteroarylalkyl" by itself or as part of another substituent refers to an acyclic alkyl group in which one of the hydrogen atoms bonded to a carbon atom, typically a terminal or sp³ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In some embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Prodrug" refers to a derivative of an active 2,4-pyrimidinediamine compound (drug) that requires a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking a functional group in the 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active 2,4-pyrimidinediamines compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ includes the progroup —C(O)CH$_3$.

"Mammal" includes humans and domestic animals, such as cats, dogs, swine, cattle, sheep, goats, horses, rabbits, and the like. In some embodiments, the mammal is a human.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid (p-TSA), trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound provided herein and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of which, when administered to a mammal, such as a human, is sufficient to effect treatment, as defined below, of a disease or condition of interest in the mammal, (e.g., a human). The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, such as a human, having the disease or condition of interest, and includes at least one of the following: (i) preventing the disease or condition from occurring in a mammal, in particular, when such mammal is predisposed to the condition but has not yet been diagnosed as having it; (ii) inhibiting the disease or condition, by for example, arresting its development; (iii)

relieving the disease or condition, e.g., relieving the symptoms of disease or conditions, or causing regression of disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds provided herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers Likewise, all tautomeric forms are also intended to be included. The compounds of the present invention do not include those which are known in the art to be too unstable to synthesize and/or isolate.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable minor images of one another.

A "tautomer" refers to a proton shift from one atom of a molecule to another atom of the same molecule. The present invention includes tautomers of any said compounds.

"Atropisomers" are stereoisomers resulting from hindered rotation about single bonds where the barrier to rotation is high enough to allow for the isolation of the conformers (Eliel, E. L.; Wilen, S. H. Stereochemistry of Organic Compounds; Wiley & Sons: New York, 1994; Chapter 14). Atropisomerism is significant because it introduces an element of chirality in the absence of stereogenic atoms. The invention is meant to encompass atropisomers, of any said compounds and/or prodrugs provided herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are intended to be within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

2,4-Pyrimidinediamine Compounds

In one aspect, provided herein is a compound according to Formula I:

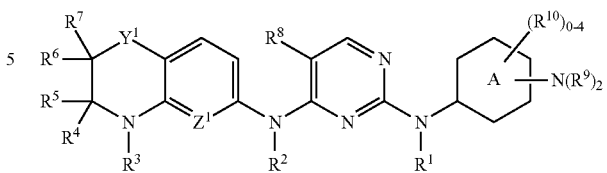

or a pharmaceutically acceptable salt, a solvate, an N-oxide, or a prodrug thereof, wherein:

$Y^1$ is O or S;

$Z^1$ is CH or N;

A is phenyl or a 6-membered heteroaryl;

$R^1$ is H;

$R^2$ and $R^3$ are each, independently of one another, H, (C1-C6) alkyl optionally substituted with one or more of the same or different $R^{11}$ groups, (C3-C8) cycloalkyl optionally substituted with one or more of the same or different $R^{11}$ groups, (C4-C11) cycloalkylalkyl optionally substituted with one or more of the same or different $R^{11}$ groups, (C5-C10) aryl optionally substituted with one or more of the same or different $R^{11}$ groups, (C6-C16) arylalkyl optionally substituted with one or more of the same or different $R^{11}$ groups, 2-6 membered heteroalkyl optionally substituted with one or more of the same or different $R^{11}$ groups, 3-8 membered cycloheteroalkyl, optionally substituted with one or more of the same or different $R^{11}$ groups, 4-11 membered cycloheteroalkylalkyl, optionally substituted with one or more of the same or different $R^{11}$ groups, 5-10 membered heteroaryl optionally substituted with one or more of the same or different R" groups or 6-16 membered heteroarylalkyl optionally substituted with one or more of the same or different R" groups;

$R^4$ and $R^5$ are each, independently of one another, H, (C1-C6) alkyl, (C1-C6) haloalkyl, (C1-C6) alkoxy, halogen, (C1-C6) haloalkoxy, (C1-C6) aminoalkyl or (C1-C6) hydroxyalkyl; or, alternatively, $R^4$ and $R^5$, taken together with the carbon atom to which they are bonded, form a spirocycloalkyl or a spirocycloheteroalkyl, or, alternatively, $R^4$ and $R^5$, taken together with the carbon atom to which they are bonded, form a C=O group;

$R^6$ and $R^7$ are each, independently of one another, H, (C1-C6) alkyl, (C1-C6) haloalkyl, (C1-C6) alkoxy, halogen, (C1-C6) haloalkoxy, (C1-C6) aminoalkyl or (C1-C6) hydroxyalkyl; or, alternatively, $R^6$ and $R^7$, taken together with the carbon atom to which they are bonded, form a spirocycloalkyl or a spirocycloheteroalkyl or, alternatively, $R^6$ and $R^7$, taken together with the carbon atom to which they are bonded, form a C=O group;

$R^8$ is H, halo, (C1-C6) alkyl optionally substituted with one or more of the same or different $R^{11}$ groups, (C1-C3) haloalkyloxy, —$OR^d$, —$SR^d$, —$NR^cR^c$, (C1-C3) haloalkyl, —C(O)$OR^d$, —CN, —NC, —OCN, —SCN, —NO or —$NO_2$;

two $R^9$, taken together with the nitrogen atom to which they are bonded, form a 4- to 8-membered monocyclic cycloheteroalkyl, 6- to 10-membered bridged bicyclic cycloheteroalkyl, or 6- to 12-membered bridged tricyclic cycloheteroalkyl, wherein each may optionally be substituted with one or more of the same or different $R^{11}$ groups, and wherein the substituted or unsubstituted mono-, bi- or tricyclic cycloheteroalkyl includes at least two nitrogen atoms;

each $R^{10}$ is independently $R^{11}$ or alternatively, two $R^{10}$ on vicinal carbons, taken together with the carbons to which they are bonded, form a ring fused to A, where the ring fused to A is a 5- to 8-membered cycloalkyl, a 5- to 8-membered cycloheteroalkyl, 5- to 6-membered aryl or a 5- to 6-membered heteroaryl, each optionally substituted with one or more of the same or different $R^{11}$ groups;

each $R^{11}$ is independently H, $R^e$, $R^b$, $R^e$ substituted with one or more of the same or different $R^a$ and/or $R^b$, —$OR^e$ substituted with one or more of the same or different $R^a$ and/or $R^b$, —$SR^e$ substituted with one or more of the same or different $R^a$ and/or $R^b$, —$C(O)R^e$ substituted with one or more of the same or different $R^a$ and/or $R^b$, —$N(R^a)R^e$ where $R^e$ is substituted with one or more of the same or different $R^a$ and/or $R^b$, —$S(O)_2R^e$ substituted with one or more of the same or different $R^a$ and/or $R^b$, —$N(R^a)$—$S(O)_2R^e$ where $R^e$ is substituted with one or more of the same or different $R^a$ and/or $R^b$, —$B(OR^a)_2$, —$B(N(R^c)_2)_2$, —$(C(R^a)_2)_m$—$R^b$, —O—$(C(R^a)_2)_m$—$R^b$, —S—$(C(R^a)_2)_m$—$R^b$, —O—$(C(R^b)_2)_m$—$R^a$, —$N(R^a)$—$(C(R^a)_2)_m$—$R^b$, —O—$(CH_2)_m$—$CH((CH_2)_mR^b)R^b$, —$C(O)N(R^a)$—$(C(R^a)_2)_m$—$R^b$, —O—$(C(R^a)_2)_m$—$C(O)N(R^a)$—$(C(R^a)_2)_m$—$R^b$, —$N((C(R^a)_2)_mR^b)_2$, —S—$(C(R^a)_2)_m$—$C(O)N(R^a)$—$(C(R^a)_2)_m$—$R^b$, —$N(R^a)$—$C(O)$—$N(R^a)$—$(C(R^a)_2)_m$—$R^b$, —$N(R^a)$—$C(O)$—$(C(R^a)_2)_m$—$C(R^a)(R^b)_2$ or —$N(R^a)$—$(C(R^a)_2)_m$—$C(O)$—$N(R^a)$—$(C(R^a)_2)_m$—$R^b$;

each $R^a$ is independently H, deuterium, (C1-6)alkyl, (C3-8)cycloalkyl, (C4-11)cycloalkylalkyl, (C6-10)aryl, (C7-16)arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each $R^b$ is independently =O, —$OR^a$, —O—$(C(R^a)_2)_m$—$OR^a$, (C1-3)haloalkyloxy, —$OCF_3$, =S, —$SR^a$, =$NR^a$, =$NOR^a$, —$N(R^c)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^c)_2$, —$S(O)_2N(R^c)_2$, —$OS(O)R^a$, —$OS(O)_2R^a$, —$OSO_3R^a$, —$OS(O)_2N(R^c)_2$, —$C(O)R^a$, —$CO_2R^a$, —$C(O)N(R^c)_2$, —$C(NR^a)$—$N(R^c)_2$, —C(NOH)—$R^a$, —C(NOH)—$N(R^c)_2$, —$OC(O)R^a$, —$OC(O)OR^a$, —$OC(O)N(R^c)_2$, —$OC(NH)$—$N(R^c)_2$, —$OC(NR^a)$—$N(R^c)_2$, —$N(R^a)$—$S(O)_2H$, —$[N(R^a)C(O)]_nR^a$, —$[N(R^a)C(O)]_nOR^a$, —$[N(R^a)C(O)]_nN(R^c)_2$ or —$[N(R^a)C(NR^a)]_nN(R^c)_2$;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$OR^a$, —$OCF_3$, =S, —$SR^a$, =$NR^a$, =$NOR^a$, —$N(R^a)_2$, halo, —$CF_3$, —CN, —NC, —OCN, —SCN, —NO, —$NO_2$, =$N_2$, —$N_3$, —$S(O)R^a$, —$S(O_2)R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —$[N(R^a)C(O)]_nR^a$, $(C(R^a)_2)_n$—$OR^a$, —$N(R^a)$—$S(O)_2R^a$, —$C(O)$—(C1-6)haloalkyl, —$S(O)_2$—(C1-6)haloalkyl, —$C(O)R^a$, —$O(C(R^a)_2)_m$—$OR^a$, —$S(C(R^a)_2)_m$—$OR^a$, —$N(R^a)$—(C1-6)haloalkyl, —$P(O)(OR^a)_2$, —$N(R^a)$—$(C(R^a)_2)_m$—$OR^a$, —$[N(R^a)C(O)]_nOR^a$, —$[N(R^a)C(O)]_nN(R^a)_2$, —$[N(R^a)C(NR^a)]_nN(R^a)_2$ or —$N(R^a)C(O)(C1-6)haloalkyl; two $R^d$, taken together with the atom or atoms to which they are attached, combine to form a 3-10 membered partially or fully saturated mono or bicyclic ring, optionally containing one or more heteroatoms and optionally substituted with one or more $R^a$;

each $R^e$ is independently (C1-6)alkyl, (C3-8)cycloalkyl, (C4-11)cycloalkylalkyl, (C6-10)aryl, (C7-16)arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each m is independently an integer from 1 to 3; and
each n is independently an integer from 0 to 3;
provided:
the compound is not:
4-{3-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid methyl ester;
N4-(3,4-Dihydro-2H-pyrido[3,2-b][1,4]oxazin-6-yl)-5-fluoro-N2-[3-(4-methyl-piperazin-1-yl)-phenyl]-pyrimidine-2,4-diamine;
4-{3-[4-(3,4-Dihydro-2H-pyrido[3,2-b][1,4]oxazin-6-ylamino)-5-fluoro-pyrimidin-2-ylamino]-phenyl}-piperazine-1-carboxylic acid ethyl ester;
1-(4-{3-[4-(3,4-Dihydro-2H-pyrido[3,2-b][1,4]oxazin-6-ylamino)-5-fluoro-pyrimidin-2-ylamino]-phenyl}-piperazin-1-yl)-ethanone;
6-{5-Fluoro-2-[3-(4-methyl-piperazin-1-yl)-phenylamino]-pyrimidin-4-ylamino}-2,2-dimethyl-4H-pyrido[3,2-b][1,4]oxazin-3-one;
6-{2-[3-(4-Acetyl-piperazin-1-yl)-phenylamino]-5-fluoro-pyrimidin-4-ylamino}-2,2-dimethyl-4H-pyrido[3,2-b][1,4]oxazin-3-one;
4-{3-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid ethyl ester;
6-{5-Fluoro-2-[3-(4-methyl-piperazin-1-yl)-phenylamino]-pyrimidin-4-ylamino}-4H-pyrido[3,2-b][1,4]oxazin-3-one;
6-{2-[3-(4-Acetyl-piperazin-1-yl)-phenylamino]-5-fluoro-pyrimidin-4-ylamino}-4H-pyrido[3,2-b][1,4]oxazin-3-one;
4-{3-[5-Fluoro-4-(3-oxo-3,4-dihydro-2H-pyrido[3,2-b][1,4]oxazin-6-ylamino)-pyrimidin-2-ylamino]-phenyl}-piperazine-1-carboxylic acid ethyl ester;
N4-(3,4-Dihydro-2H-pyrido[3,2-b][1,4]oxazin-6-yl)-5-fluoro-N2-[3-methyl-4-(4-methyl-piperazin-1-yl)-phenyl]-pyrimidine-2,4-diamine;
N2-[3-Chloro-4-(4-methyl-piperazin-1-yl)-phenyl]-N4-(3,4-dihydro-2H-pyrido[3,2-b][1,4]oxazin-6-yl)-5-fluoro-pyrimidine-2,4-diamine;
N4-(3,4-Dihydro-2H-pyrido[3,2-b][1,4]oxazin-6-yl)-5-fluoro-N2-[4-(4-methyl-piperazin-1-yl)-phenyl]-pyrimidine-2,4-diamine;
4-{4-[4-(3,4-Dihydro-2H-pyrido[3,2-b][1,4]oxazin-6-ylamino)-5-fluoro-pyrimidin-2-ylamino]-phenyl}-piperazine-1-carboxylic acid ethyl ester;
1-(4-{4-[4-(3,4-Dihydro-2H-pyrido[3,2-b][1,4]oxazin-6-ylamino)-5-fluoro-pyrimidin-2-ylamino]-phenyl}-piperazin-1-yl)-ethanone;
4-{4-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid ethyl ester;
4-{4-[5-Fluoro-4-(3-oxo-3,4-dihydro-2H-pyrido[3,2-b][1,4]oxazin-6-ylamino)-pyrimidin-2-ylamino]-phenyl}-piperazine-1-carboxylic acid ethyl ester;
6-{5-Fluoro-2-[4-(4-methyl-piperazin-1-yl)-phenylamino]-pyrimidin-4-ylamino}-2,2-dimethyl-4H-pyrido[3,2-b][1,4]oxazin-3-one;

6-{5-Fluoro-2-[4-(4-methyl-piperazin-1-yl)-phenylamino]-pyrimidin-4-ylamino}-4H-pyrido[3,2-b][1,4]oxazin-3-one;

6-{2-[4-(4-Acetyl-piperazin-1-yl)-phenylamino]-5-fluoro-pyrimidin-4-ylamino}-2,2-dimethyl-4H-pyrido[3,2-b][1,4]oxazin-3-one;

4-{4-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid methyl ester;

4-{4-[5-Fluoro-4-(3-oxo-3,4-dihydro-2H-pyrido[3,2-b][1,4]oxazin-6-ylamino)-pyrimidin-2-ylamino]-phenyl}-piperazine-1-carboxylic acid methyl ester; or 6-{2-[4-(4-Acetyl-piperazin-1-yl)-phenylamino]-5-fluoro-pyrimidin-4-ylamino}-4H-pyrido[3,2-b][1,4]oxazin-3-one.

In some embodiments the compound of Formula I is further not:

N4-(3,4-Dihydro-2H-benzo[1,4]oxazin-6-yl)-5-fluoro-N2-[3-(4-methyl-piperazin-1-yl)-phenyl]-pyrimidine-2,4-diamine.

In some embodiments the compound of Formula I excludes compounds 141-171 shown in Table 1, as well as N4-(3,4-Dihydro-2H-benzo[1,4]oxazin-6-yl)-5-fluoro-N2-[3-(4-methyl-piperazin-1-yl)-phenyl]-hpyrimidine-2,4-diamine; and 4-{3-[4-(2,2-Dimethyl-3-oxo-3,4-dihydro-2H-pyrido[3,2-b][1,4]oxazin-6-ylamino)-5-fluoro-pyrimidin-2-ylamino]-phenyl}-piperazine-1-carboxylic acid methyl ester.

In some embodiments:

(i) when A is

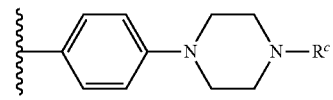

and $R^c$ is methyl, —C(O)OCH$_3$, —C(O)OCH$_2$CH$_3$ or —C(O)CH$_3$, the compound of Formula I is not

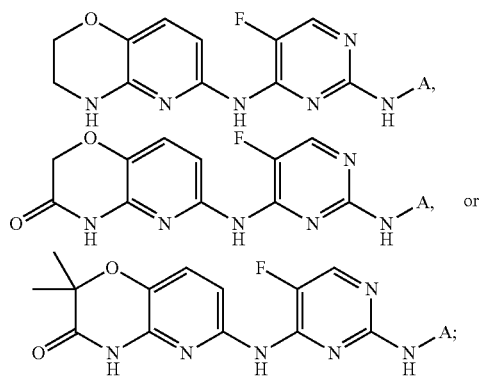

(ii) when A is

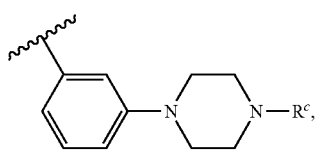

wherein $R^c$ is methyl, —C(O)OCH$_3$, —C(O)OCH$_2$CH$_3$ or —C(O)CH$_3$, the compound of Formula I is not

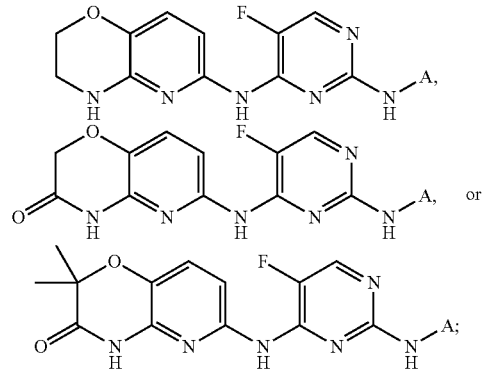

and (iii) when A is

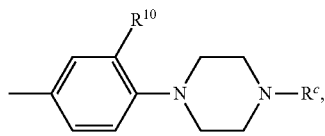

wherein $R^c$ is methyl and $R^{10}$ is methyl or chloro, the compound of Formula I is not

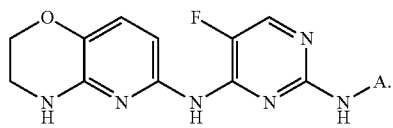

In addition to compounds described above, in some embodiments the compound of Formula I is not N4-(3,4-Dihydro-2H-benzo[1,4]oxazin-6-yl)-5-fluoro-N2-[3-(4-methyl-piperazin-1-yl)-phenyl]-pyrimidine-2,4-diamine.

In some embodiments, the compound of Formula I does not include simultaneously fluoro as $R^8$ and a substituted or unsubstituted piperazinyl as —N(R$^9$)$_2$.

In some embodiments, in the compound of Formula I, $Y^1$ is O. In some embodiments, in the compound of Formula I, $Y^1$ is S.

In some embodiments, in the compound of Formula I, $Z^1$ is CH. In some embodiments, in the compound of Formula I, $Z^1$ is N.

In some embodiments, in the compound of Formula I, A is phenyl. In some embodiments, in the compound of Formula I, A is a pyridyl.

In some embodiments, in the compound of Formula I, A is a 6-membered heteroaryl having two nitrogen atoms.

In some embodiments, in the compound of Formula I, $R^2$ is H, (C1-C6) alkyl, (C3-C6) cycloalkyl or (C4-C6) cycloalkylalkyl. In more specific embodiments, $R^2$ is H.

In some embodiments $R^3$, in the compound of Formula I is H, alkyl (including alkanyl, and alkynyl), haloalkyl, cycloalkyl, cycloalkylalkyl, arylalkyl optionally substituted with halo or alkoxy or heteroarylalkyl optionally substituted with halo or alkoxy.

In some embodiments, in the compound of Formula I, $R^4$ and $R^5$ are taken together with the carbon atom to which they are bonded to form a C=O group.

In some embodiments, in the compound of Formula I, $R^6$ and $R^7$, are each, independently of one another, H, halo or (C1-C6) alkyl, or, alternatively, $R^6$ and $R^7$ are taken together with the carbon atom to which they are bonded to form an optionally substituted spirocycloalkyl or an optionally substituted spirocycloheteroalkyl. In more specific embodiments, in the compound of Formula I, $R^6$ and $R^7$ are each independently H, halogen, methyl or ethyl. In some specific embodiments, in the compound of Formula I, $R^6$ and $R^7$ are simultaneously H. In some specific embodiments, in the compound of Formula I, $R^6$ and $R^7$ are simultaneously C1-C3 alkyl. In some specific embodiments, in the compound of Formula I, $R^6$ and $R^7$ are taken together with the carbon atom to which they are bonded to form an unsubstituted spirocycloalkyl.

In some embodiments, in the compound of Formula I, $R^8$ is H, (C1-C3) alkyl, (C1-C3) alkoxy, halogen, —CN, —NO$_2$, (C1-C3) haloalkyl, —C(O)OR$^d$ or (C1-C3) haloalkyloxy. In more specific embodiments, in the compound of Formula I, $R^8$ is H, (C1-C3) alkyl, (C1-C3) perfluoroalkyl, fluoro, chloro or alkoxy. In even more specific embodiments, in the compound of Formula I, $R^8$ is (C1-C3) perfluoroalkyl, fluoro or chloro.

In some embodiments, in the compound of Formula I, two $R^9$ are taken together with the nitrogen atom to which they are bonded form a 6- to 10-membered bridged bicyclic or a 6- to 12-membered bridged tricyclic group, each optionally substituted with one or more of the same or different $R^{11}$. In more specific embodiments, two $R^9$ are taken together with the nitrogen atom to which they are bonded form a 6- to 10-membered bridged bicyclic group optionally substituted with one or more of the same or different $R^{11}$. In some embodiments, the 6- to 10-membered bridged bicyclic group includes a geometry which is [3.3.3], [3.3.2], [3.3.1], [3.2.2], [3.2.1], [2.2.2] or [2.2.1].

In some embodiments, the 6- to 10-membered bridged bicyclic group includes a nitrogen atom substituted with an $R^f$ substituent, where $R^f$ is $R^a$, —S(O)$_2$R$^d$, —C(O)R$^d$, —C(O)OR$^d$ or —C(O)NR$^c$R$^c$. In a more specific embodiment, the 6- to 10-membered bridged bicyclic group is

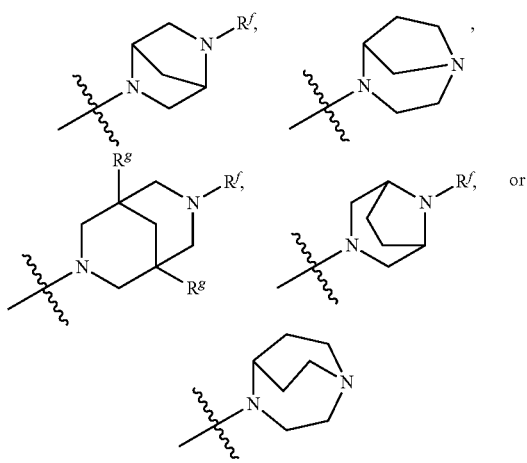

wherein $R^f$ is $R^a$, —S(O)$_2$R$^d$, —C(O)R$^d$, —C(O)OR$^d$ or —C(O)NR$^c$R$^c$; and wherein each $R^g$ is independently H, halogen or (C1-C6) alkyl.

In an even more specific embodiment the bridged bicyclic group is:

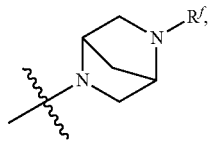

wherein $R^f$ is $R^a$, —S(O)$_2$R$^d$, —C(O)R$^d$, —C(O)OR$^d$ or —C(O)NR$^c$R$^c$.

In more specific embodiments, $R^f$ is H, (C1-C4) alkyl, (C4-C8) cycloalkylalkyl, —C(O)CH$_3$ or —SO$_2$CH$_3$, where $R^f$ is a substituent at a nitrogen on a 4- to 8-membered monocyclic cycloheteroalkyl, 6- to 10-membered bridged bicyclic cycloheteroalkyl, or 6- to 12-membered bridged tricyclic cycloheteroalkyl.

In some embodiments, in the compound of Formula I, the bridged bicyclic or bridged tricyclic group is

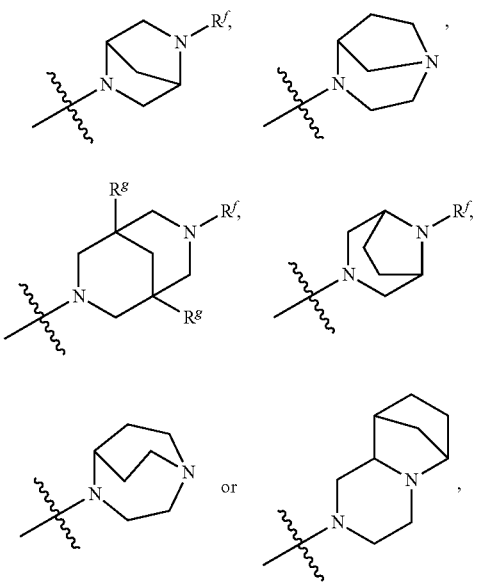

wherein $R^f$ is $R^a$, —S(O)$_2$R$^d$, —C(O)R$^d$, —C(O)OR$^d$ or —C(O)NR$^c$R$^c$; and wherein each $R^g$ is independently H, halogen or (C1-C6) alkyl. In more specific embodiments $R^f$ is H, (C1-C4) alkyl, (C4-C8) cycloalkylalkyl, —C(O)CH$_3$ or —SO$_2$CH$_3$.

In some embodiments in the compound of Formula I, $R^{10}$ is halogen, haloalkyl, alkyl, cycloalkyl, cycloalkylalkyl, alkoxy or cycloalkylalkyloxy, or alternatively, two $R^{10}$ on vicinal carbons, taken together with the carbons to which they are bonded, form a ring fused to A, the ring fused to A being a 5- to 8-membered cycloalkyl, a 5- to 8-membered cycloheteroalkyl, 5- to 6-membered aryl or a 5- to 6-membered heteroaryl, each optionally substituted with one or more of the same or different $R^{11}$ groups.

In a first specific embodiment, provided herein is a compound of Formula II:

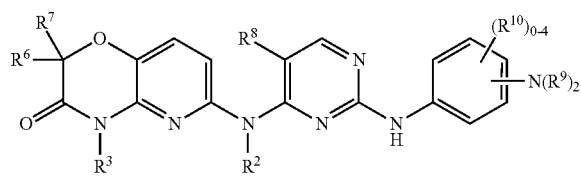

wherein, two $R^9$ taken together with the nitrogen atom to which they are bonded form a 6- to 10-membered bridged bicyclic group optionally substituted with one or more of the same or different $R^{11}$, wherein the bridged bicyclic group contains at least two annular nitrogen atoms;

$R^{10}$ is as defined above for compound I;

$R^8$ is H, (C1-C3) alkyl, (C1-C3) alkoxy, halogen, —CN, —NO$_2$, (C1-C3) haloalkyl, —C(O)OR$^d$ or (C1-C3) haloalkyloxy;

$R^2$ is H, (C1-C6) alkyl, (C3-C6) cycloalkyl or (C4-C6) cycloalkylalkyl;

$R^3$ is as defined above for Formula I;

$R^6$ and $R^7$ are each, independently of one another, H, halo or (C1-C6) alkyl, or, alternatively, $R^6$ and $R^7$ are taken together with the carbon atom to which they are bonded to form an optionally substituted spirocycloalkyl or an optionally substituted spirocycloheteroalkyl.

In a second embodiment, in accord with the first specific embodiment, $R^2$ is H.

In a third embodiment, in accord with the first specific embodiment or second embodiment thereof, the bridged bicyclic group is

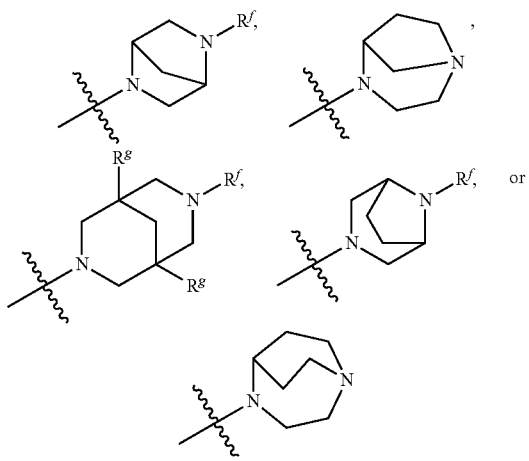

wherein $R^f$ is $R^a$, —S(O)$_2$R$^d$, —C(O)R$^d$, —C(O)OR$^d$ or —C(O)NR$^c$R$^c$; and wherein each $R^g$ is independently H, halogen or (C1-C6) alkyl.

In a fourth embodiment, in accord with the third embodiment, $R^f$ is H, (C1-C4) alkyl, (C4-C8) cycloalkylalkyl, —C(O)CH$_3$ or —SO$_2$CH$_3$; $R^{10}$ is halogen, haloalkyl, alkyl, cycloalkyl, cycloalkylalkyl, alkoxy or cycloalkylalkyloxy, or alternatively, two $R^{10}$ on vicinal carbons, taken together with the carbons to which they are bonded, form a ring fused to A, the ring fused to A being a 5- to 8-membered cycloalkyl, a 5- to 8-membered cycloheteroalkyl, 5- to 6-membered aryl or a 5- to 6-membered heteroaryl, each optionally substituted with one or more of the same or different $R^{11}$ groups; $R^3$ is as defined above for Formula I; $R^8$ is H, (C1-C3) alkyl, (C1-C3) perfluoroalkyl, fluoro, chloro or alkoxy; and $R^6$ and $R^7$ are each independently H, halogen, methyl or ethyl.

In a fifth embodiment, in accord with one of the first specific embodiment, the second, third or fourth embodiments, the compound is according to Formula III:

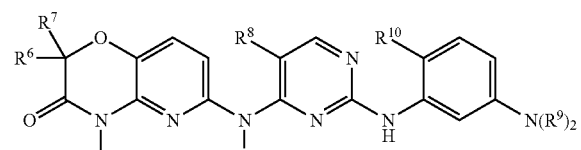

In a sixth embodiment, in accord with one of the first specific embodiment, the second, third or fourth embodiments, the compound is according to Formula IV:

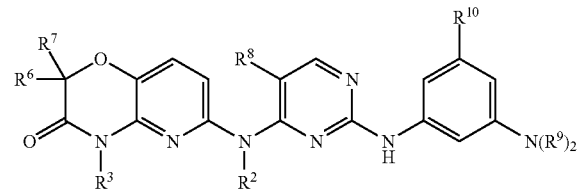

In a seventh embodiment, in accord with one of the first specific embodiment, the second, third or fourth embodiments, the compound is according to Formula V:

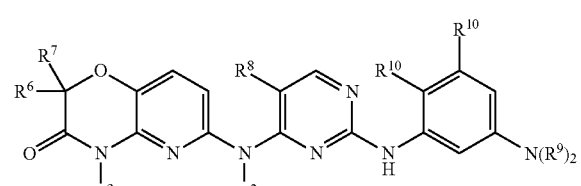

In an eighth embodiment, in accord with one of the first specific embodiment, the second, third or fourth embodiments, the compound is according to Formula VI:

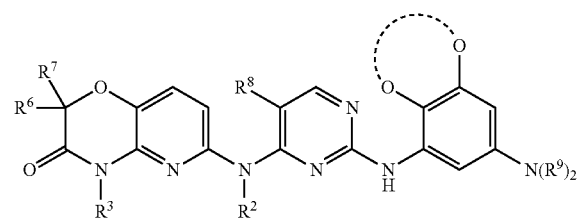

wherein the dashed line represents a bivalent linker, wherein the bivalent linker, together with the oxygens and annular carbon atoms to which the oxygens are bonded, forms a 5- to 8-membered cycloheteroalkyl ring.

In a ninth embodiment, in accord with one of the first specific embodiment, the second, third or fourth embodiments, the compound is according to Formula VII:

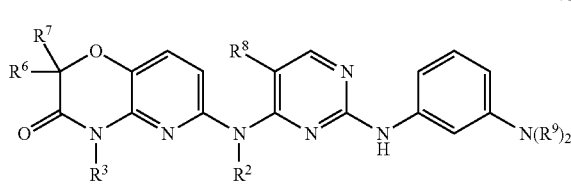

VII

In a tenth embodiment, in accord with one of the first specific embodiment, the second, third or fourth embodiments, the compound is according to one of the following formulae:

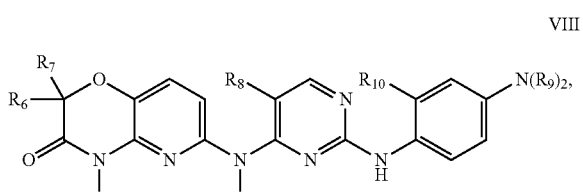

VIII

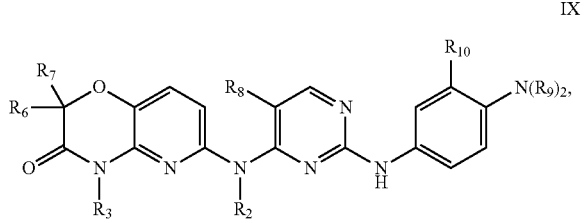

IX

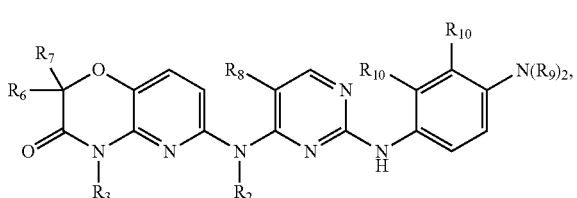

X

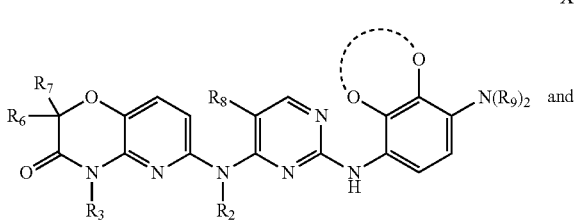

XI

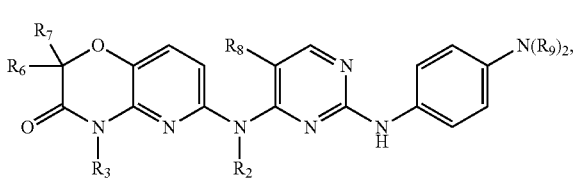

XII wherein the dashed line represents a bivalent linker, wherein the bivalent linker, together with the oxygens and annular carbon atoms to which the oxygens are bonded, forms a 5- to 8-membered cycloheteroalkyl ring.

In an eleventh embodiment, in accord with compounds of Formula I, compounds of the invention have a structure according to Formula XIII:

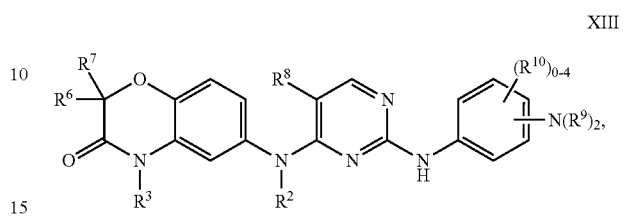

XIII wherein
two $R^9$ taken together with the nitrogen atom to which they are bonded form a 6- to 10-membered bridged bicyclic group optionally substituted with one or more of the same or different $R^{11}$, wherein the bridged bicyclic group contains at least two annular nitrogen atoms;
$R^{10}$ is as defined for compound I;
$R^8$ is H, (C1-C3) alkyl, (C1-C3) alkoxy, halogen, —CN, —NO$_2$, (C1-C3) haloalkyl, —C(O)OR$^d$ or (C1-C3) haloalkyloxy;
$R^2$ is H, (C1-C6) alkyl, (C3-C6) cycloalkyl or (C4-C6) cycloalkylalkyl;
$R^3$ is defined as for Formula I;
$R^6$ and $R^7$ are each, independently of one another, H, halo or (C1-C6) alkyl, or alternatively,
$R^6$ and $R^7$ are taken together with the carbon atom to which they are bonded to form an optionally substituted spirocycloalkyl or an optionally substituted spirocycloheteroalkyl.

In a twelfth embodiment, is a compound of Formula XIII where $R^2$ is H.

In a thirteenth embodiment, is a compound having a structure as in the eleventh or twelfth embodiment, where the bridged bicyclic group is

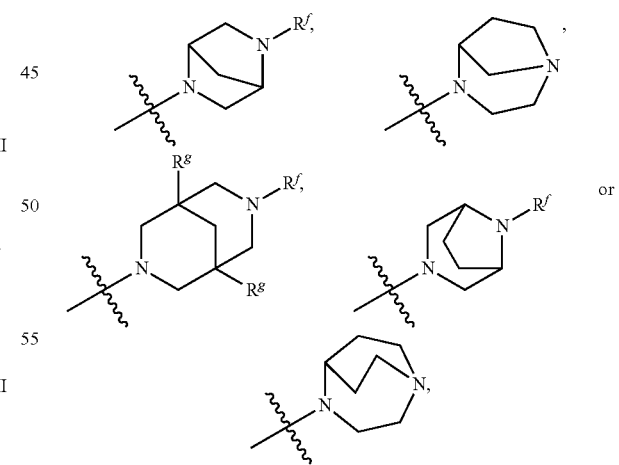

where $R^f$ is $R^a$, —S(O)$_2$R$^d$, —C(O)R$^d$, —C(O)OR$^d$ or —C(O)NR$^c$R$^c$; and each $R^g$ is independently H, halogen or (C1-C6) alkyl.

In a fourteenth embodiment, is provided a compound with a structure as in the thirteenth embodiment, where $R^f$ is H, (C1-C4) alkyl, (C4-C8) cycloalkylalkyl, —C(O)CH$_3$ or —SO$_2$CH$_3$; R$^{10}$ is halogen, haloalkyl, alkyl, cycloalkyl, cycloalkylalkyl, alkoxy or cycloalkylalkyloxy, or alternatively, two R$^{10}$ on vicinal carbons, taken together with the carbons to which they are bonded, form a ring fused to A which is a 5- to 8-membered cycloalkyl, a 5- to 8-membered cycloheteroalkyl, 5- to 6-membered aryl or a 5- to 6-membered heteroaryl, each optionally substituted with one or more of the same or different R$^{11}$ groups; R$^3$ is defined as for Formula I; R$^8$ is H, (C1-C3) alkyl, (C1-C3) perfluoroalkyl, fluoro, chloro or alkoxy; and R$^6$ and R$^7$ are each independently H, halogen, methyl or ethyl.

In a fifteenth embodiment, is provided a compound according to any one of the eleventh, twelfth, thirteenth and fourteenth embodiments having a structure according to Formula XIV:

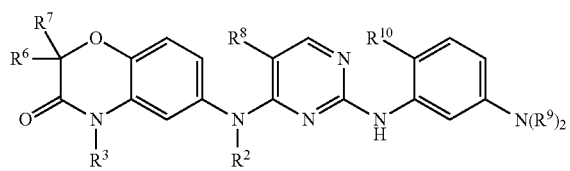

XIV

In a sixteenth embodiment, is provided a compound according to any one of the eleventh, twelfth, thirteenth and fourteenth embodiments having a structure according to Formula XV:

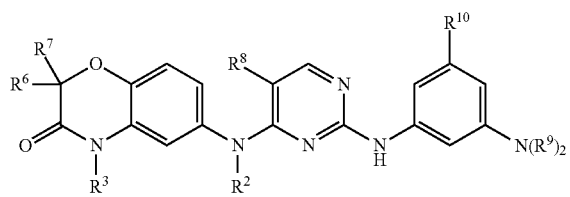

XV

In a seventeenth embodiment, is provided a compound according to any one of the eleventh, twelfth, thirteenth and fourteenth embodiments having a structure according to Formula XVI:

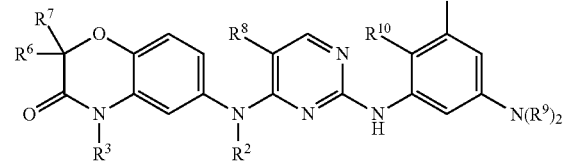

XVI

In an eighteenth embodiment, is provided a compound according to any one of the eleventh, twelfth, thirteenth and fourteenth embodiments having a structure according to Formula XVII:

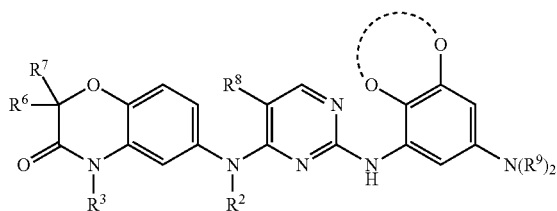

XVII where the dashed line represents a bivalent linker, where the bivalent linker, together with the oxygens and annular carbon atoms to which the oxygens are bonded, forms a 5-8 membered cyclohetero alkyl ring.

In a nineteenth embodiment, is provided a compound according to any one of the eleventh, twelfth, thirteenth and fourteenth embodiments having a structure according to Formula XVIII:

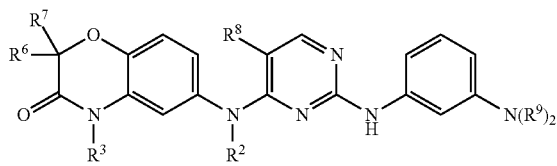

XVIII

In a twentieth embodiment, is provided a compound according to any one of the eleventh, twelfth, thirteenth and fourteenth embodiments having a structure according to one of the following formulae:

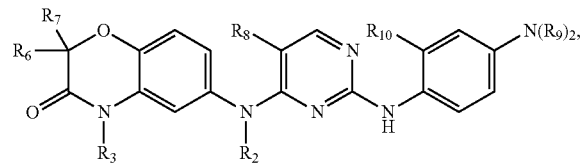

XIX

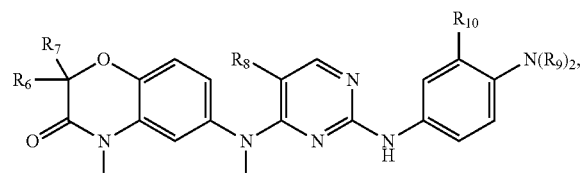

XX

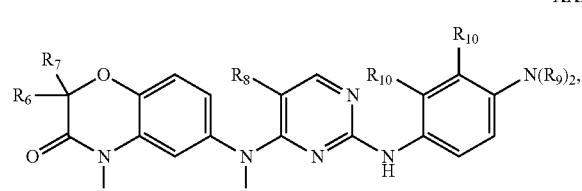

XXI

-continued

XII

XXIII where the dashed line represents a bivalent linker, wherein the bivalent linker, together with the oxygens and annular carbon atoms to which the oxygens are bonded, forms a 5- to 8-membered cycloheteroalkyl ring.

In a twenty-first embodiment, the compound of Formula I has a structure of Formula XXIV:

XXIV where two $R^9$ are taken together with the nitrogen atom to which they are bonded to form a 6- to 10-membered bridged bicyclic or a 6- to 12-membered bridged tricyclic group, each optionally substituted with one or more of the same or different $R^{11}$.

In a twenty-second embodiment, the compound of Formula I has a structure of Formula XXV:

XXV wherein two $R^9$ are taken together with the nitrogen atom to which they are bonded to form a 6- to 10-membered bridged bicyclic or a 6- to 12-membered bridged tricyclic group, each optionally substituted with one or more of the same or different $R^{11}$.

In a twenty-third embodiment, the compound of Formula I is according to one of the following formulae:

XXVI

XXVII

XXVIII and

XXIX wherein
$R^9$ and $R^{10}$ are defined as for Formula I;
$R^8$ is H, (C1-C3) alkyl, (C1-C3) alkoxy, halo, —CN, —NO$_2$, (C1-C3) haloalkyl, —C(O)OR$^d$ or (C1-C3) haloalkyloxy;
$R^2$ is H, (C1-C6) alkyl, (C3-C6) cycloalkyl or (C4-C6) cycloalkylalkyl;
$R^3$ is as defined for Formula I;
$R^6$ and $R^7$ are each, independently of one another, H, halo or (C1-C6) alkyl, or, alternatively,
$R^6$ and $R^7$ are taken together with the carbon atom to which they are bonded to form an optionally substituted spirocycloalkyl or an optionally substituted spirocycloheteroalkyl.

In a twenty-fourth embodiment, the compound is according to the twenty-third embodiment where $R^2$ is H.

In a twenty-fifth embodiment, is provided a compound according to any one of the twenty-third or twenty-fourth embodiment where the two $R^9$ groups are taken together with nitrogen to which the are bonded to form:

where $R^f$ is $R^a$, —S(O)$_2$R$^d$, —C(O)R$^d$, —C(O)OR$^d$ or —C(O)NR$^c$R$^c$.

In a twenty-sixth embodiment, is provided a compound of the twenty-fifth embodiment where $R^f$ is H, (C1-C4) alkyl, (C4-C8) cycloalkylalkyl, —C(O)CH$_3$ or —SO$_2$CH$_3$; $R^{10}$ is halogen, haloalkyl, alkyl, cycloalkyl, cycloalkylalkyl, alkoxy or cycloalkylalkyloxy, or alternatively, two $R^{10}$ on vicinal carbons, taken together with the carbons to which they are bonded, form a ring fused to phenyl or pyridyl which is a 5- to 8-membered cycloalkyl, a 5- to 8-membered cycloheteroalkyl, 5- to 6-membered aryl or a 5- to 6-membered heteroaryl, each optionally substituted with one or more of the same or different $R^{11}$ groups; $R^3$ is as defined for compound I; $R^8$ is H, C1-C3 alkyl, C1-C3 perfluoroalkyl, fluoro, chloro or alkoxy; and $R^6$ and $R^7$ are each independently H, halogen, methyl or ethyl.

In a twenty-seventh embodiment, the compounds of embodiment twenty-six, have at least one $R^{10}$ in an ortho position. The position is indicated with respect to N2 of the pyrimidinediamine system.

In a twenty-eighth embodiment, the compounds of embodiment twenty-seven have $-N(R^9)_2$ in a meta position. The position is indicated with respect to N2 of the pyrimidinediamine system.

In a twenty-ninth embodiment, the compounds of embodiment twenty-eighth have at least two $R^{10}$ groups attached to vicinal carbons at the ortho and meta positions.

In a thirtieth embodiment, the compounds of embodiment twenty-nine have the two $R^{10}$ groups which together with the vicinal annular carbons to which they are bonded form a ring fused to phenyl which is a 5- to 8-membered cycloalkyl, a 5- to 8-membered cycloheteroalkyl, a 5- to 6-membered aryl or a 5- to 6-membered heteroaryl, each optionally substituted with one or more of the same or different $R^{11}$ groups.

In a thirty-first embodiment, is a compound according to Formula I:

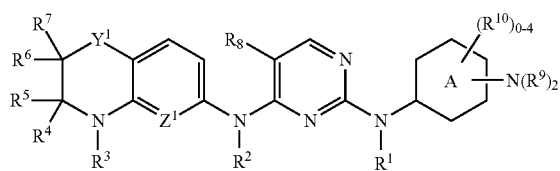

I or a pharmaceutically acceptable salt, a solvate, an N-oxide, or a prodrug thereof,
wherein:
$Y^1$ is O or S;
$Z^1$ is CH or N;
A is phenyl or a 6-membered heteroaryl;
$R^1$ is H;
$R^2$ and $R^3$ are each, independently of one another, H, (C1-C6) alkyl optionally substituted with one or more of the same or different $R^{11}$ groups, (C3-C8) cycloalkyl optionally substituted with one or more of the same or different $R^{11}$ groups, (C4-C11) cycloalkylalkyl optionally substituted with one or more of the same or different $R^{11}$ groups, (C5-C10) aryl optionally substituted with one or more of the same or different $R^{11}$ groups, (C6-C16) arylalkyl optionally substituted with one or more of the same or different $R^{11}$ groups, 2-6 membered heteroalkyl optionally substituted with one or more of the same or different $R^{11}$ groups, 3-8 membered cycloheteroalkyl, optionally substituted with one or more of the same or different $R^{11}$ groups, 4-11 membered cycloheteroalkylalkyl, optionally substituted with one or more of the same or different $R^{11}$ groups, 5-10 membered heteroaryl optionally substituted with one or more of the same or different $R^{11}$ groups, and 6-16 membered heteroarylalkyl optionally substituted with one or more of the same or different RU groups;

$R^4$ and $R^5$ are each, independently of one another, selected from the group consisting of H, (C1-C6) alkyl, (C1-C6) haloalkyl, (C1-C6) alkoxy, halogen, (C1-C6) haloalkoxy, (C1-C6) aminoalkyl and (C1-C6) hydroxyalkyl, or, alternatively, $R^4$ and $R^5$, taken together with the carbon atom to which they are bonded, form a spirocycloalkyl or a spirocycloheteroalkyl, or, alternatively, $R^4$ and $R^5$, taken together with the carbon atom to which they are bonded, form a C=O group;

$R^6$ and $R^7$ are each, independently of one another, selected from the group consisting of H, (C1-C6) alkyl, (C1-C6) haloalkyl, (C1-C6) alkoxy, halogen, (C1-C6) haloalkoxy, (C1-C6) aminoalkyl and (C1-C6) hydroxyalkyl, or, alternatively, $R^6$ and $R^7$, taken together with the carbon atom to which they are bonded, form a spirocycloalkyl or a spirocycloheteroalkyl or, alternatively, $R^6$ and $R^7$, taken together with the carbon atom to which they are bonded, form a C=O group;

$R^8$ is selected from the group consisting of H, halo, (C1-C6) alkyl optionally substituted with one or more of the same or different $R^{11}$ groups, (C1-C3) haloalkyloxy, $-OR^d$, $-SR^d$, $-NR^cR^c$, (C1-C3) haloalkyl, $-C(O)OR^d$, $-CN$, $-NC$, $-OCN$, $-SCN$, $-NO$, and $-NO_2$;

two $R^9$, taken together with the nitrogen atom to which they are bonded, form a 6- to 10-membered bridged bicyclic cycloheteroalkyl, which may be optionally substituted with one or more of the same or different $R^{11}$ groups, and wherein the substituted or unsubstituted bicyclic cycloheteroalkyl includes at least two nitrogen atoms;

each $R^{10}$ is independently $R^{11}$ or alternatively, two $R^{10}$ on vicinal carbons, taken together with the carbons to which they are bonded, form a ring fused to A selected from the group consisting of a 5- to 8-membered cycloalkyl, a 5- to 8-membered cycloheteroalkyl, 5- to 6-membered aryl and a 5- to 6-membered heteroaryl, each optionally substituted with one or more of the same or different $R^{11}$ groups;

each $R^{11}$ independently is $R^e$, $R^b$, $R^e$ substituted with one or more of the same or different $R^a$ or $R^b$, $-OR^a$ substituted with one or more of the same or different $R^a$ or $R^b$, $-B(OR^a)_2$, $-B(NR^cR^c)_2$, $-(CH_2)_m-R^b$, $-(CHR^a)_m-R^b$, $-O-(CH_2)_m-R^b$, $-S-(CH_2)_m-R^b$, $-O-CHR^aR^b$, $O-CR^a(R^b)_2$, $-O-(CHR^a)_m-R^b$, $-O-(CH_2)_m-CH[(CH_2)_mR_b]R_b$, $-S-(CHR^a)^b-R^b$, $-C(O)NH-(CH_2)_m-R^b$, $-C(O)NH-(CHR^a)_m-R^b$, $-O-(CH_2)_m-C(O)NH-(CH_2)_m-R^b$, $-S-(CH_2)_mC(O)NH-(CH_2)_m-R^b$, $-O-(CHR_a)_m-C(O)NH-(CHR_a)_m-R^b$, $-S-(CHR^a)_m-C(O)NH-(CHR^a)_m-R^b$, $-NH-(CH_2)_m-R^b$, $-NH-(CHR^a)_m-R^b$, $-N[(CH_2)_mR^b]_2$, $-NH-C(O)-NH-(CH_2)_m-R^b$, $-NH-C(O)-(CH_2)_m-CHR^bR^b$ and $-NH-(CH_2)_m-C(O)-NH(CH_2)_m-R^b$;

each $R^a$ is independently selected from the group consisting of hydrogen, (C1-C6) alkyl, (C3-C8) cycloalkyl, (C4-C11) cycloalkylalkyl, (C5-C10) aryl, (C6-C16) arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;

each $R^b$ is independently selected from the group consisting of =O, $OR^d$, (C1-C3) haloalkyloxy, $-OCF_3$, =S, $-SR^d$, =$NR^d$, =$NOR^d$, $NR^cR^c$, halogen, haloalkyl, $-CN$, $-NC$, $-OCN$, $-SCN$, $-NO$, $-NO_2$, =$N_2$, $-N_3$, $-S(O)R^d$, $-S(O)_2R^d$, $S(O)_2OR^d$, $-S(O)NR^cR^c$; $-S(O)_2NR^cR^c$, $-OS(O)R^d$, $-OS(O)_2R^c$, $-OS(O)_2OR^d$, $-OS(O)NR^cR^c$, $-OS(O)_2NR^cR^c$, $-C(O)R^d$, $-C(O)OR^d$, $-C(O)NR^cR^c$, $-C(NH)NR^cR^c$, $-OC(O)R^d$, $-SC(O)R^d$, $-OC(O)OR^d$, $-SC(O)OR^d$, $-OC(O)NR^cR^c$, $-SC(O)NR^cR^c$, $-OC(NH)$ NR$^c$R$^c$, —SC(NH)NR$^c$R$^c$, —[NHC(O)]$_n$R$^d$, —[NHC(O)]$_n$OR$^d$, —[NHC(O)]$_n$NR$^c$R$^c$, —[NHC(NH)]$_n$NR$^c$R$^c$ and —[NR$^a$C(NR$^a$)]$_n$NR$^c$R$^c$;

each R$^c$ is independently R$^a$, or, alternatively, two R$^c$ are taken together with the nitrogen atom to which they are bonded to form a 5 to 8-membered cycloheteroalkyl or heteroaryl, optionally including one or more of the same or different additional annular heteroatoms and optionally substituted with one or more of the same or different R$^a$ or R$^b$ groups;

each R$^d$ is independently R$^a$;

each R$^e$ is independently selected from the group consisting of (C1-C6) alkyl, (C3-C8) cycloalkyl, (C4-C11) cycloalkylalkyl, (C5-C10) aryl, (C6-C16) arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;

each m is independently an integer from 1 to 3; and
each n is independently an integer from 0 to 3.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamines that include ester moieties may be considered prodrugs of their corresponding carboxylic acid, regardless of whether the ester form is pharmacologically active.

In the prodrugs described herein, any available functional moiety may be masked with a progroup to yield a prodrug. Functional groups within the 2,4-pyrimidinediamine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

Additional exemplary embodiments of the compounds described herein are illustrated in the following Table 1, below. Table 1 lists pyrimidinediamine compounds that have been prepared, as well as PLK1 inhibition assay data for some of the compounds.

In some embodiments, the compounds have an IC$_{50}$ as against PLK1 of less than 10 µM, some less than 5 µM, some less than 1 µM, some less than 0.1 µM, and some less than 0.01 µM with reference to a biochemical or cellular assay.

In some embodiments, compounds having an IC$_{50}$ of less than 10 µM in a biochemical in vitro PLK1 assay are compounds Nos. 3, 4-6, 15-21, 23-30, 32-56, 95-97, 101, 107-111, 114-116, 120, 122, 125, 127-134, 157, 161, 167-169, 173, 183, 188, 189, 191 and 196 presented in Table 1.

The results of the ability of the compounds described herein to inhibit PLK1 activity, when tested under conditions herein, are shown in Table 1, where the activity is indicated by the following ranges: "A" represents compounds having an IC$_{50}$<0.5 µM; "B" represents compounds having an IC$_{50}$≥0.5 µM and <5 µM; "C" represents compounds having an IC$_{50}$≥5 µM and <10 µM; and "D" represents compounds having activity ≥10 µM.

TABLE 1

| # | Structure | Name | PLK1 IC$_{50}$ (µM) biochemical assay | PLK1 IC$_{50}$ (µM) cellular assay |
| --- | --- | --- | --- | --- |
| 1 | 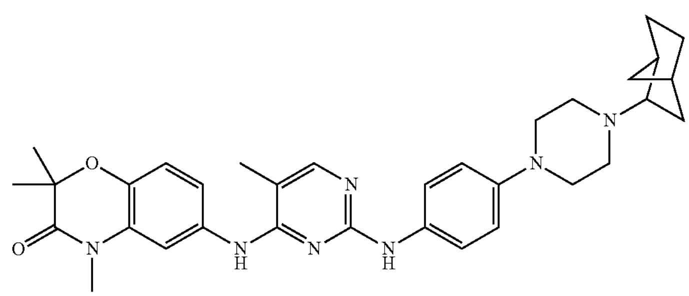 [SMILES: Cc1cnc(Nc2ccc(N3CCN(C4CC5CCC4C5)CC3)cc2)nc1Nc1ccc2c(c1)N(C)C(=O)C(C)(C)O2] | 6-(2-(4-(4-(bicyclo[2.2.1]heptan-2-yl)piperazin-1-yl)phenylamino)-5-methyl-pyrimidin-4-ylamino)-2,2,4-trimethyl-2H-benzo[b][1,4]oxazin-3(4H)-one | | |
| 2 | 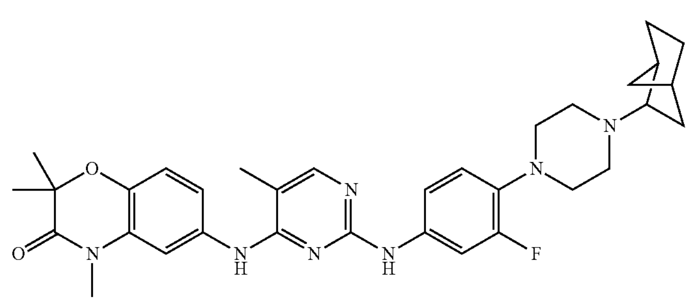 [SMILES: Cc1cnc(Nc2ccc(N3CCN(C4CC5CCC4C5)CC3)c(F)c2)nc1Nc1ccc2c(c1)N(C)C(=O)C(C)(C)O2] | 6-(2-(4-(4-(bicyclo[2.2.1]heptan-2-yl)piperazin-1-yl)-3-fluorophenylamino)-5-methylpyrimidin-4-ylamino)-2,2,4-trimethyl-2H-benzo[b][1,4]oxazin-3(4H)-one | | |

TABLE 1-continued

| # | Structure | Name | PLK1 IC$_{50}$ (µM) biochemical assay | PLK1 IC$_{50}$ (µM) cellular assay |
|---|-----------|------|---|---|
| 3 | 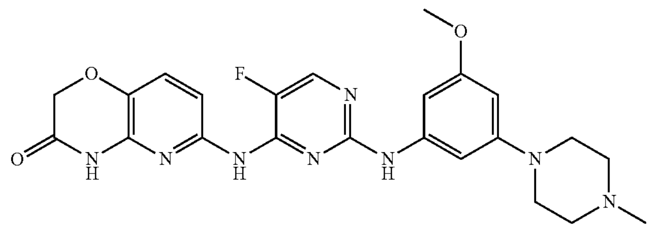 [SMILES: COc1cc(Nc2ncc(F)c(Nc3ccc4c(n3)NC(=O)CO4)n2)cc(N2CCN(C)CC2)c1] | 6-(5-fluoro-2-(3-methoxy-5-(4-methylpiperazin-1-yl)phenylamino)pyrimidin-4-ylamino)-2H-pyrido[3,2-b][1,4]oxazin-3(4H)-one | A | |
| 4 | 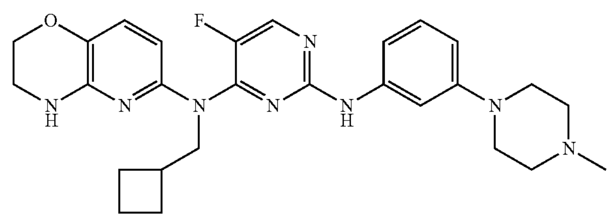 [SMILES: CN1CCN(c2cccc(Nc3ncc(F)c(N(CC4CCC4)c4ccc5c(n4)NCCO5)n3)c2)CC1] | N4-(cyclobutylmethyl)-N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | C | |
| 5 | 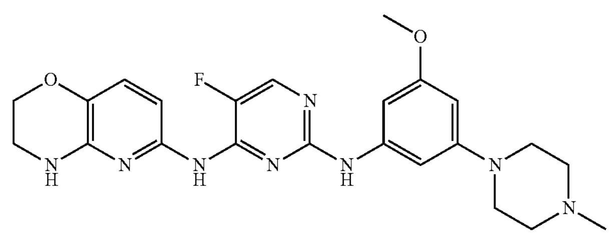 [SMILES: COc1cc(Nc2ncc(F)c(Nc3ccc4c(n3)NCCO4)n2)cc(N2CCN(C)CC2)c1] | N4-(3,4-dihydro-2H-pyrido[3,2-b][1,4]oxazin-6-yl)-5-fluoro-N2-(3-methoxy-5-(4-methylpiperazin-1-yl)phenyl)pyrimidine-2,4-diamine | A | |
| 6 | 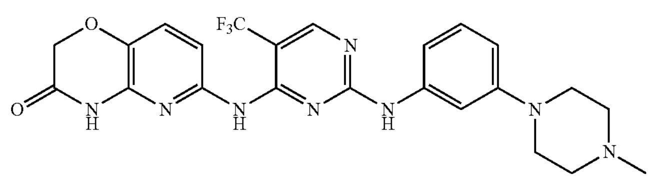 [SMILES: CN1CCN(c2cccc(Nc3ncc(C(F)(F)F)c(Nc4ccc5c(n4)NC(=O)CO5)n3)c2)CC1] | 6-(2-(3-(4-methylpiperazin-1-yl)phenylamino)-5-(trifluoromethyl)pyrimidin-4-ylamino)-2H-pyrido[3,2-b][1,4]oxazin-3(4H)-one | A | |
| 7 | 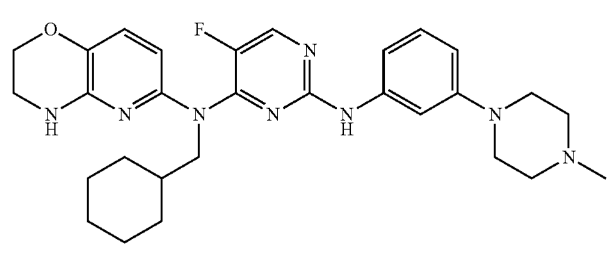 [SMILES: CN1CCN(c2cccc(Nc3ncc(F)c(N(CC4CCCCC4)c4ccc5c(n4)NCCO5)n3)c2)CC1] | N4-(cyclohexylmethyl)-N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | D | |
| 8 | 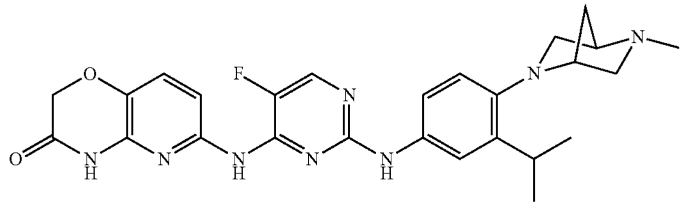 [SMILES: CC(C)c1cc(Nc2ncc(F)c(Nc3ccc4c(n3)NC(=O)CO4)n2)ccc1N1CC2CC1CN2C] | 6-(5-fluoro-2-(3-isopropyl-4-(5-methyl-2,5-diazabicyclo[2.2.1]heptan-2-yl)phenylamino)pyrimidin-4-ylamino)-2H-pyrido[3,2-b][1,4]oxazin-3(4H)-one | D | |

TABLE 1-continued

| # | Structure | Name | PLK1 IC$_{50}$ (μM) biochemical assay | PLK1 IC$_{50}$ (μM) cellular assay |
|---|---|---|---|---|
| 9 | 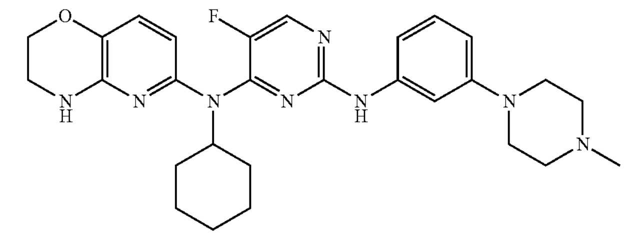 [SMILES: CN1CCN(c2cccc(Nc3ncc(F)c(N(c4ccc5c(n4)NCCO5)C4CCCCC4)n3)c2)CC1] | N4-cyclohexyl-N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | D | |
| 10 | 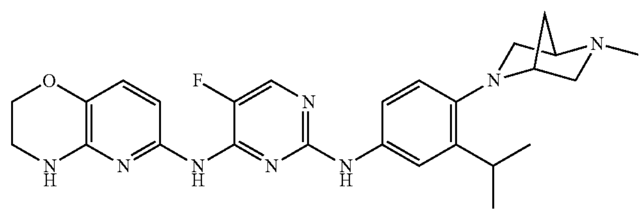 [SMILES: CC(C)c1cc(Nc2ncc(F)c(Nc3ccc4c(n3)NCCO4)n2)ccc1N1CC2CC1CN2C] | N4-(3,4-dihydro-2H-pyrido[3,2-b][1,4]oxazin-6-yl)-5-fluoro-N2-(3-isopropyl-4-(5-methyl-2,5-diazabicyclo[2.2.1]heptan-2-yl)phenyl)pyrimidine-2,4-diamine | D | |
| 11 | 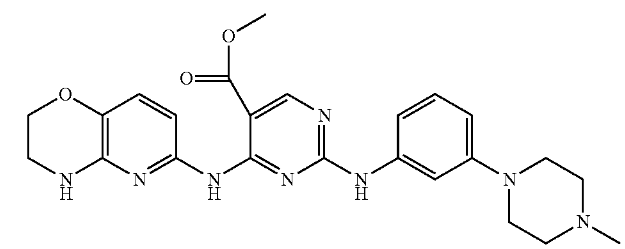 [SMILES: COC(=O)c1cnc(Nc2cccc(N3CCN(C)CC3)c2)nc1Nc1ccc2c(n1)NCCO2] | methyl 4-(3,4-dihydro-2H-pyrido[3,2-b][1,4]oxazin-6-ylamino)-2-(3-(4-methylpiperazin-1-yl)phenylamino)pyrimidine-5-carboxylate | D | |
| 12 | 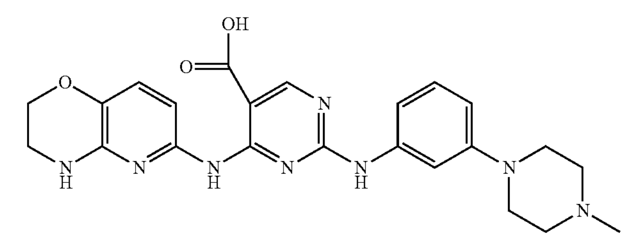 [SMILES: CN1CCN(c2cccc(Nc3ncc(C(=O)O)c(Nc4ccc5c(n4)NCCO5)n3)c2)CC1] | 4-(3,4-dihydro-2H-pyrido[3,2-b][1,4]oxazin-6-ylamino)-2-(3-(4-methyl-piperazin-1-yl)phenyl-amino)pyrimidine-5-carboxylic acid | D | |
| 13 | 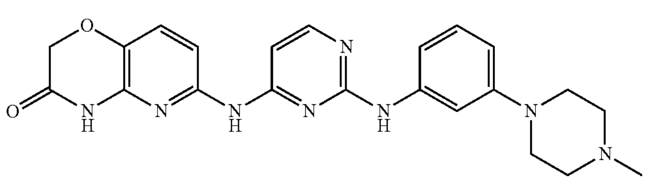 [SMILES: CN1CCN(c2cccc(Nc3nccc(Nc4ccc5c(n4)NC(=O)CO5)n3)c2)CC1] | 6-(2-(3-(4-methylpiperazin-1-yl)phenylamino)pyrimidin-4-ylamino)-2H-pyrido[3,2-b][1,4]oxazin-3(4H)-one | D | |
| 14 | 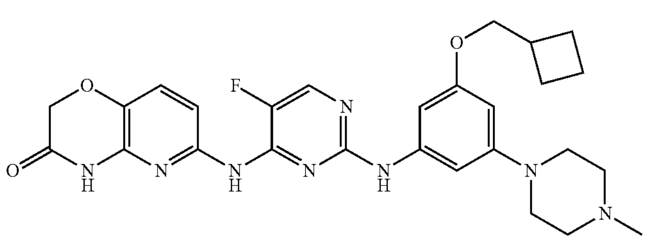 [SMILES: CN1CCN(c2cc(Nc3ncc(F)c(Nc4ccc5c(n4)NC(=O)CO5)n3)cc(OCC3CCC3)c2)CC1] | 6-(2-(3-(cyclobutylmethoxy)-5-(4-methylpiperazin-1-yl)phenylamino)-5-fluoropyrimidin-4-ylamino)-2H-pyrido[3,2-b][1,4]oxazin-3(4H)-one | D | |

TABLE 1-continued

| # | Structure | Name | PLK1 IC$_{50}$ (μM) biochemical assay | PLK1 IC$_{50}$ (μM) cellular assay |
|---|---|---|---|---|
| 15 | 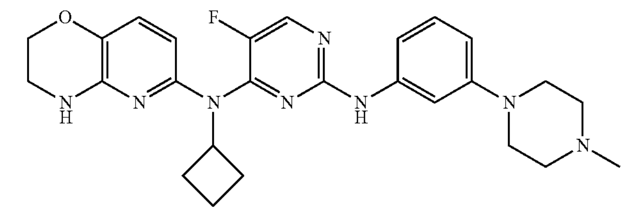 [SMILES: CN1CCN(c2cccc(Nc3ncc(F)c(N(c4ccc5c(n4)NCCO5)C4CCC4)n3)c2)CC1] | N4-cyclobutyl-N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | B | |
| 16 | 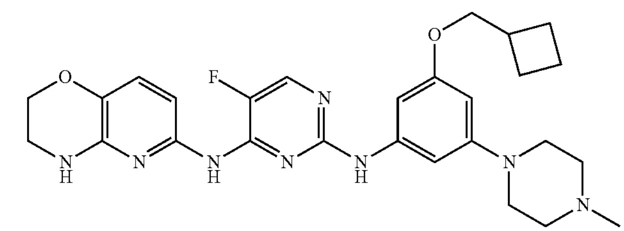 [SMILES: CN1CCN(c2cc(Nc3ncc(F)c(Nc4ccc5c(n4)NCCO5)n3)cc(OCC3CCC3)c2)CC1] | N2-(3-(cyclobutylmethoxy)-5-(4-methylpiperazin-1-yl)phenyl)-N4-(3,4-dihydro-2H-pyrido[3,2-b][1,4]oxazin-6-yl)-5-fluoropyrimidine-2,4-diamine | A | |
| 17 | 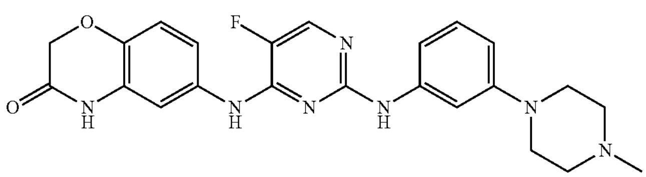 [SMILES: CN1CCN(c2cccc(Nc3ncc(F)c(Nc4ccc5c(c4)NC(=O)CO5)n3)c2)CC1] | 6-(5-fluoro-2-(3-(4-methylpiperazin-1-yl)phenylamino)pyrimidin-4-ylamino)-2H-benzo[b][1,4]oxazin-3(4H)-one | A | B |
| 18 | 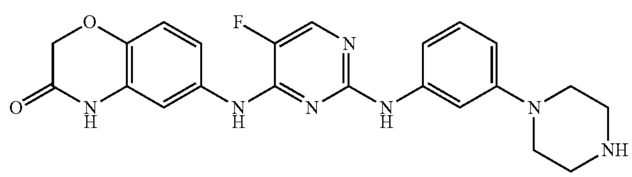 [SMILES: O=C1COc2ccc(Nc3nc(Nc4cccc(N5CCNCC5)c4)ncc3F)cc2N1] | 6-(5-fluoro-2-(3-(piperazin-1-yl)phenylamino)pyrimidin-4-ylamino)-2H-benzo[b][1,4]oxazin-3(4H)-one | A | B |
| 19 | HCl salt | 6-(5-fluoro-2-(3-(4-methylpiperazin-1-yl)phenylamino)pyrimidin-4-ylamino)-2H-pyrido[3,2-b][1,4]oxazin-3(4H)-one hydrochloride | A | A |
| 20 | 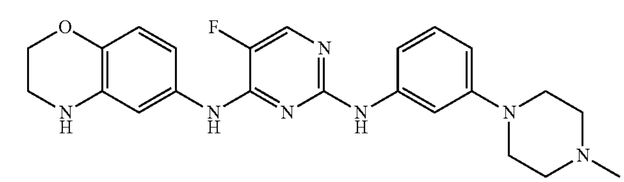 | N4-(3,4-dihydro-2H-benzo[b][1,4]oxazin-6-yl)-5-fluoro-N2-(3-(4-methylpiperazin-1-yl)phenyl)pyrimidine-2,4-diamine | A | B |
| 21 | 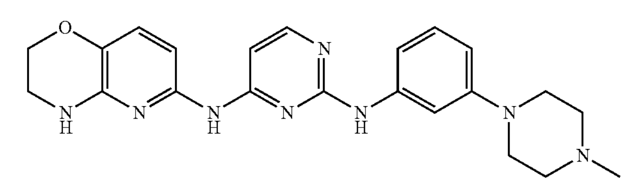 [SMILES: CN1CCN(c2cccc(Nc3nccc(Nc4ccc5c(n4)NCCO5)n3)c2)CC1] | N4-(3,4-dihydro-2H-pyrido[3,2-b][1,4]oxazin-6-yl)-N2-(3-(4-methylpiperazin-1-yl)phenyl)pyrimidine-2,4-diamine | A | D |

TABLE 1-continued

| # | Structure | Name | PLK1 IC$_{50}$ (μM) biochemical assay | PLK1 IC$_{50}$ (μM) cellular assay |
|---|---|---|---|---|
| 22 | 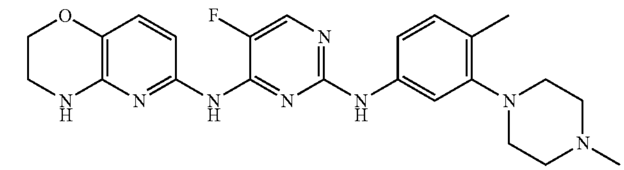 [SMILES: Cc1ccc(Nc2ncc(F)c(Nc3ccc4c(n3)NCCO4)n2)cc1N1CCN(C)CC1] | N4-(3,4-dihydro-2H-pyrido[3,2-b][1,4]oxazin-6-yl)-5-fluoro-N2-(4-methyl-3-(4-methylpiperazin-1-yl)phenyl)pyrimidine-2,4-diamine | D | D |
| 23 | 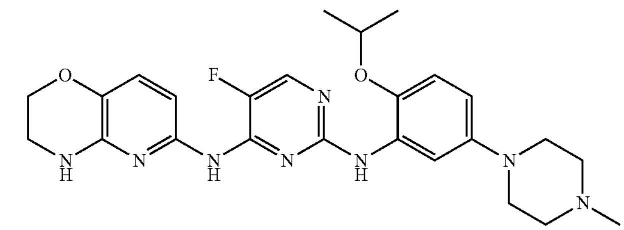 [SMILES: CC(C)Oc1ccc(N2CCN(C)CC2)cc1Nc1ncc(F)c(Nc2ccc3c(n2)NCCO3)n1] | N4-(3,4-dihydro-2H-pyrido[3,2-b][1,4]oxazin-6-yl)-5-fluoro-N2-(2-isopropoxy-5-(4-methylpiperazin-1-yl)phenyl)pyrimidine-2,4-diamine | A | B |
| 24 | 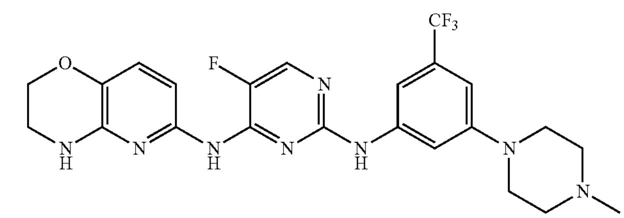 [SMILES: CN1CCN(c2cc(Nc3ncc(F)c(Nc4ccc5c(n4)NCCO5)n3)cc(C(F)(F)F)c2)CC1] | N4-(3,4-dihydro-2H-pyrido[3,2-b][1,4]oxazin-6-yl)-5-fluoro-N2-(3-(4-methylpiperazin-1-yl)-5-(trifluoromethyl)phenyl)pyrimidine-2,4-diamine | A | D |
| 25 | 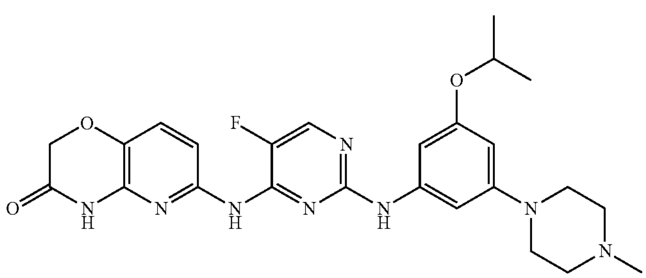 [SMILES: CC(C)Oc1cc(Nc2ncc(F)c(Nc3ccc4c(n3)NC(=O)CO4)n2)cc(N2CCN(C)CC2)c1] | 6-(5-fluoro-2-(3-isopropoxy-5-(4-methylpiperazin-1-yl)phenylamino)pyrimidin-4-ylamino)-2H-pyrido[3,2-b][1,4]oxazin-3(4H)-one | A | A |
| 26 | 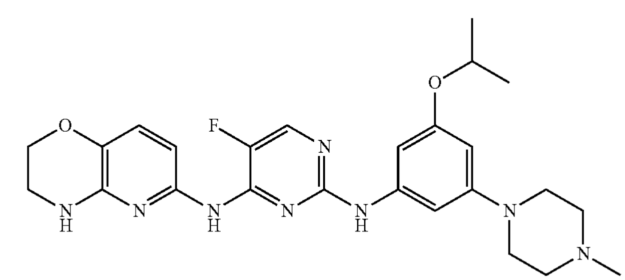 [SMILES: CC(C)Oc1cc(Nc2ncc(F)c(Nc3ccc4c(n3)NCCO4)n2)cc(N2CCN(C)CC2)c1] | N4-(3,4-dihydro-2H-pyrido[3,2-b][1,4]oxazin-6-yl)-5-fluoro-N2-(3-isopropoxy-5-(4-methylpiperazin-1-yl)phenyl)pyrimidine-2,4-diamine | A | A |
| 27 | 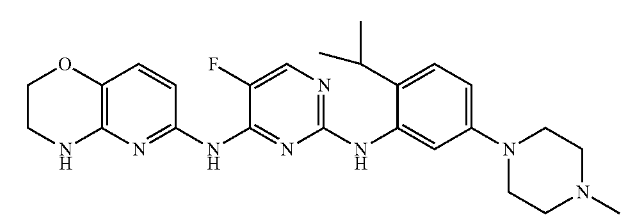 [SMILES: CC(C)c1ccc(N2CCN(C)CC2)cc1Nc1ncc(F)c(Nc2ccc3c(n2)NCCO3)n1] | N4-(3,4-dihydro-2H-pyrido[3,2-b][1,4]oxazin-6-yl)-5-fluoro-N2-(2-isopropyl-5-(4-methylpiperazin-1-yl)phenyl)pyrimidine-2,4-diamine | A | B |

TABLE 1-continued

| # | Structure | Name | PLK1 IC$_{50}$ (μM) biochemical assay | PLK1 IC$_{50}$ (μM) cellular assay |
|---|---|---|---|---|
| 28 | 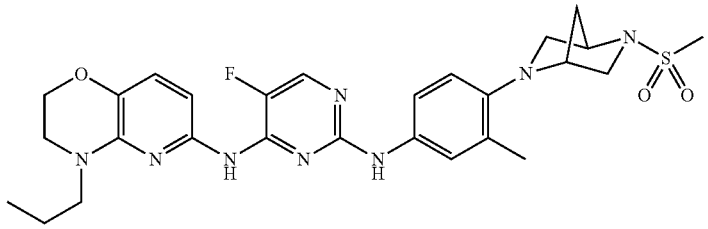 [SMILES: CCCN1CCOc2ccc(Nc3nc(Nc4ccc(N5CC6CC5CN6S(C)(=O)=O)c(C)c4)ncc3F)nc21] | 5-fluoro-N2-(3-methyl-4-(5-(methylsulfonyl)-2,5-diazabicyclo[2.2.1]heptan-2-yl)phenyl)-N4-(4-propyl-3,4-dihydro-2H-pyrido[3,2-b][1,4]oxazin-6-yl)pyrimidine-2,4-diamine | B | B |
| 29 | 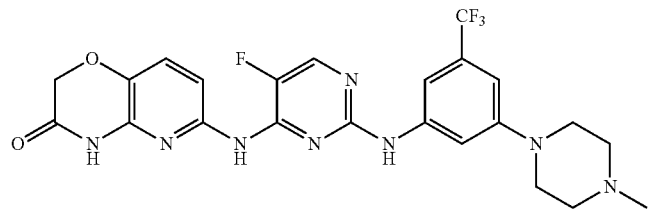 [SMILES: CN1CCN(c2cc(Nc3ncc(F)c(Nc4ccc5c(n4)NC(=O)CO5)n3)cc(C(F)(F)F)c2)CC1] | 6-(5-fluoro-2-(3-(4-methylpiperazin-1-yl)-5-(trifluoromethyl)phenylamino)pyrimidin-4-ylamino)-2H-pyrido[3,2-b][1,4]oxazin-3(4H)-one | A | D |
| 30 | 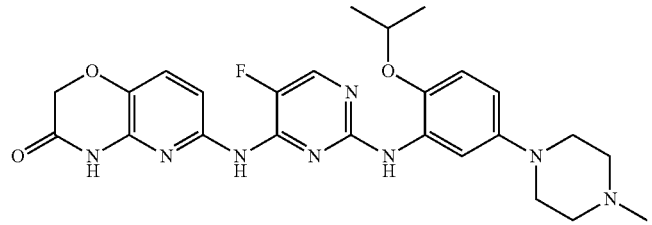 [SMILES: CC(C)Oc1ccc(N2CCN(C)CC2)cc1Nc1ncc(F)c(Nc2ccc3c(n2)NC(=O)CO3)n1] | 6-(5-fluoro-2-(2-isopropoxy-5-(4-methylpiperazin-1-yl)phenylamino)pyrimidin-4-ylamino)-2H-pyrido[3,2-b][1,4]oxazin-3(4H)-one | A | A |
| 31 | 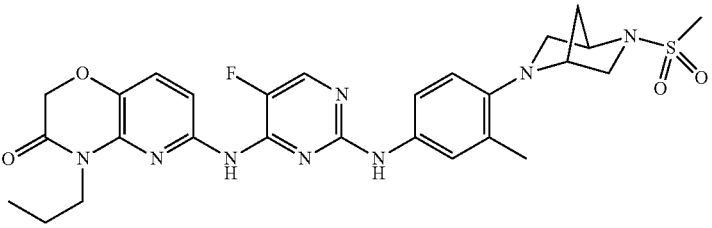 [SMILES: CCCN1C(=O)COc2ccc(Nc3nc(Nc4ccc(N5CC6CC5CN6S(C)(=O)=O)c(C)c4)ncc3F)nc21] | 6-(5-fluoro-2-(3-methyl-4-(5-(methylsulfonyl)-2,5-diazabicyclo[2.2.1]heptan-2-yl)phenylamino)pyrimidin-4-ylamino)-4-propyl-2H-pyrido[3,2-b][1,4]oxazin-3(4H)-one | D | B |
| 32 | 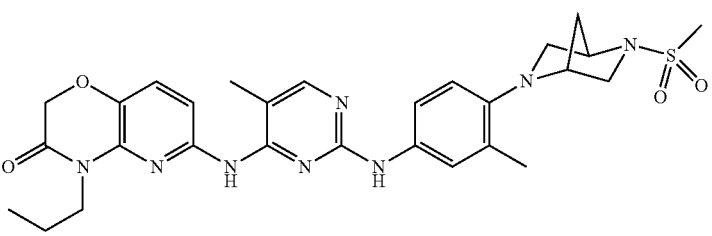 [SMILES: CCCN1C(=O)COc2ccc(Nc3nc(Nc4ccc(N5CC6CC5CN6S(C)(=O)=O)c(C)c4)ncc3C)nc21] | 6-(5-methyl-2-(3-methyl-4-(5-(methylsulfonyl)-2,5-diazabicyclo[2.2.1]heptan-2-yl)phenylamino)pyrimidin-4-ylamino)-4-propyl-2H-pyrido[3,2-b][1,4]oxazin-3(4H)-one | B | B |
| 33 | 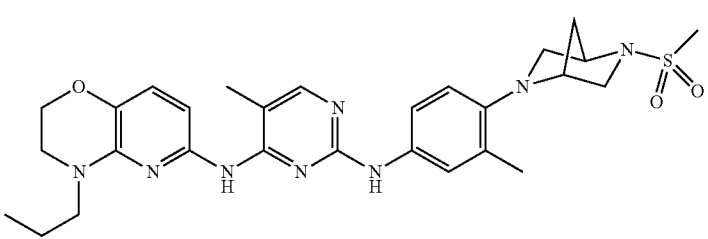 [SMILES: CCCN1CCOc2ccc(Nc3nc(Nc4ccc(N5CC6CC5CN6S(C)(=O)=O)c(C)c4)ncc3C)nc21] | 5-methyl-N2-(3-methyl-4-(5-(methylsulfonyl)-2,5-diazabicyclo[2.2.1]heptan-2-yl)phenyl)-N4-(4-propyl-3,4-dihydro-2H-pyrido[3,2-b][1,4]oxazin-6-yl)pyrimidine-2,4-diamine | A | B |

TABLE 1-continued

| # | Structure | Name | PLK1 IC$_{50}$ (μM) biochemical assay | PLK1 IC$_{50}$ (μM) cellular assay |
|---|---|---|---|---|
| 34 | 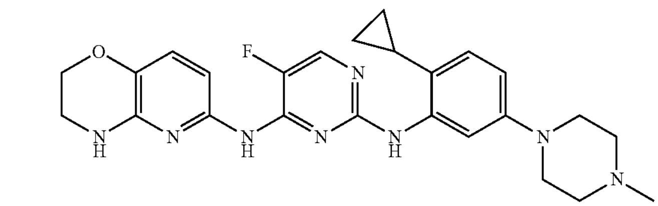 [SMILES: CN1CCN(c2ccc(C3CC3)c(Nc3ncc(F)c(Nc4ccc5c(n4)NCCO5)n3)c2)CC1] | N2-(2-cyclopropyl-5-(4-methylpiperazin-1-yl)phenyl)-N4-(3,4-dihydro-2H-pyrido[3,2-b][1,4]oxazin-6-yl)-5-fluoropyrimidine-2,4-diamine | A | A |
| 35 | 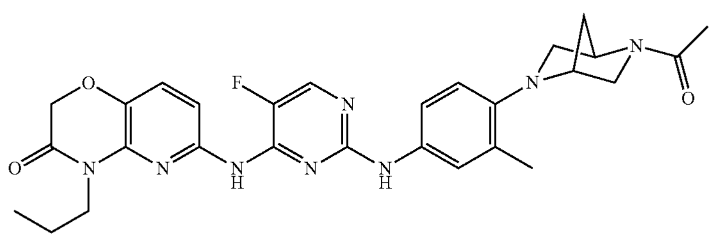 [SMILES: CCCN1C(=O)COc2ccc(Nc3nc(Nc4ccc(N5CC6CC5CN6C(C)=O)c(C)c4)ncc3F)nc21] | 6-(2-(4-(5-acetyl-2,5-diazabicyclo[2.2.1]heptan-2-yl)-3-methylphenylamino)-5-fluoropyrimidin-4-ylamino)-4-propyl-2H-pyrido[3,2-b][1,4]oxazin-3(4H)-one | A | B |
| 36 | 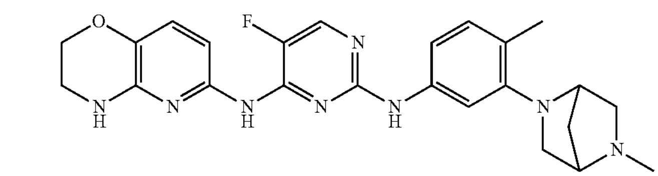 [SMILES: Cc1ccc(Nc2ncc(F)c(Nc3ccc4c(n3)NCCO4)n2)cc1N1CC2CC1CN2C] | N4-(3,4-dihydro-2H-pyrido[3,2-b][1,4]oxazin-6-yl)-5-fluoro-N2-(4-methyl-3-(5-methyl-2,5-diazabicyclo[2.2.1]heptan-2-yl)phenyl)pyrimidine-2,4-diamine | A | B |
| 37 | 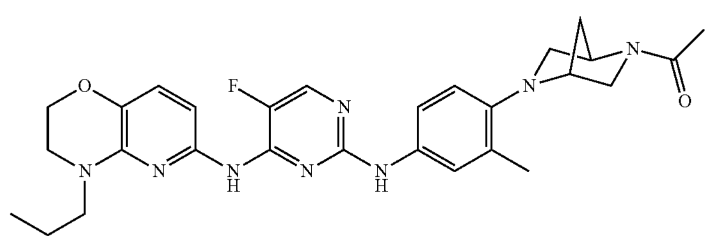 [SMILES: CCCN1CCOc2ccc(Nc3nc(Nc4ccc(N5CC6CC5CN6C(C)=O)c(C)c4)ncc3F)nc21] | 1-(5-(4-(5-fluoro-4-(4-propyl-3,4-dihydro-2H-pyrido[3,2-b][1,4]oxazin-6-ylamino)pyrimidin-2-ylamino)-2-methylphenyl)-2,5-diazabicyclo[2.2.1]heptan-2-yl)ethanone | B | B |
| 38 | 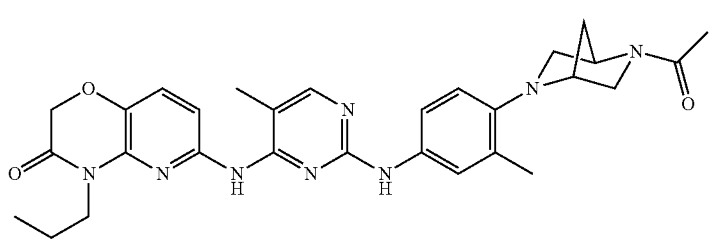 [SMILES: CCCN1C(=O)COc2ccc(Nc3nc(Nc4ccc(N5CC6CC5CN6C(C)=O)c(C)c4)ncc3C)nc21] | 6-(2-(4-(5-acetyl-2,5-diazabicyclo[2.2.1]heptan-2-yl)-3-methylphenylamino)-5-methylpyrimidin-4-ylamino)-4-propyl-2H-pyrido[3,2-b][1,4]oxazin-3(4H)-one | A | B |
| 39 | 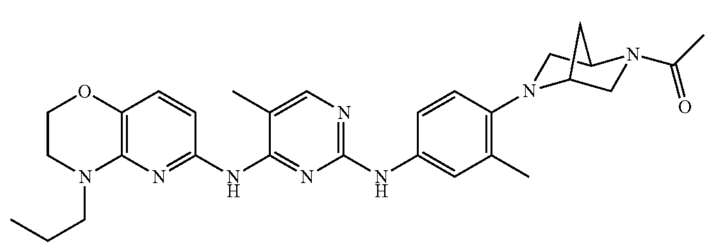 [SMILES: CCCN1CCOc2ccc(Nc3nc(Nc4ccc(N5CC6CC5CN6C(C)=O)c(C)c4)ncc3C)nc21] | 1-(5-(2-methyl-4-(5-methyl-4-(4-propyl-3,4-dihydro-2H-pyrido[3,2-b][1,4]oxazin-6-ylamino)pyrimidin-2-ylamino)phenyl)-2,5-diazabicyclo[2.2.1]heptan-2-yl)ethanone | B | B |

TABLE 1-continued

| # | Structure | Name | PLK1 IC$_{50}$ (μM) biochemical assay | PLK1 IC$_{50}$ (μM) cellular assay |
|---|---|---|---|---|
| 40 | 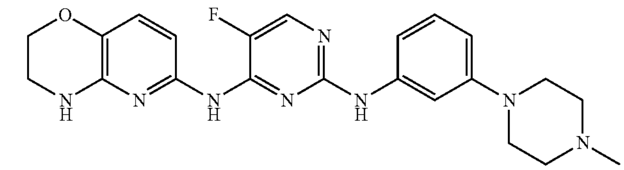 [SMILES: CN1CCN(c2cccc(Nc3ncc(F)c(Nc4ccc5c(n4)NCCO5)n3)c2)CC1] | N4-(3,4-dihydro-2H-pyrido[3,2-b][1,4]oxazin-6-yl)-5-methyl-N2-(3-(4-methylpiperazin-1-yl)phenyl)pyrimidine-2,4-diamine | A | B |
| 41 | 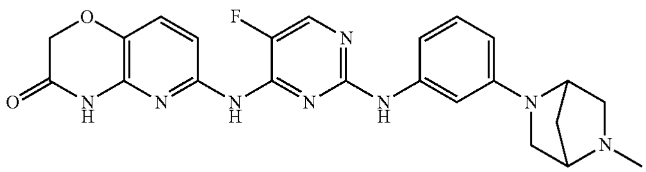 [SMILES: CN1CC2CC1CN2c1cccc(Nc2ncc(F)c(Nc3ccc4c(n3)NC(=O)CO4)n2)c1] | 6-(5-fluoro-2-(3-(5-methyl-2,5-diaza-bicyclo[2.2.1]heptan-2-yl)phenylamino)pyrimidin-4-ylamino)-2H-pyrido[3,2-b][1,4]oxazin-3(4H)-one | A | A |
| 42 | 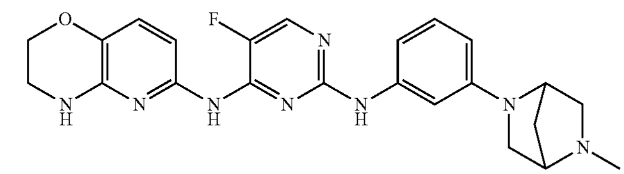 [SMILES: CN1CC2CC1CN2c1cccc(Nc2ncc(F)c(Nc3ccc4c(n3)NCCO4)n2)c1] | N4-(3,4-dihydro-2H-pyrido[3,2-b][1,4]oxazin-6-yl)-5-fluoro-N2-(3-(5-methyl-2,5-diazabicyclo[2.2.1]heptan-2-yl)phenyl)pyrimidine-2,4-diamine | A | A |
| 43 | 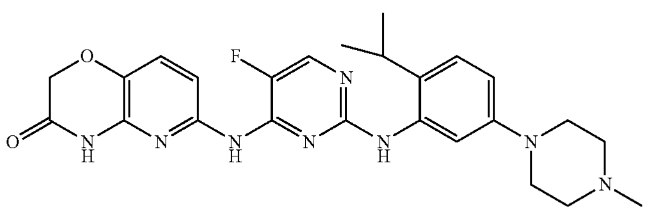 [SMILES: CC(C)c1ccc(N2CCN(C)CC2)cc1Nc1ncc(F)c(Nc2ccc3c(n2)NC(=O)CO3)n1] | 6-(5-fluoro-2-(2-isopropyl-5-(4-methylpiperazin-1-yl)phenylamino)pyrimidin-4-ylamnino)-2H-pyrido[3,2-b][1,4]oxazin-3(4H)-one | A | A |
| 44 | 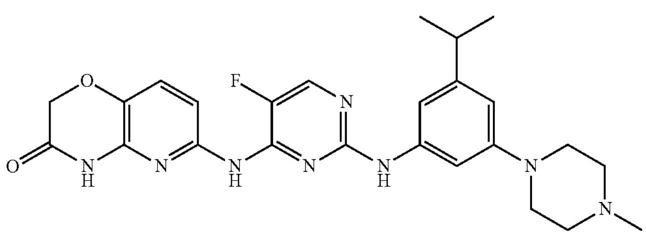 [SMILES: CC(C)c1cc(Nc2ncc(F)c(Nc3ccc4c(n3)NC(=O)CO4)n2)cc(N2CCN(C)CC2)c1] | 6-(5-fluoro-2-(3-isopropyl-5-(4-methylpiperazin-1-yl)phenylamino)pyrimidin-4-ylamino)-2H-pyrido[3,2-b][1,4]oxazin-3(4H)-one | A | D |
| 45 | 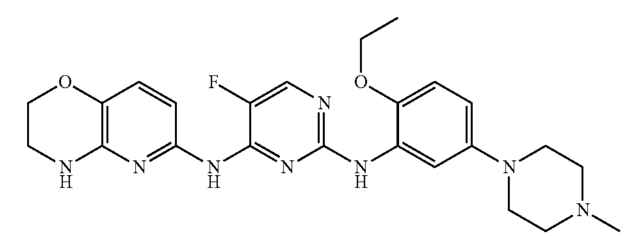 [SMILES: CCOc1ccc(N2CCN(C)CC2)cc1Nc1ncc(F)c(Nc2ccc3c(n2)NCCO3)n1] | N4-(3,4-dihydro-2H-pyrido[3,2-b][1,4]oxazin-6-yl)-N2-(2-ethoxy-5-(4-methylpiperazin-1-yl)phenyl)-5-fluoro-pyrimidine-2,4-diamine | A | A |
| 46 | 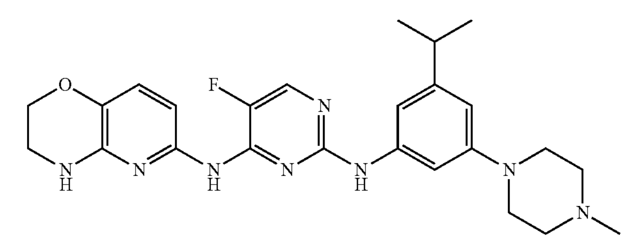 [SMILES: CC(C)c1cc(Nc2ncc(F)c(Nc3ccc4c(n3)NCCO4)n2)cc(N2CCN(C)CC2)c1] | N4-(3,4-dihydro-2H-pyrido[3,2-b][1,4]oxazin-6-yl)-5-fluoro-N2-(3-isopropyl-5-(4-methylpiperazin-1-yl)phenyl)pyrimidine-2,4-diamine | A | B |

TABLE 1-continued

| # | Structure | Name | PLK1 IC$_{50}$ (μM) biochemical assay | PLK1 IC$_{50}$ (μM) cellular assay |
|---|---|---|---|---|
| 47 | 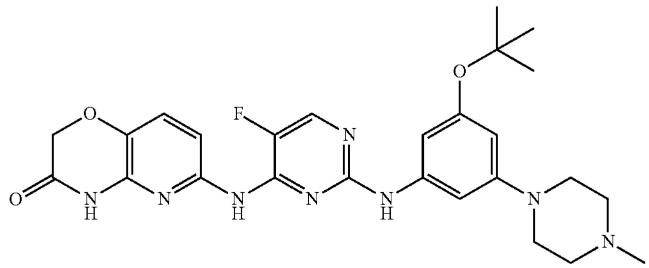 [SMILES: CN1CCN(c2cc(Nc3ncc(F)c(Nc4ccc5c(n4)NC(=O)CO5)n3)cc(OC(C)(C)C)c2)CC1] | 6-(2-(3-tert-butoxy-5-(4-methylpiperazin-1-yl)phenylamino)-5-fluoro-pyrimidin-4-ylamino)-2H-pyrido[3,2-b][1,4]oxazin-3(4H)-one | A | A |
| 48 | 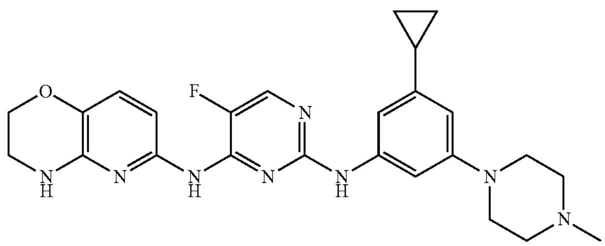 [SMILES: CN1CCN(c2cc(Nc3ncc(F)c(Nc4ccc5c(n4)NCCO5)n3)cc(C3CC3)c2)CC1] | N2-(3-cyclopropyl-5-(4-methylpiperazin-1-yl)phenyl)-N4-(3,4-dihydro-2H-pyrido[3,2-b][1,4]oxazin-6-yl)-5-fluoropyrimidine-2,4-diamine | A | A |
| 49 | 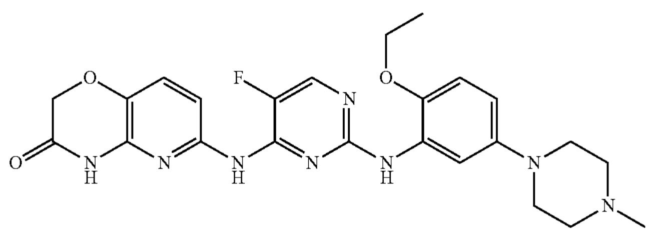 [SMILES: CCOc1ccc(N2CCN(C)CC2)cc1Nc1ncc(F)c(Nc2ccc3c(n2)NC(=O)CO3)n1] | 6-(2-(2-ethoxy-5-(4-methylpiperazin-1-yl)phenylamino)-5-fluoro-pyrimidin-4-ylamino)-2H-pyrido[3,2-b][1,4]oxazin-3(4H)-one | A | A |
| 50 | 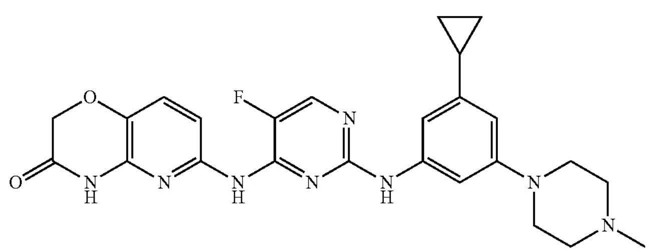 [SMILES: CN1CCN(c2cc(Nc3ncc(F)c(Nc4ccc5c(n4)NC(=O)CO5)n3)cc(C3CC3)c2)CC1] | 6-(2-(3-cyclopropyl-5-(4-methylpiperazin-1-yl)phenylamino)-5-fluoro-pyrimidin-4-ylamino)-2H-pyrido[3,2-b][1,4]oxazin-3(4H)-one | A | A |
| 51 | 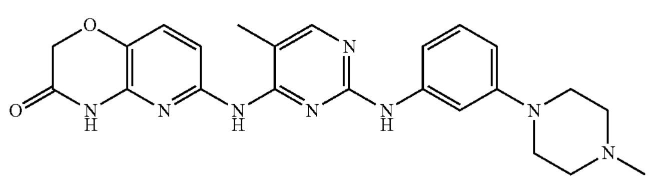 [SMILES: Cc1cnc(Nc2cccc(N3CCN(C)CC3)c2)nc1Nc1ccc2c(n1)NC(=O)CO2] | 6-(5-methyl-2-(3-(4-methylpiperazin-1-yl)phenylamino)pyrimidin-4-ylamino)-2H-pyrido[3,2-b][1,4]oxazin-3(4H)-one | A | B |
| 52 | 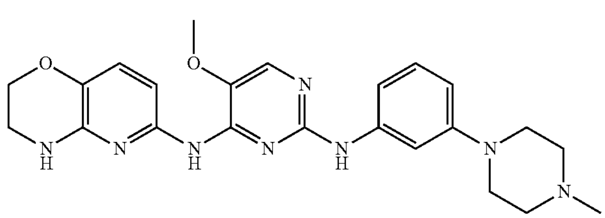 [SMILES: COc1cnc(Nc2cccc(N3CCN(C)CC3)c2)nc1Nc1ccc2c(n1)NCCO2] | N4-(3,4-dihydro-2H-pyrido[3,2-b][1,4]oxazin-6-yl)-5-methoxy-N2-(3-(4-methylpiperazin-1-yl)phenyl)pyrimidine-2,4-diamine | A | B |

TABLE 1-continued

| # | Structure | Name | PLK1 IC$_{50}$ (μM) biochemical assay | PLK1 IC$_{50}$ (μM) cellular assay |
|---|---|---|---|---|
| 53 | 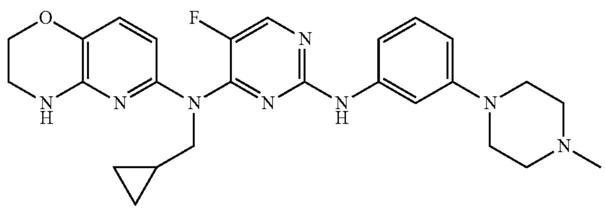 [SMILES: CN1CCN(c2cccc(Nc3ncc(F)c(N(CC4CC4)c4ccc5c(n4)NCCO5)n3)c2)CC1] | N4-(cyclopropylmethyl)-N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | B | D |
| 54 | 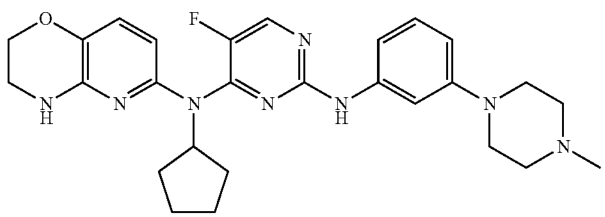 [SMILES: CN1CCN(c2cccc(Nc3ncc(F)c(N(c4ccc5c(n4)NCCO5)C4CCCC4)n3)c2)CC1] | N4-cyclopentyl-N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | C | D |
| 55 | 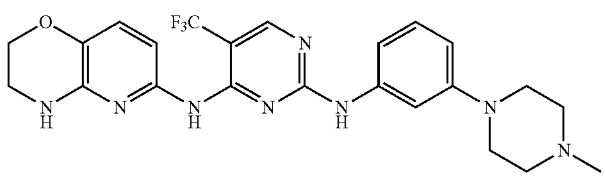 [SMILES: CN1CCN(c2cccc(Nc3ncc(C(F)(F)F)c(Nc4ccc5c(n4)NCCO5)n3)c2)CC1] | N4-(3,4-dihydro-2H-pyrido[3,2-b][1,4]oxazin-6-yl)-N2-(3-(4-methyl-piperazin-1-yl)phenyl)-5-(trifluoro-methyl)pyrimidine-2,4-diamine | A | A |
| 56 | 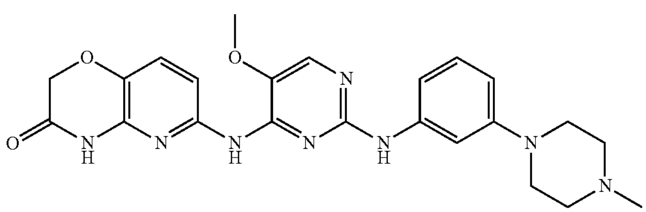 [SMILES: COc1cnc(Nc2cccc(N3CCN(C)CC3)c2)nc1Nc1ccc2c(n1)NC(=O)CO2] | 6-(5-methoxy-2-(3-(4-methylpiperazin-1-yl)phenylamino)pyrimidin-4-ylamino)-2H-pyrido[3,2-b][1,4]oxazin-3(4H)-one | A | D |
| 57 | 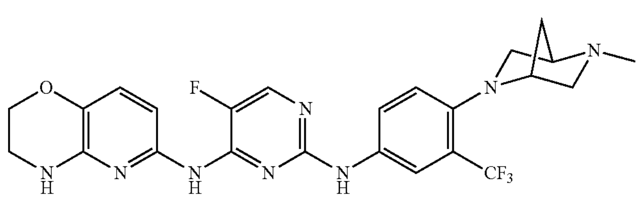 [SMILES: CN1CC2CC1CN2c1ccc(Nc2ncc(F)c(Nc3ccc4c(n3)NCCO4)n2)cc1C(F)(F)F] | N4-(3,4-dihydro-2H-pyrido[3,2-b][1,4]oxazin-6-yl)-5-fluoro-N2-(4-(5-methyl-2,5-diazabicyclo[2.2.1]heptan-2-yl)-3-(trifluoro-methyl)phenyl)pyrimidine-2,4-diamine | D | |
| 58 | Formate salt | 6-(5-chloro-2-(4-(4-methylpiperazin-1-yl)phenylamino)pyrimidin-4-ylamino)-4-propyl-2H-benzo[b][1,4]oxazin-3(4H)-one formate | | |

TABLE 1-continued

| # | Structure | Name | PLK1 IC$_{50}$ (μM) biochemical assay | PLK1 IC$_{50}$ (μM) cellular assay |
|---|---|---|---|---|
| 59 | Formate salt | 6-(5-chloro-2-(4-(4-methylpiperazin-1-yl)phenylamino)pyrimidin-4-ylamino)-4-(3-fluoropropyl)-2H-benzo[b][1,4]oxazin-3(4H)-one formate | | |
| 60 | Formate salt | 6-(5-chloro-2-(6-(4-methylpiperazin-1-yl)pyridin-3-ylamino)pyrimidin-4-ylamino)-4-(3-fluoropropyl)-2H-benzo[b][1,4]oxazin-3(4H)-one formate | | |
| 61 | Formate salt | 4-(2-fluoroethyl)-6-(5-methyl-2-(4-(4-methylpiperazin-1-yl)phenylamino)pyrimidin-4-ylamino)-2H-benzo[b][1,4]oxazin-3(4H)-one formate | | |
| 62 | Formate salt | 6-(5-chloro-2-(4-(4-methylpiperazin-1-yl)phenylamino)pyrimidin-4-ylamino)-4-(2-fluoroethyl)-2H-benzo[b][1,4]oxazin-3(4H)-one formate | | |
| 63 | Formate salt | 6-(5-chloro-2-(4-(4-methylpiperazin-1-yl)phenylamino)pyrimidin-4-ylamino)-4-(2-fluoroethyl)-2,2-dimethyl-2H-benzo[b][1,4]oxazin-3(4H)-one formate | | |

TABLE 1-continued

| # | Structure | Name | PLK1 IC$_{50}$ (μM) bio-chemical assay | PLK1 IC$_{50}$ (μM) cellular assay |
|---|---|---|---|---|
| 64 | Formate salt | 6-(5-fluoro-2-(4-(4-methylpiperazin-1-yl)phenylamino)pyrimidin-4-ylamino)-4-propyl-2H-benzo[b][1,4]oxazin-3(4H)-one formate | | |
| 65 | Formate salt | 6-(5-fluoro-2-(6-(4-methylpiperazin-1-yl)pyridin-3-ylamino)pyrimidin-4-ylamino)-4-propyl-2H-benzo[b][1,4]oxazin-3(4H)-one formate | | |
| 66 | Formate salt | 6-(5-methyl-2-(4-(4-methylpiperazin-1-yl)phenylamino)pyrimidin-4-ylamino)-4-propyl-2H-benzo[b][1,4]oxazin-3(4H)-one formate | | |
| 67 | Formate salt | 6-(5-methyl-2-(6-(4-methylpiperazin-1-yl)pyridin-3-ylamino)pyrimidin-4-ylamino)-4-propyl-2H-benzo[b][1,4]oxazin-3(4H)-one formate | | |
| 68 | Formate salt | 2,2-dimethyl-6-(5-methyl-2-(6-(4-methylpiperazin-1-yl)pyridin-3-ylamino)pyrimidin-4-ylamino)-4-propyl-2H-benzo[b][1,4]oxazin-3(4H)-one formate | | |

TABLE 1-continued

| # | Structure | Name | PLK1 IC$_{50}$ (µM) bio-chemical assay | PLK1 IC$_{50}$ (µM) cellular assay |
|---|---|---|---|---|
| 69 | Formate salt | 4-(3-fluoropropyl)-6-(5-methyl-2-(6-(4-methylpiperazin-1-yl)pyridin-3-ylamino)pyrimidin-4-ylamino)-2H-benzo[b][1,4]oxazin-3(4H)-one formate | | |
| 70 | Formate salt | 6-(5-chloro-2-(6-(4-methylpiperazin-1-yl)pyridin-3-ylamino)pyrimidin-4-ylamino)-2,2-dimethyl-4-propyl-2H-benzo[b][1,4]oxazin-3(4H)-one formate | | |
| 71 | Formate salt | 6-(5-chloro-2-(6-(4-methylpiperazin-1-yl)pyridin-3-ylamino)pyrimidin-4-ylamino)-4-propyl-2H-benzo[b][1,4]oxazin-3(4H)-one formate | | |
| 72 | Formate salt | 4-(2-fluoroethyl)-6-(5-methyl-2-(6-(4-methylpiperazin-1-yl)pyridin-3-ylamino)pyrimidin-4-ylamino)-2H-benzo[b][1,4]oxazin-3(4H)-one formate | | |
| 73 | Formate salt | 6-(5-chloro-2-(6-(4-methylpiperazin-1-yl)pyridin-3-ylamino)pyrimidin-4-ylamino)-4-(2-fluoroethyl)-2H-benzo[b][1,4]oxazin-3(4H)-one formate | | |

TABLE 1-continued

| # | Structure | Name | PLK1 IC$_{50}$ (μM) biochemical assay | PLK1 IC$_{50}$ (μM) cellular assay |
|---|-----------|------|---|---|
| 74 | Formate salt | 6-(5-chloro-2-(6-(4-methylpiperazin-1-yl)pyridin-3-ylamino)pyrimidin-4-ylamino)-4-(2-fluoroethyl)-2,2-dimethyl-2H-benzo[b][1,4]oxazin-3(4H)-one formate | | |
| 75 | Formate salt | 6-(5-fluoro-2-(6-(4-methylpiperazin-1-yl)pyridin-3-ylamino)pyrimidin-4-ylamino)-2H-benzo[b][1,4]oxazin-3(4H)-one formate | | |
| 76 | Formate salt | 6-(5-methyl-2-(6-(4-methylpiperazin-1-yl)pyridin-3-ylamino)pyrimidin-4-ylamino)-2H-benzo[b][1,4]oxazin-3(4H)-one formate | | |
| 77 | Formate salt | 6-(5-methyl-2-(6-(piperazin-1-yl)pyridin-3-ylamino)pyrimidin-4-ylamino)-2H-benzo[b][1,4]oxazin-3(4H)-one formate | | |
| 78 | Formate salt | tert-butyl 4-(5-(5-methyl-4-(3-oxo-3,4-dihydro-2H-benzo[b][1,4]oxazin-6-ylamino)pyrimidin-2-ylamino)pyridin-2-yl)piperazine-1-carboxylate formate | | |
| 79 | Formate salt | 6-(2-(6-(4-ethylpiperazin-1-yl)pyridin-3-ylamino)-5-methylpyrimidin-4-ylamino)-2H-benzo[b][1,4]oxazin-3(4H)-one formate | | |

TABLE 1-continued

| # | Structure | Name | PLK1 IC$_{50}$ (μM) biochemical assay | PLK1 IC$_{50}$ (μM) cellular assay |
|---|---|---|---|---|
| 80 | Formate salt | 6-(2-(6-(4-isopropyl-piperazin-1-yl)pyridin-3-ylamino)-5-methylpyrimidin-4-ylamino)-2H-benzo[b][1,4]oxazin-3(4H)-one formate | | |
| 81 | Formate salt | 6-(2-(6-(4-(cyclopropyl-methyl)piperazin-1-yl)pyridin-3-ylamino)-5-methylpyrimidin-4-ylamino)-2H-benzo[b][1,4]oxazin-3(4H)-one formate | | |
| 82 | Formate salt | 6-(2-(6-(4-benzylpiperazin-1-yl)pyridin-3-ylamino)-5-methylpyrimidin-4-ylamino)-2H-benzo[b][1,4]oxazin-3(4H)-one formate | | |
| 83 | Formate salt | 6-(5-methyl-2-(6-(4-methylpiperazin-1-yl)pyridazin-3-ylamino)pyrimidin-4-ylamino)-2H-benzo[b][1,4]oxazin-3(4H)-one formate | | |
| 84 | Formate salt | 6-(5-methyl-2-(6-(4-(methylsulfonyl)piperazin-1-yl)pyridin-3-ylamino)pyrimidin-4-ylamino)-2H-benzo[b][1,4]oxazin-3(4H)-one formate | | |
| 85 | 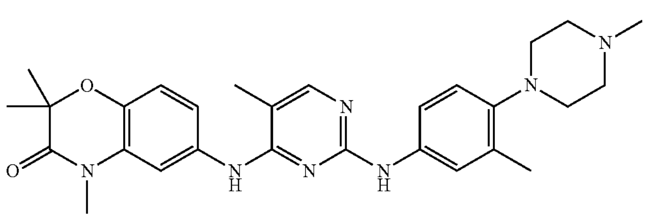 | 2,2,4-trimethyl-6-(5-methyl-2-(3-methyl-4-(4-methylpiperazin-1-yl)phenylamino)pyrimidin-4-ylamino)-2H-benzo[b][1,4]oxazin-3(4H)-one | | |

TABLE 1-continued

| # | Structure | Name | PLK1 IC$_{50}$ (µM) biochemical assay | PLK1 IC$_{50}$ (µM) cellular assay |
|---|---|---|---|---|
| 86 | 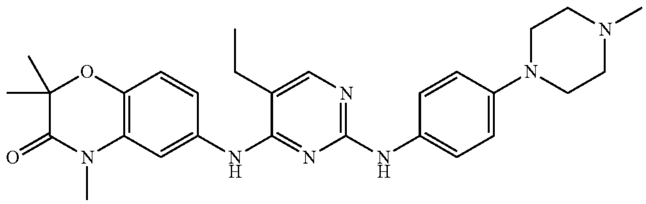 | 6-(5-ethyl-2-(4-(4-methylpiperazin-1-yl)phenylamino)pyrimidin-4-ylamino)-2,2,4-trimethyl-2H-benzo[b][1,4]oxazin-3(4H)-one | | |
| 87 | 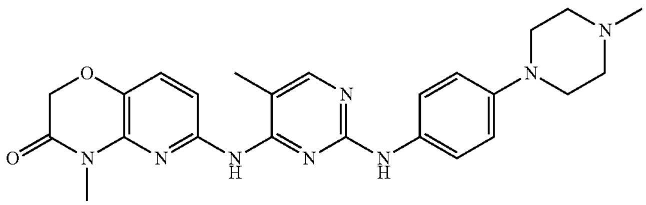 [SMILES: Cc1cnc(Nc2ccc(N3CCN(C)CC3)cc2)nc1Nc1ccc2c(n1)N(C)C(=O)CO2] | 4-methyl-6-(5-methyl-2-(4-(4-methylpiperazin-1-yl)phenylamino)pyrimidin-4-ylamino)-2H-pyrido[3,2-b][1,4]oxazin-3(4H)-one | | |
| 88 | 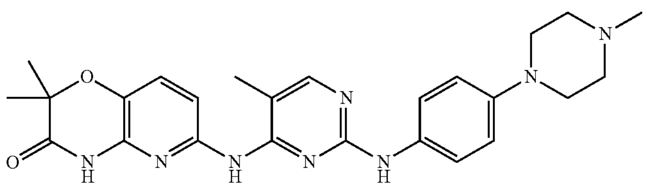 | 2,2-dimethyl-6-(5-methyl-2-(4-(4-methylpiperazin-1-yl)phenylamino)pyrimidin-4-ylamino)-2H-pyrido[3,2-b][1,4]oxazin-3(4H)-one | | D |
| 89 | 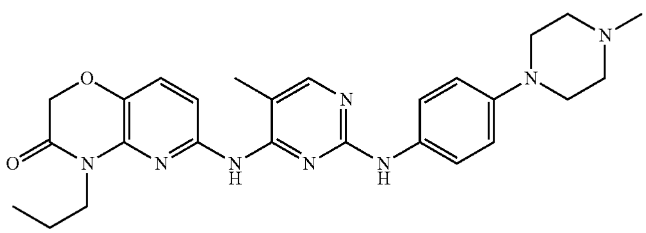 [SMILES: CCCN1C(=O)COc2ccc(Nc3nc(Nc4ccc(N5CCN(C)CC5)cc4)ncc3C)nc21] | 6-(5-methyl-2-(4-(4-methylpiperazin-1-yl)phenylamino)pyrimidin-4-ylamino)-4-propyl-2H-pyrido[3,2-b][1,4]oxazin-3(4H)-one | | |
| 90 | 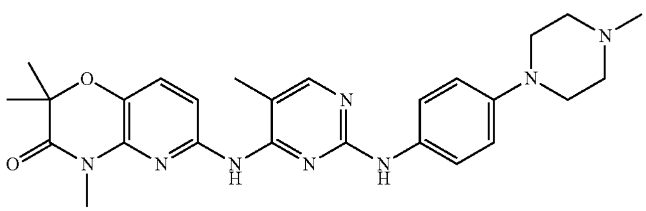 | 2,2,4-trimethyl-6-(5-methyl-2-(4-(4-methylpiperazin-1-yl)phenylamino)pyrimidin-4-ylamino)-2H-pyrido[3,2-b][1,4]oxazin-3(4H)-one | | |
| 91 | 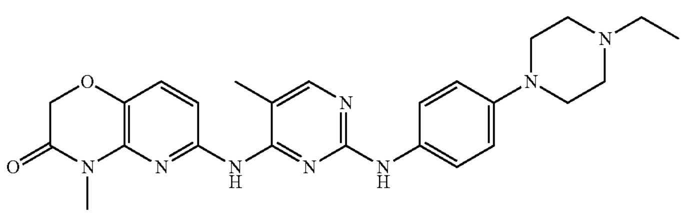 [SMILES: CCN1CCN(c2ccc(Nc3ncc(C)c(Nc4ccc5c(n4)N(C)C(=O)CO5)n3)cc2)CC1] | 6-(2-(4-(4-ethylpiperazin-1-yl)phenylamino)-5-methylpyrimidin-4-ylamino)-4-methyl-2H-pyrido[3,2-b][1,4]oxazin-3(4H)-one | | D |
| 92 | 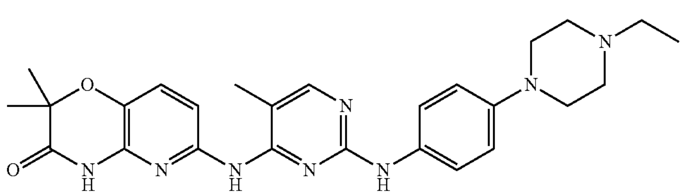 [SMILES: CCN1CCN(c2ccc(Nc3ncc(C)c(Nc4ccc5c(n4)NC(=O)C(C)(C)O5)n3)cc2)CC1] | 6-(2-(4-(4-ethylpiperazin-1-yl)phenylamino)-5-methylpyrimidin-4-ylamino)-2,2-dimethyl-2H-pyrido[3,2-b][1,4]oxazin-3(4H)-one | | D |

TABLE 1-continued

| # | Structure | Name | PLK1 IC$_{50}$ (μM) biochemical assay | PLK1 IC$_{50}$ (μM) cellular assay |
|---|---|---|---|---|
| 93 | 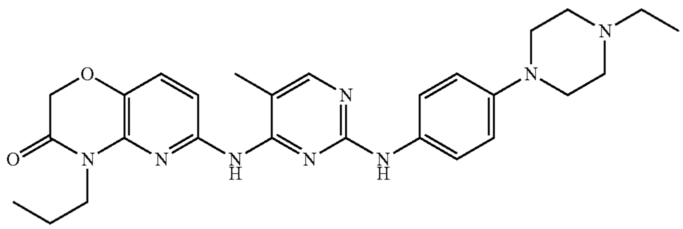 [SMILES: CCCN1C(=O)COc2ccc(Nc3nc(Nc4ccc(N5CCN(CC)CC5)cc4)ncc3C)nc21] | 6-(2-(4-(4-ethylpiperazin-1-yl)phenylamino)-5-methylpyrimidin-4-ylamino)-4-propyl-2H-pyrido[3,2-b][1,4]oxazin-3(4H)-one | | |
| 94 | 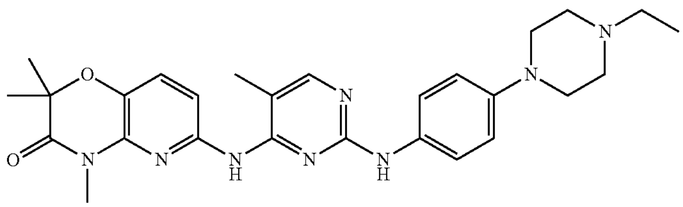 | 6-(2-(4-(4-ethylpiperazin-1-yl)phenylamino)-5-methylpyrimidin-4-ylamino)-2,2,4-trimethyl-2H-pyrido[3,2-b][1,4]oxazin-3(4H)-one | | D |
| 95 | 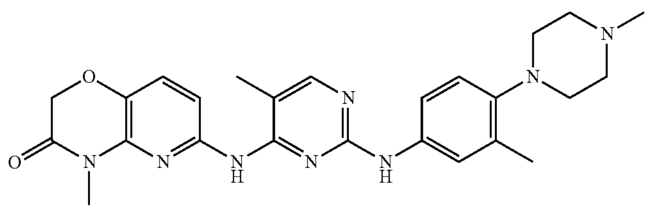 [SMILES: Cc1cc(Nc2ncc(C)c(Nc3ccc4c(n3)N(C)C(=O)CO4)n2)ccc1N1CCN(C)CC1] | 4-methyl-6-(5-methyl-2-(3-methyl-4-(4-methylpiperazin-1-yl)phenylamino)pyrimidin-4-ylamino)-2H-pyrido[3,2-b][1,4]oxazin-3(4H)-one | B | D |
| 96 | 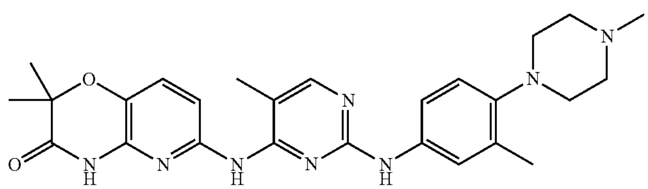 | 2,2-dimethyl-6-(5-methyl-2-(3-methyl-4-(4-methylpiperazin-1-yl)phenylamino)pyrimidin-4-ylamino)-2H-pyrido[3,2-b][1,4]oxazin-3(4H)-one | C | D |
| 97 | 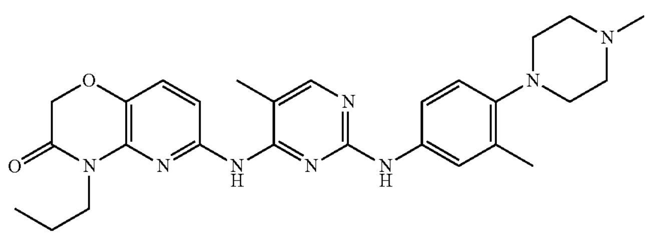 [SMILES: CCCN1C(=O)COc2ccc(Nc3nc(Nc4ccc(N5CCN(C)CC5)c(C)c4)ncc3C)nc21] | 6-(5-methyl-2-(3-methyl-4-(4-methylpiperazin-1-yl)phenylamino)pyrimidin-4-ylamino)-4-propyl-2H-pyrido[3,2-b][1,4]oxazin-3(4H)-one | A | B |
| 98 | 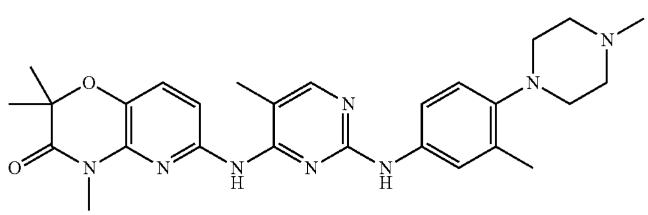 | 2,2,4-trimethyl-6-(5-methyl-2-(3-methyl-4-(4-methylpiperazin-1-yl)phenylamino)pyrimidin-4-ylamino)-2H-pyrido[3,2-b][1,4]oxazin-3(4H)-one | | D |
| 99 | 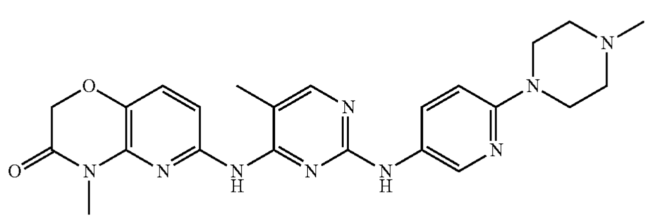 [SMILES: Cc1cnc(Nc2ccc(N3CCN(C)CC3)nc2)nc1Nc1ccc2c(n1)N(C)C(=O)CO2] | 4-methyl-6-(5-methyl-2-(6-(4-methylpiperazin-1-yl)pyridin-3-ylamino)pyrimidin-4-ylamino)-2H-pyrido[3,2-b][1,4]oxazin-3(4H)-one | | |

TABLE 1-continued

| # | Structure | Name | PLK1 IC$_{50}$ (μM) biochemical assay | PLK1 IC$_{50}$ (μM) cellular assay |
|---|---|---|---|---|
| 100 | 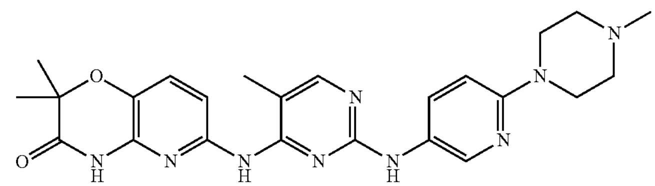 | 2,2-dimethyl-6-(5-methyl-2-(6-(4-methylpiperazin-1-yl)pyridin-3-ylamino)pyrimidin-4-ylamino)-2H-pyrido[3,2-b][1,4]oxazin-3(4H)-one | | |
| 101 | 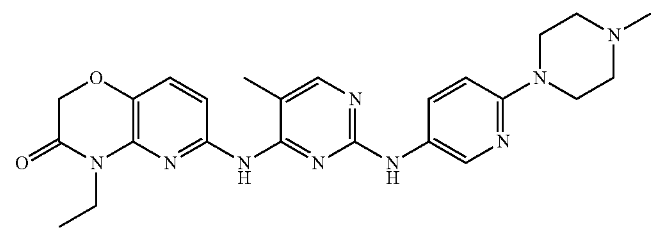 [SMILES: CCN1C(=O)COc2ccc(Nc3nc(Nc4ccc(N5CCN(C)CC5)nc4)ncc3C)nc21] | 4-ethyl-6-(5-methyl-2-(6-(4-methylpiperazin-1-yl)pyridin-3-ylamino)pyrimidin-4-ylamino)-2H-pyrido[3,2-b][1,4]oxazin-3(4H)-one | A | B |
| 102 | 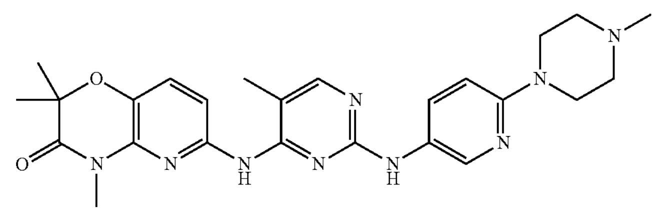 | 2,2,4-trimethyl-6-(5-methyl-2-(6-(4-methylpiperazin-1-yl)pyridin-3-ylamino)pyrimidin-4-ylamino)-2H-pyrido[3,2-b][1,4]oxazin-3(4H)-one | | |
| 103 | 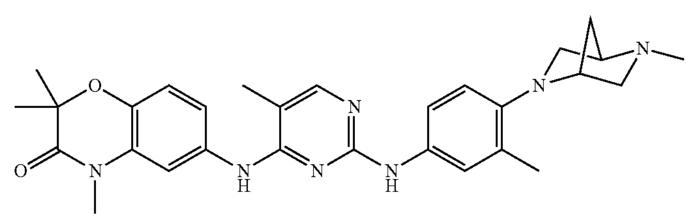 | 2,2,4-trimethyl-6-(5-methyl-2-(3-methyl-4-(5-methyl-2,5-diaza-bicyclo[2.2.1]heptan-2-yl)phenylamino)pyrimidin-4-ylamino)-2H-benzo[b][1,4]oxazin-3(4H)-one | | |
| 104 | 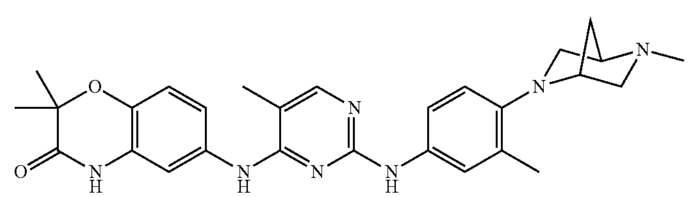 | 2,2-dimethyl-6-(5-methyl-2-(3-methyl-4-(5-methyl-2,5-diaza-bicyclo[2.2.1]heptan-2-yl)phenylamino)pyrimidin-4-ylamino)-2H-benzo[b][1,4]oxazin-3(4H)-one | | |
| 105 | 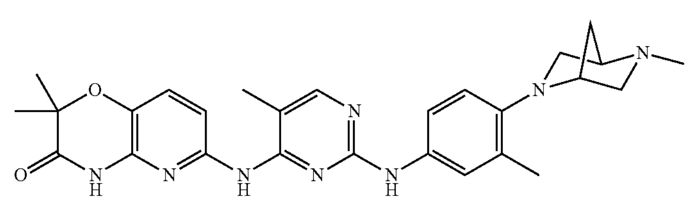 | 2,2-dimethyl-6-(5-methyl-2-(3-methyl-4-(5-methyl-2,5-diaza-bicyclo[2.2.1]heptan-2-yl)phenylamino)pyrimidin-4-ylamino)-2H-pyrido[3,2-b][1,4]oxazin-3(4H)-one | | |
| 106 | 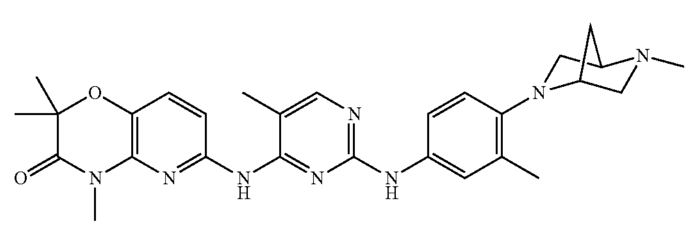 | 2,2,4-trimethyl-6-(5-methyl-2-(3-methyl-4-(5-methyl-2,5-diaza-bicyclo[2.2.1]heptan-2-yl)phenylamino)pyrimidin-4-ylamino)-2H-pyrido[3,2-b][1,4]oxazin-3(4H)-one | | |

TABLE 1-continued

| # | Structure | Name | PLK1 IC$_{50}$ (μM) bio-chemical assay | PLK1 IC$_{50}$ (μM) cellular assay |
|---|---|---|---|---|
| 107 | 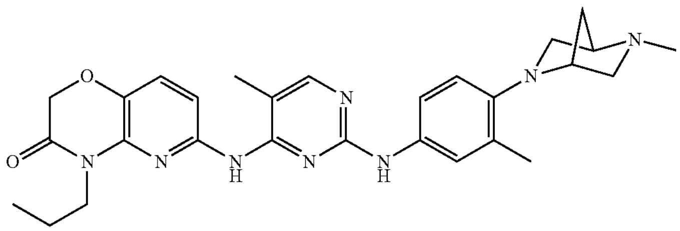 [SMILES: CCCN1C(=O)COc2ccc(Nc3nc(Nc4ccc(N5CC6CC5CN6C)c(C)c4)ncc3C)nc21] | 6-(5-methyl-2-(3-methyl-4-(5-methyl-2,5-diazabicyclo[2.2.1]heptan-2-yl)phenylamino)pyrimidin-4-ylamino)-4-propyl-2H-pyrido[3,2-b][1,4]oxazin-3(4H)-one | A | B |
| 108 | 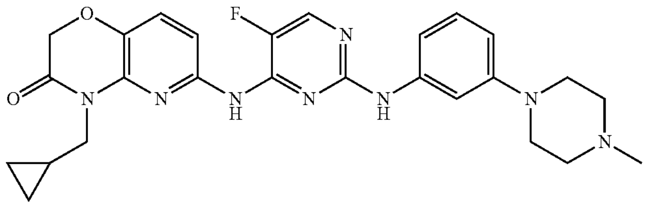 | 4-(cyclopropylmethyl)-6-(5-fluoro-2-(3-(4-methylpiperazin-1-yl)phenylamino)pyrimidin-4-ylamino)-2H-pyrido[3,2-b][1,4]oxazin-3(4H)-one | A | B |
| 109 | 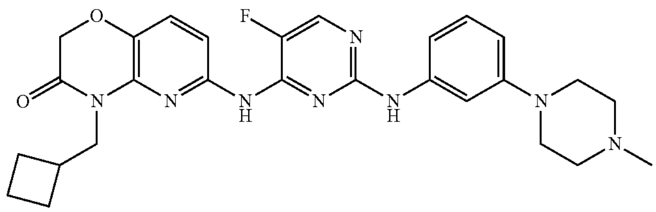 [SMILES: CN1CCN(c2cccc(Nc3ncc(F)c(Nc4ccc5c(n4)N(CC4CCC4)C(=O)CO5)n3)c2)CC1] | 4-(cyclobutylmethyl)-6-(5-fluoro-2-(3-(4-methylpiperazin-1-yl)phenylamino)pyrimidin-4-ylamino)-2H-pyrido[3,2-b][1,4]oxazin-3(4H)-one | A | B |
| 110 | 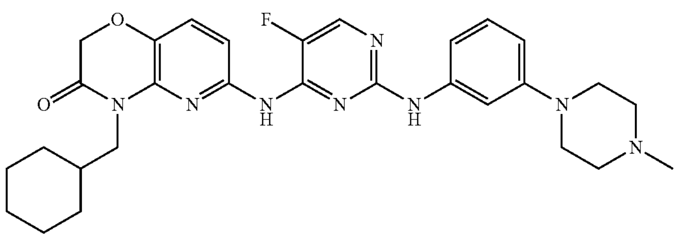 [SMILES: CN1CCN(c2cccc(Nc3ncc(F)c(Nc4ccc5c(n4)N(CC4CCCCC4)C(=O)CO5)n3)c2)CC1] | 4-(cyclohexylmethyl)-6-(5-fluoro-2-(3-(4-methylpiperazin-1-yl)phenylamino)pyrimidin-4-ylamino)-2H-pyrido[3,2-b][1,4]oxazin-3(4H)-one | C | D |
| 111 | 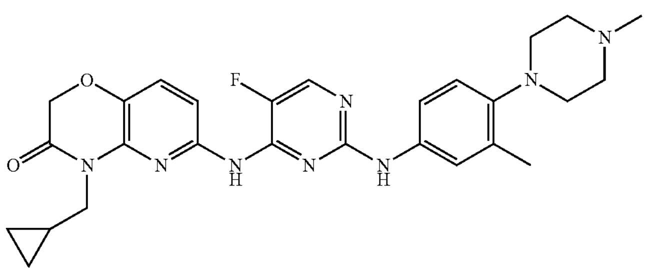 | 4-(cyclopropylmethyl)-6-(5-fluoro-2-(3-methyl-4-(4-methylpiperazin-1-yl)phenylamino)pyrimidin-4-ylamino)-2H-pyrido[3,2-b][1,4]oxazin-3(4H)-one | B | |
| 112 | 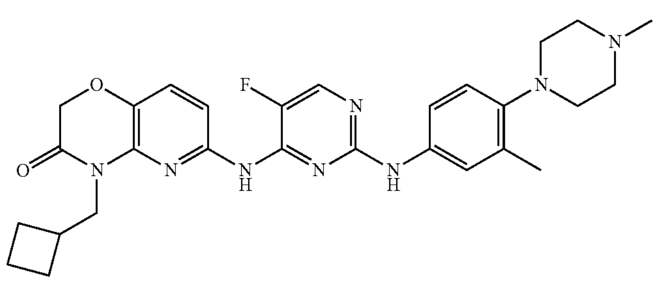 [SMILES: Cc1cc(Nc2ncc(F)c(Nc3ccc4c(n3)N(CC3CCC3)C(=O)CO4)n2)ccc1N1CCN(C)CC1] | 4-(cyclobutylmethyl)-6-(5-fluoro-2-(3-methyl-4-(4-methylpiperazin-1-yl)phenylamino)pyrimidin-4-ylamino)-2H-pyrido[3,2-b][1,4]oxazin-3(4H)-one | D | D |

TABLE 1-continued

| # | Structure | Name | PLK1 IC$_{50}$ (μM) biochemical assay | PLK1 IC$_{50}$ (μM) cellular assay |
|---|---|---|---|---|
| 113 | 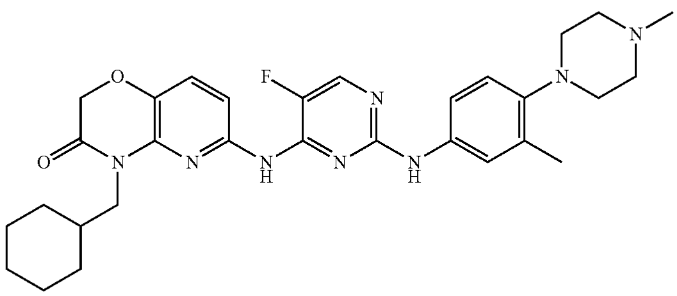 [SMILES: Cc1cc(Nc2ncc(F)c(Nc3ccc4c(n3)N(CC3CCCCC3)C(=O)CO4)n2)ccc1N1CCN(C)CC1] | 4-(cyclohexylmethyl)-6-(5-fluoro-2-(3-methyl-4-(4-methylpiperazin-1-yl)phenylamino)pyrimidin-4-ylamino)-2H-pyrido[3,2-b][1,4]oxazin-3(4H)-one | D | D |
| 114 | 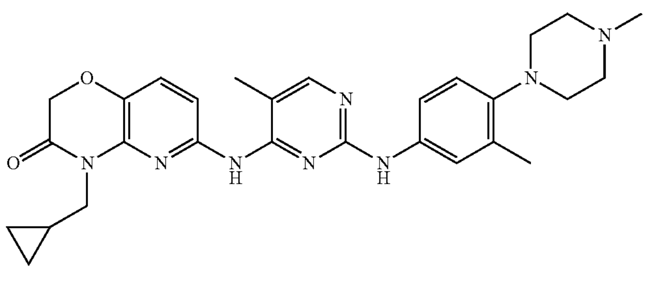 [SMILES: Cc1cc(Nc2ncc(C)c(Nc3ccc4c(n3)N(CC3CC3)C(=O)CO4)n2)ccc1N1CCN(C)CC1] | 4-(cyclopropylmethyl)-6-(5-methyl-2-(3-methyl-4-(4-methyl-piperazin-1-yl)phenylamino)pyrimidin-4-ylamino)-2H-pyrido[3,2-b][1,4]oxazin-3(4H)-one | B | D |
| 115 | 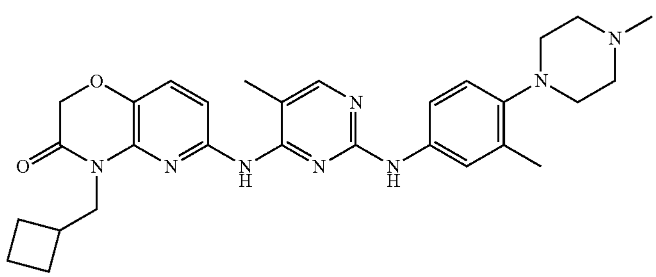 [SMILES: Cc1cc(Nc2ncc(C)c(Nc3ccc4c(n3)N(CC3CCC3)C(=O)CO4)n2)ccc1N1CCN(C)CC1] | 4-(cyclobutylmethyl)-6-(5-methyl-2-(3-methyl-4-(4-methylpiperazin-1-yl)phenylamino)pyrimidin-4-ylamino)-2H-pyrido[3,2-b][1,4]oxazin-3(4H)-one | B | D |
| 116 | 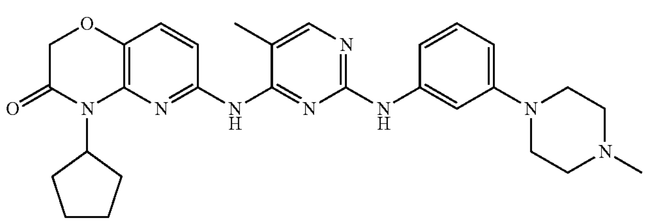 [SMILES: Cc1cnc(Nc2cccc(N3CCN(C)CC3)c2)nc1Nc1ccc2c(n1)N(C1CCCC1)C(=O)CO2] | 4-cyclopentyl-6-(5-methyl-2-(3-(4-methylpiperazin-1-yl)phenylamino)pyrimidin-4-ylamino)-2H-pyrido[3,2-b][1,4]oxazin-3(4H)-one | B | D |
| 117 | 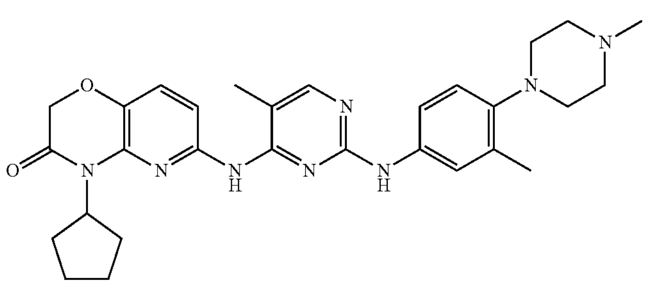 [SMILES: Cc1cc(Nc2ncc(C)c(Nc3ccc4c(n3)N(C3CCCC3)C(=O)CO4)n2)ccc1N1CCN(C)CC1] | 4-cyclopentyl-6-(5-methyl-2-(3-methyl-4-(4-methylpiperazin-1-yl)phenylamino)pyrimidin-4-ylamino)-2H-pyrido[3,2-b][1,4]oxazin-3(4H)-one | D | D |

TABLE 1-continued

| # | Structure | Name | PLK1 IC$_{50}$ (μM) biochemical assay | PLK1 IC$_{50}$ (μM) cellular assay |
|---|---|---|---|---|
| 118 | 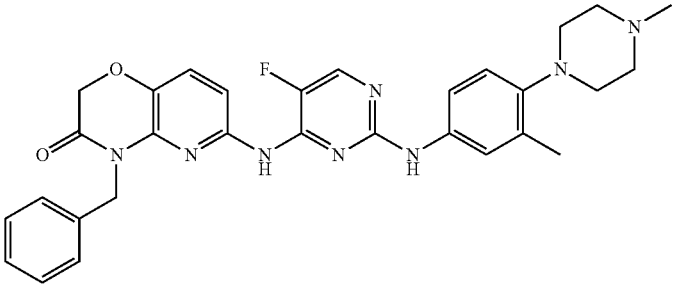 [SMILES: Cc1cc(Nc2ncc(F)c(Nc3ccc4c(n3)N(Cc3ccccc3)C(=O)CO4)n2)ccc1N1CCN(C)CC1] | 4-benzyl-6-(5-fluoro-2-(3-methyl-4-(4-methylpiperazin-1-yl)phenylamino)pyrimidin-4-ylamino)-2H-pyrido[3,2-b][1,4]oxazin-3(4H)-one | D | B |
| 119 | 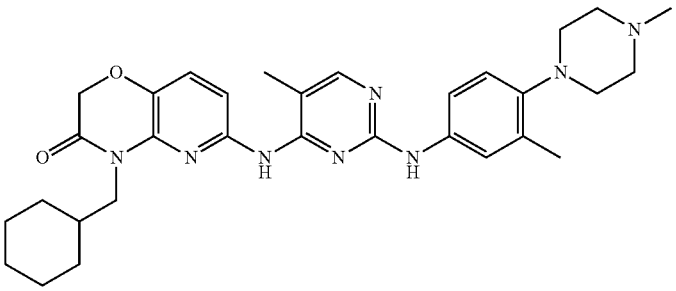 [SMILES: Cc1cc(Nc2ncc(C)c(Nc3ccc4c(n3)N(CC3CCCCC3)C(=O)CO4)n2)ccc1N1CCN(C)CC1] | 4-(cyclohexylmethyl)-6-(5-methyl-2-(3-methyl-4-(4-methylpiperazin-1-yl)phenylamino)pyrimidin-4-ylamino)-2H-pyrido[3,2-b][1,4]oxazin-3(4H)-one | D | D |
| 120 | 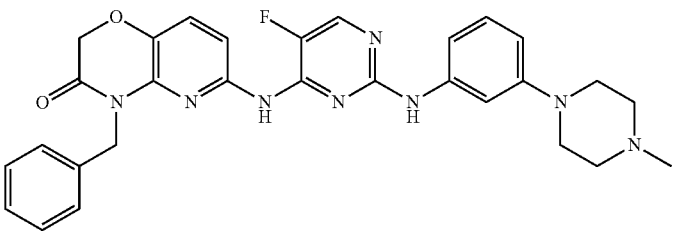 [SMILES: CN1CCN(c2cccc(Nc3ncc(F)c(Nc4ccc5c(n4)N(Cc4ccccc4)C(=O)CO5)n3)c2)CC1] | 4-benzyl-6-(5-fluoro-2-(3-(4-methylpiperazin-1-yl)phenylamino)pyrimidin-4-ylamino)-2H-pyrido[3,2-b][1,4]oxazin-3(4H)-one | B | B |
| 121 | 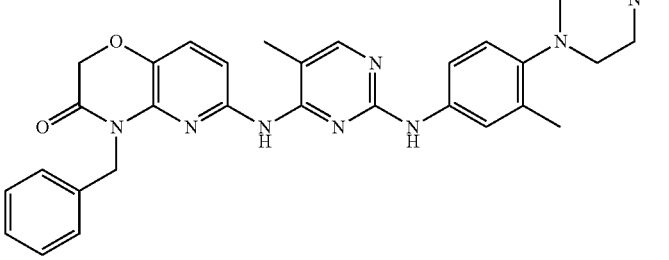 | 4-benzyl-6-(5-methyl-2-(3-methyl-4-(4-methylpiperazin-1-yl)phenylamino)pyrimidin-4-ylamino)-2H-pyrido[3,2-b][1,4]oxazin-3(4H)-one | D | B |
| 122 | 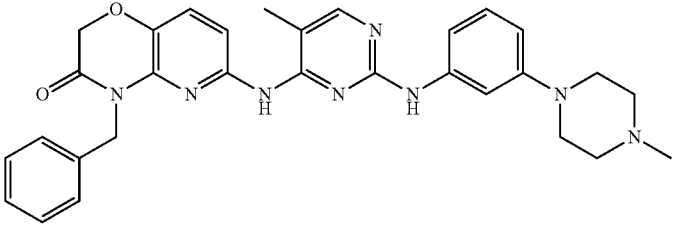 | 4-benzyl-6-(5-methyl-2-(3-(4-methylpiperazin-1-yl)phenylamino)pyrimidin-4-ylamino)-2H-pyrido[3,2-b][1,4]oxazin-3(4H)-one | A | B |

TABLE 1-continued

| # | Structure | Name | PLK1 IC$_{50}$ (μM) bio-chemical assay | PLK1 IC$_{50}$ (μM) cellular assay |
|---|---|---|---|---|
| 123 | 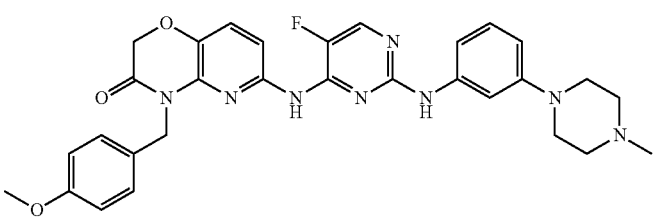 | 6-(5-fluoro-2-(3-(4-methylpiperazin-1-yl)phenylamino)pyrimidin-4-ylamino)-4-(4-methoxybenzyl)-2H-pyrido[3,2-b][1,4]oxazin-3(4H)-one | D | D |
| 124 | 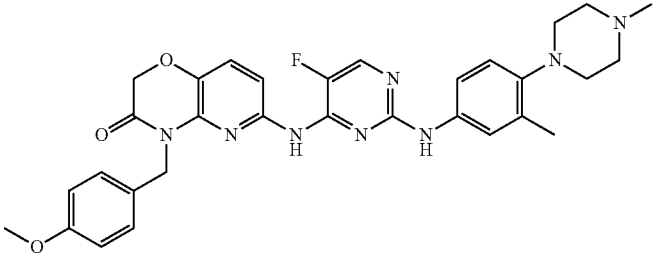 | 6-(5-fluoro-2-(3-methyl-4-(4-methylpiperazin-1-yl)phenylamino)pyrimidin-4-ylamino)-4-(4-methoxybenzyl)-2H-pyrido[3,2-b][1,4]oxazin-3(4H)-one | D | D |
| 125 | 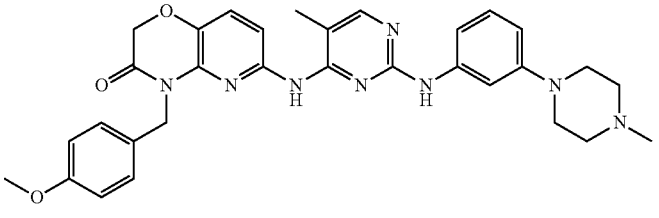 | 4-(4-methoxybenzyl)-6-(5-methyl-2-(3-(4-methylpiperazin-1-yl)phenylamino)pyrimidin-4-ylamino)-2H-pyrido[3,2-b][1,4]oxazin-3(4H)-one | C | D |
| 126 | 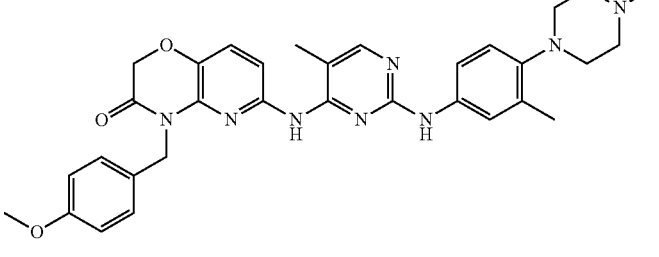 | 4-(4-methoxybenzyl)-6-(5-methyl-2-(3-methyl-4-(4-methylpiperazin-1-yl)phenylamino)pyrimidin-4-ylamino)-2H-pyrido[3,2-b][1,4]oxazin-3(4H)-one | D | B |
| 127 | 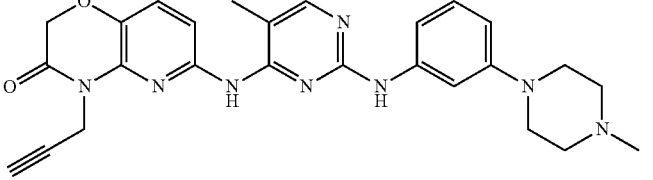 | 6-(5-methyl-2-(3-(4-methylpiperazin-1-yl)phenylamino)pyrimidin-4-ylamino)-4-(prop-2-ynyl)-2H-pyrido[3,2-b][1,4]oxazin-3(4H)-one | A | A |
| 128 | 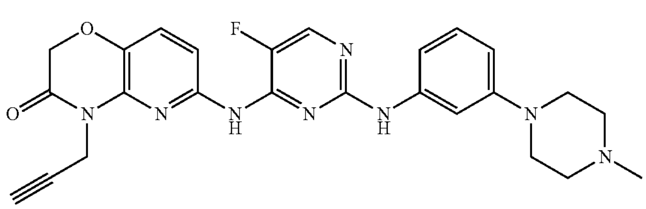 [SMILES: C#CCN1C(=O)COc2ccc(Nc3nc(Nc4cccc(N5CCN(C)CC5)c4)ncc3F)nc21] | 6-(5-fluoro-2-(3-(4-methylpiperazin-1-yl)phenylamino)pyrimidin-4-ylamino)-4-(prop-2-ynyl)-2H-pyrido[3,2-b][1,4]oxazin-3(4H)-one | A | B |

TABLE 1-continued

| # | Structure | Name | PLK1 IC$_{50}$ (μM) biochemical assay | PLK1 IC$_{50}$ (μM) cellular assay |
|---|---|---|---|---|
| 129 | 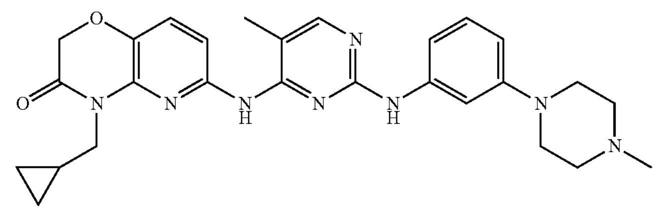 [SMILES: Cc1cnc(Nc2cccc(N3CCN(C)CC3)c2)nc1Nc1ccc2c(n1)N(CC1CC1)C(=O)CO2] | 4-(cyclopropylmethyl)-6-(5-methyl-2-(3-(4-methylpiperazin-1-yl)phenylamino)pyrimidin-4-ylamino)-2H-pyrido[3,2-b][1,4]oxazin-3(4H)-one | A | B |
| 130 | 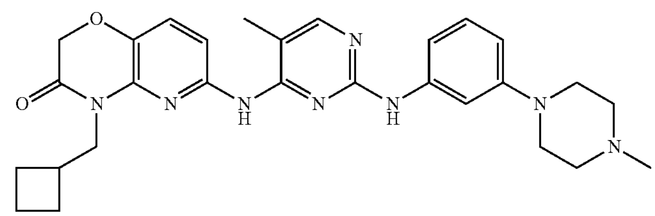 [SMILES: Cc1cnc(Nc2cccc(N3CCN(C)CC3)c2)nc1Nc1ccc2c(n1)N(CC1CCC1)C(=O)CO2] | 4-(cyclobutylmethyl)-6-(5-methyl-2-(3-(4-methylpiperazin-1-yl)phenylamino)pyrimidin-4-ylamino)-2H-pyrido[3,2-b][1,4]oxazin-3(4H)-one | A | B |
| 131 | 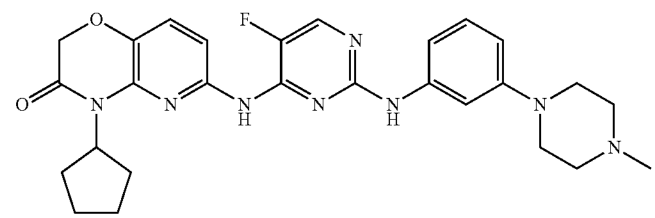 [SMILES: CN1CCN(c2cccc(Nc3ncc(F)c(Nc4ccc5c(n4)N(C4CCCC4)C(=O)CO5)n3)c2)CC1] | 4-cyclopentyl-6-(5-fluoro-2-(3-(4-methylpiperazin-1-yl)phenylamino)pyrimidin-4-ylamino)-2H-pyrido[3,2-b][1,4]oxazin-3(4H)-one | B | D |
| 132 | 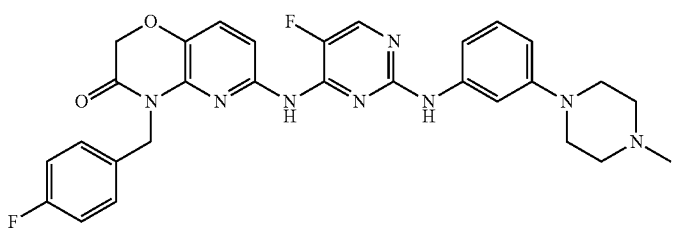 [SMILES: CN1CCN(c2cccc(Nc3ncc(F)c(Nc4ccc5c(n4)N(Cc4ccc(F)cc4)C(=O)CO5)n3)c2)CC1] | 6-(5-fluoro-2-(3-(4-methylpiperazin-1-yl)phenylamino)pyrimidin-4-ylamino)-4-(4-fluorobenzyl)-2H-pyrido[3,2-b][1,4]oxazin-3(4H)-one | C | B |
| 133 | 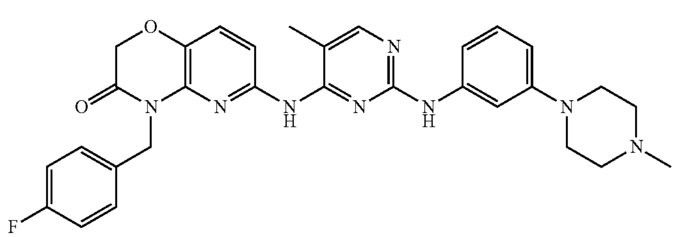 [SMILES: Cc1cnc(Nc2cccc(N3CCN(C)CC3)c2)nc1Nc1ccc2c(n1)N(Cc1ccc(F)cc1)C(=O)CO2] | 4-(4-fluorobenzyl)-6-(5-methyl-2-(3-(4-methylpiperazin-1-yl)phenylamino)pyrimidin-4-ylamino)-2H-pyrido[3,2-b][1,4]oxazin-3(4H)-one | A | B |
| 134 | 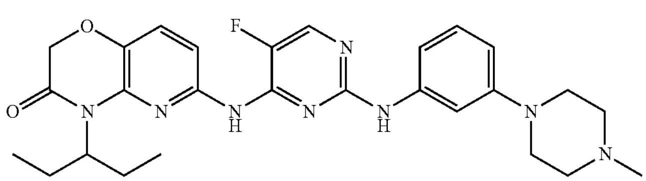 [SMILES: CCC(CC)N1C(=O)COc2ccc(Nc3nc(Nc4cccc(N5CCN(C)CC5)c4)ncc3F)nc21] | 6-(5-fluoro-2-(3-(4-methylpiperazin-1-yl)phenylamino)pyrimidin-4-ylamino)-4-(pentan-3-yl)-2H-pyrido[3,2-b][1,4]oxazin-3(4H)-one | A | A |

TABLE 1-continued

| # | Structure | Name | PLK1 IC$_{50}$ (μM) biochemical assay | PLK1 IC$_{50}$ (μM) cellular assay |
|---|---|---|---|---|
| 135 | 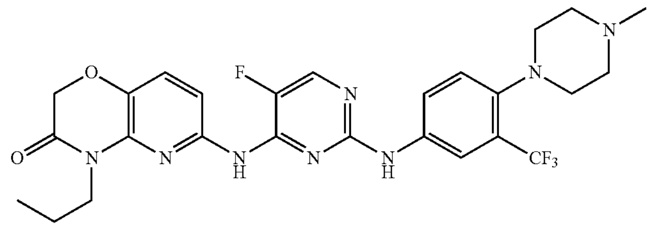 [SMILES: CCCN1C(=O)COc2ccc(Nc3nc(Nc4ccc(N5CCN(C)CC5)c(C(F)(F)F)c4)ncc3F)nc21] | 6-(5-fluoro-2-(4-(4-methylpiperazin-1-yl)-3-(trifluoromethyl)phenylamino)pyrimidin-4-ylamino)-4-propyl-2H-pyrido[3,2-b][1,4]oxazin-3(4H)-one | D | D |
| 136 | 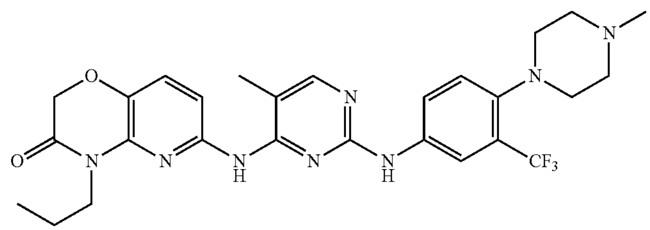 [SMILES: CCCN1C(=O)COc2ccc(Nc3nc(Nc4ccc(N5CCN(C)CC5)c(C(F)(F)F)c4)ncc3C)nc21] | 6-(5-methyl-2-(4-(4-methylpiperazin-1-yl)-3-(trifluoromethyl)phenylamino)pyrimidin-4-ylamino)-4-propyl-2H-pyrido[3,2-b][1,4]oxazin-3(4H)-one | D | D |
| 137 | 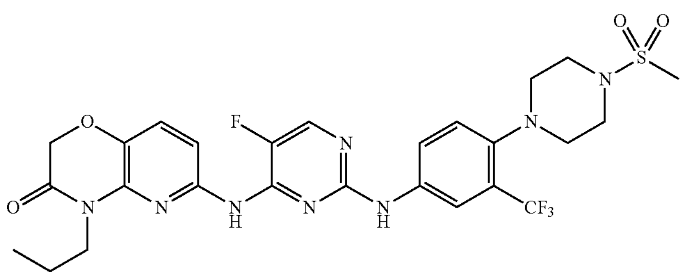 [SMILES: CCCN1C(=O)COc2ccc(Nc3nc(Nc4ccc(N5CCN(S(C)(=O)=O)CC5)c(C(F)(F)F)c4)ncc3F)nc21] | 6-(5-fluoro-2-(4-(4-(methylsulfonyl)piperazin-1-yl)-3-(trifluoromethyl)phenylamino)pyrimidin-4-ylamino)-4-propyl-2H-pyrido[3,2-b][1,4]oxazin-3(4H)-one | D | D |
| 138 | 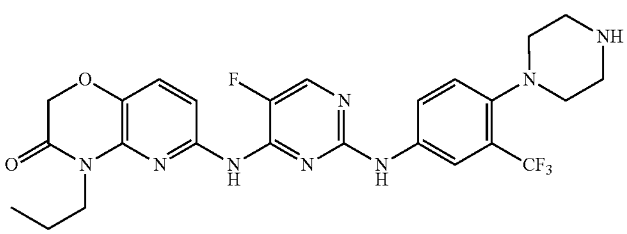 [SMILES: CCCN1C(=O)COc2ccc(Nc3nc(Nc4ccc(N5CCNCC5)c(C(F)(F)F)c4)ncc3F)nc21] | 6-(5-fluoro-2-(4-(piperazin-1-yl)-3-(trifluoromethyl)phenylamino)pyrimidin-4-ylamino)-4-propyl-2H-pyrido[3,2-b][1,4]oxazin-3(4H)-one | D | D |
| 139 | 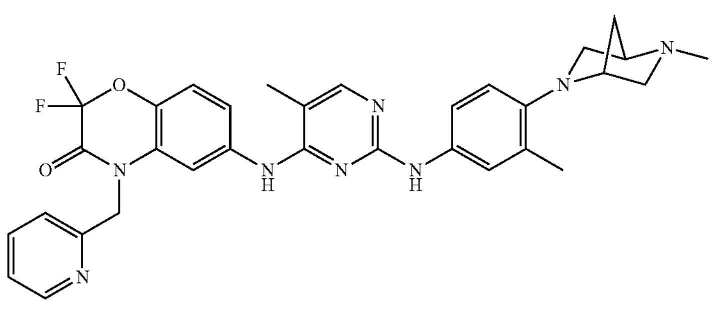 [SMILES: Cc1cc(Nc2ncc(C)c(Nc3ccc4c(c3)N(Cc3ccccn3)C(=O)C(F)(F)O4)n2)ccc1N1CC2CC1CN2C] | 2,2-difluoro-6-(5-methyl-2-(3-methyl-4-(5-methyl-2,5-diazabicyclo[2.2.1]heptan-2-yl)phenylamino)pyrimidin-4-ylamino)-4-(pyridin-2-ylmethyl)-2H-benzo[b][1,4]oxazin-3(4H)-one | D | C |
| 140 | 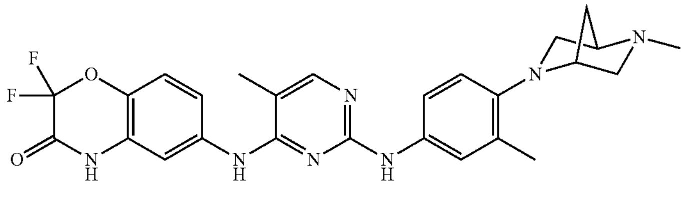 [SMILES: Cc1cc(Nc2ncc(C)c(Nc3ccc4c(c3)NC(=O)C(F)(F)O4)n2)ccc1N1CC2CC1CN2C] | 2,2-difluoro-6-(5-methyl-2-(3-methyl-4-(5-methyl-2,5-diazabicyclo[2.2.1]heptan-2-yl)phenylamino)pyrimidin-4-ylamino)-2H-benzo[b][1,4]oxazin-3(4H)-one | | |

TABLE 1-continued

| # | Structure | Name | PLK1 IC$_{50}$ (μM) biochemical assay | PLK1 IC$_{50}$ (μM) cellular assay |
|---|---|---|---|---|
| 141 | 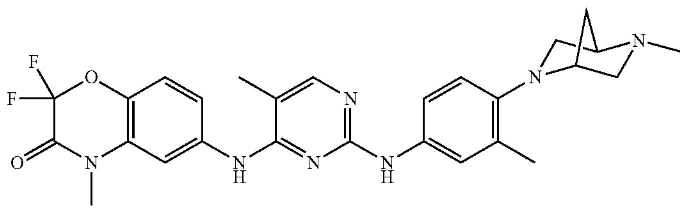 [SMILES: Cc1cc(Nc2ncc(C)c(Nc3ccc4c(c3)N(C)C(=O)C(F)(F)O4)n2)ccc1N1CC2CC1CN2C] | 2,2-difluoro-4-methyl-6-(5-methyl-2-(3-methyl-4-(5-methyl-2,5-diazabicyclo[2.2.1]heptan-2-yl)phenylamino)pyrimidin-4-ylamino)-2H-benzo[b][1,4]oxazin-3(4H)-one | | |
| 142 | 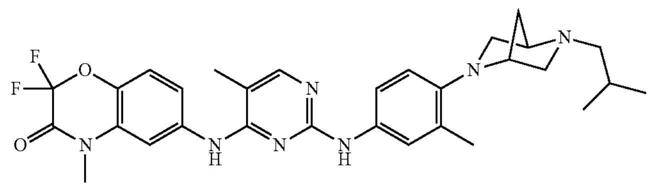 [SMILES: Cc1cc(Nc2ncc(C)c(Nc3ccc4c(c3)N(C)C(=O)C(F)(F)O4)n2)ccc1N1CC2CC1CN2CC(C)C] | 2,2-difluoro-6-(2-(4-(5-isobutyl-2,5-diazabicyclo[2.2.1]heptan-2-yl)-3-methylphenylamino)-5-methylpyrimidin-4-ylamino)-4-methyl-2H-benzo[b][1,4]oxazin-3(4H)-one | | |
| 143 | 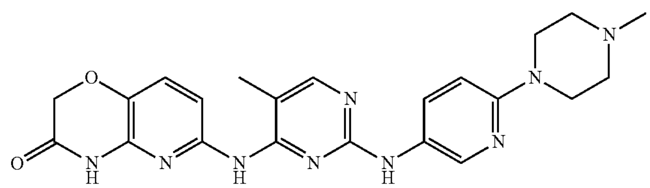 [SMILES: Cc1cnc(Nc2ccc(N3CCN(C)CC3)nc2)nc1Nc1ccc2c(n1)NC(=O)CO2] | 6-(5-methyl-2-(6-(4-methylpiperazin-1-yl)pyridin-3-ylamino)pyrimidin-4-ylamino)-2H-pyrido[3,2-b][1,4]oxazin-3(4H)-one | | |
| 144 | 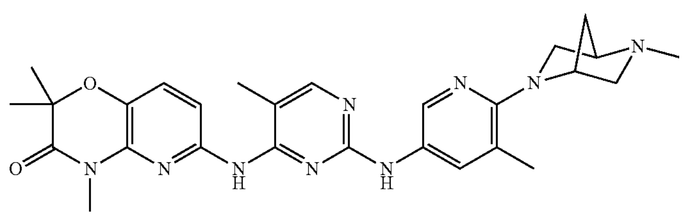 | 2,2,4-trimethyl-6-(5-methyl-2-(5-methyl-6-(5-methyl-2,5-diazabicyclo[2.2.1]heptan-2-yl)pyridin-3-ylamino)pyrimidin-4-ylamino)-2H-pyrido[3,2-b][1,4]oxazin-3(4H)-one | | |
| 145 | 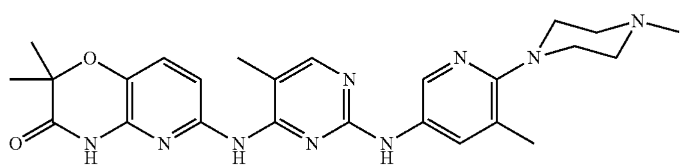 | 2,2-dimethyl-6-(5-methyl-2-(5-methyl-6-(4-methylpiperazin-1-yl)pyridin-3-ylamino)pyrimidin-4-ylamino)-2H-pyrido[3,2-b][1,4]oxazin-3(4H)-one | | |
| 146 | 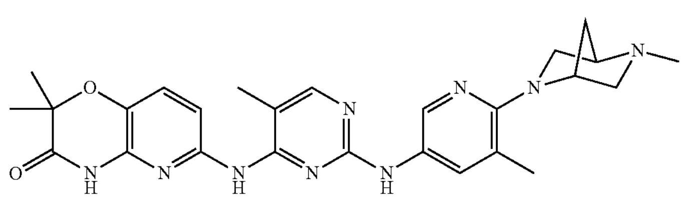 | 2,2-dimethyl-6-(5-methyl-2-(5-methyl-6-(5-methyl-2,5-diazabicyclo[2.2.1]heptan-2-yl)pyridin-3-ylamino)pyrimidin-4-ylamino)-2H-pyrido[3,2-b][1,4]oxazin-3(4H)-one | | |
| 147 | 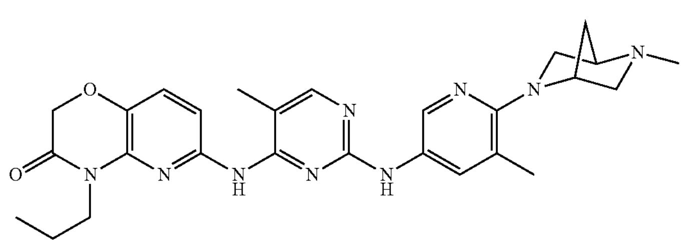 [SMILES: CCCN1C(=O)COc2ccc(Nc3nc(Nc4cnc(N5CC6CC5CN6C)c(C)c4)ncc3C)nc21] | 6-(5-methyl-2-(5-methyl-6-(5-methyl-2,5-diazabicyclo[2.2.1]heptan-2-yl)pyridin-3-ylamino)pyrimidin-4-ylamino)-4-propyl-2H-pyrido[3,2-b][1,4]oxazin-3(4H)-one | | |

TABLE 1-continued

| # | Structure | Name | PLK1 IC$_{50}$ (µM) biochemical assay | PLK1 IC$_{50}$ (µM) cellular assay |
|---|---|---|---|---|
| 148 | 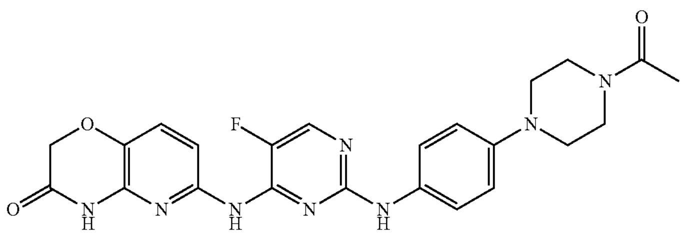 [SMILES: CC(=O)N1CCN(c2ccc(Nc3ncc(F)c(Nc4ccc5c(n4)NC(=O)CO5)n3)cc2)CC1] | 6-(2-(4-(4-acetyl-piperazin-1-yl)phenyl-amino)-5-fluoropyrimidin-4-ylamino)-2H-pyrido[3,2-b][1,4]oxazin-3(4H)-one | | |
| 149 | 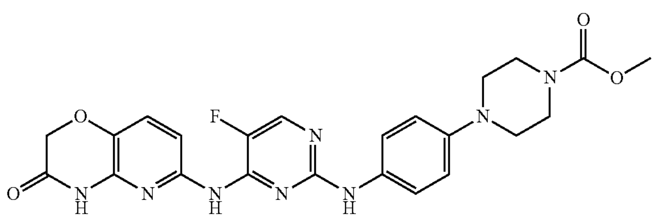 [SMILES: COC(=O)N1CCN(c2ccc(Nc3ncc(F)c(Nc4ccc5c(n4)NC(=O)CO5)n3)cc2)CC1] | methyl 4-(4-(5-fluoro-4-(3-oxo-3,4-dihydro-2H-pyrido[3,2-b][1,4]oxazin-6-ylamino)pyrimidin-2-ylamino)phenyl)piperazine-1-carboxylate | | |
| 150 | 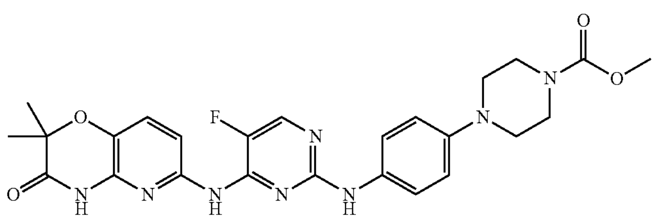 | methyl 4-(4-(4-(2,2-dimethyl-3-oxo-3,4-dihydro-2H-pyrido[3,2-b][1,4]oxazin-6-ylamino)-5-fluoro-pyrimidin-2-ylamino)phenyl)piperazine-1-carboxylate | | |
| 151 | 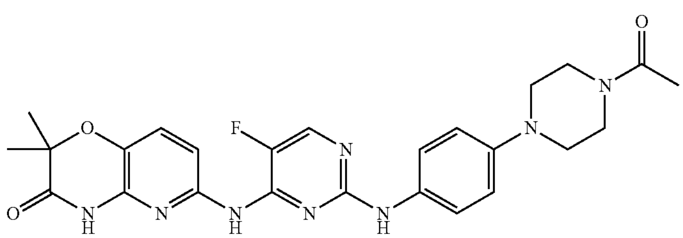 [SMILES: CC(=O)N1CCN(c2ccc(Nc3ncc(F)c(Nc4ccc5c(n4)NC(=O)C(C)(C)O5)n3)cc2)CC1] | 6-(2-(4-(4-acetyl-piperazin-1-yl)phenyl-amino)-5-fluoropyrimidin-4-ylamino)-2,2-dimethyl-2H-pyrido[3,2-b][1,4]oxazin-3(4H)-one | | |
| 152 | 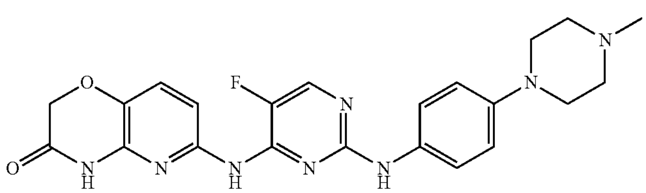 [SMILES: CN1CCN(c2ccc(Nc3ncc(F)c(Nc4ccc5c(n4)NC(=O)CO5)n3)cc2)CC1] | 6-(5-fluoro-2-(4-(4-methylpiperazin-1-yl)phenylamino)pyrimidin-4-ylamino)-2H-pyrido[3,2-b][1,4]oxazin-3(4H)-one | | |
| 153 | 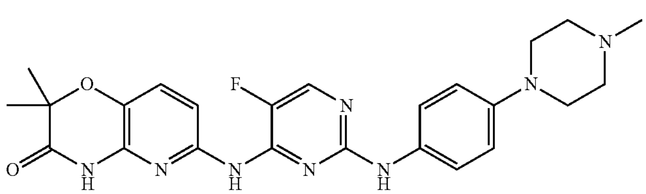 | 6-(5-fluoro-2-(4-(4-methylpiperazin-1-yl)phenylamino)pyrimidin-4-ylamino)-2,2-dimethyl-2H-pyrido[3,2-b][1,4]oxazin-3(4H)-one | | |

TABLE 1-continued

| # | Structure | Name | PLK1 IC$_{50}$ (μM) biochemical assay | PLK1 IC$_{50}$ (μM) cellular assay |
|---|---|---|---|---|
| 154 | 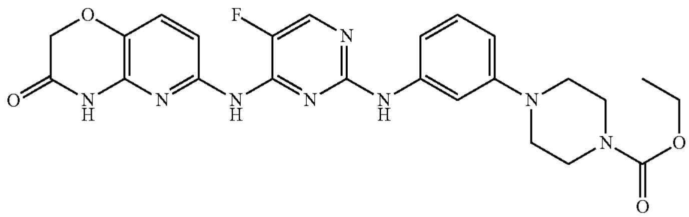 [SMILES: CCOC(=O)N1CCN(c2cccc(Nc3ncc(F)c(Nc4ccc5c(n4)NC(=O)CO5)n3)c2)CC1] | ethyl 4-(3-(5-fluoro-4-(3-oxo-3,4-dihydro-2H-pyrido[3,2-b][1,4]oxazin-6-ylamino)pyrimidin-2-ylamino)phenyl)piperazine-1-carboxylate | | |
| 155 | 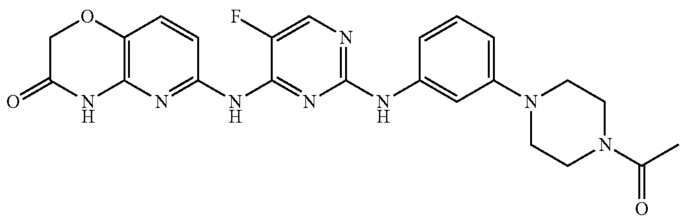 [SMILES: CC(=O)N1CCN(c2cccc(Nc3ncc(F)c(Nc4ccc5c(n4)NC(=O)CO5)n3)c2)CC1] | 6-(2-(3-(4-acetyl-piperazin-1-yl)phenylamino)-5-fluoropyrimidin-4-ylamino)-2H-pyrido[3,2-b][1,4]oxazin-3(4H)-one | | |
| 156 | 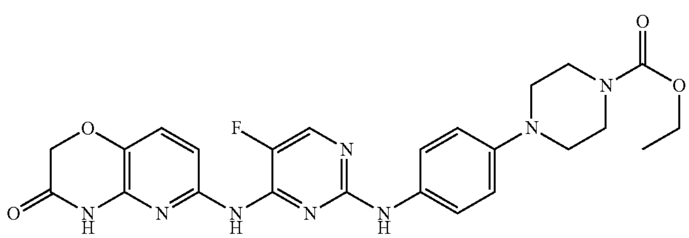 [SMILES: CCOC(=O)N1CCN(c2ccc(Nc3ncc(F)c(Nc4ccc5c(n4)NC(=O)CO5)n3)cc2)CC1] | ethyl 4-(4-(5-fluoro-4-(3-oxo-3,4-dihydro-2H-pyrido[3,2-b][1,4]oxazin-6-ylamino)pyrimidin-2-ylamino)phenyl)piperazine-1-carboxylate | | |
| 157 | 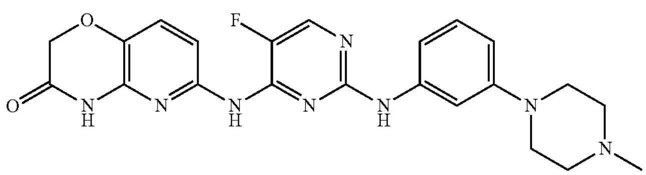 [SMILES: CN1CCN(c2cccc(Nc3ncc(F)c(Nc4ccc5c(n4)NC(=O)CO5)n3)c2)CC1] | 6-(5-fluoro-2-(3-(4-methylpiperazin-1-yl)phenylamino)pyrimidin-4-ylamino)-2H-pyrido[3,2-b][1,4]oxazin-3(4H)-one | A | A |
| 158 | 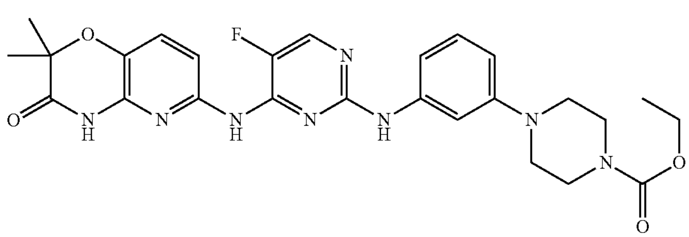 [SMILES: CCOC(=O)N1CCN(c2cccc(Nc3ncc(F)c(Nc4ccc5c(n4)NC(=O)C(C)(C)O5)n3)c2)CC1] | ethyl 4-(3-(4-(2,2-dimethyl-3-oxo-3,4-dihydro-2H-pyrido[3,2-b][1,4]oxazin-6-ylamino)-5-fluoropyrimidin-2-ylamino)phenyl)piperazine-1-carboxylate | | |
| 159 | 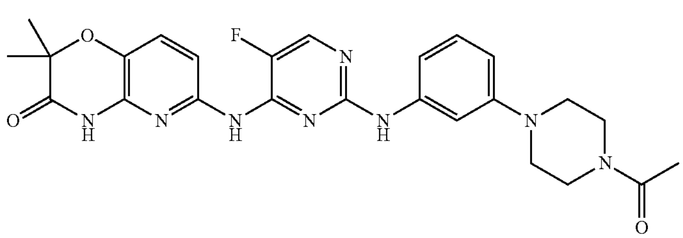 [SMILES: CC(=O)N1CCN(c2cccc(Nc3ncc(F)c(Nc4ccc5c(n4)NC(=O)C(C)(C)O5)n3)c2)CC1] | 6-(2-(3-(4-acetylpiperazin-1-yl)phenylamino)-5-fluoropyrimidin-4-ylamino)-2,2-dimethyl-2H-pyrido[3,2-b][1,4]oxazin-3(4H)-one | | |

TABLE 1-continued

| # | Structure | Name | PLK1 IC$_{50}$ (μM) biochemical assay | PLK1 IC$_{50}$ (μM) cellular assay |
|---|---|---|---|---|
| 160 | 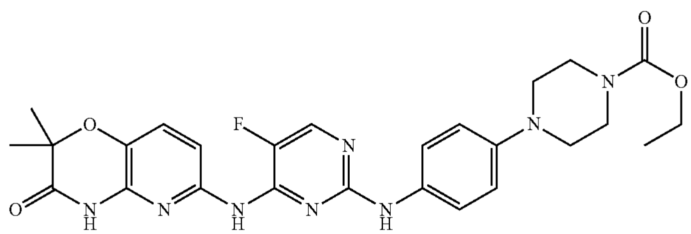 [SMILES: CCOC(=O)N1CCN(c2ccc(Nc3ncc(F)c(Nc4ccc5c(n4)NC(=O)C(C)(C)O5)n3)cc2)CC1] | ethyl 4-(4-(4-(2,2-dimethyl-3-oxo-3,4-dihydro-2H-pyrido[3,2-b][1,4]oxazin-6-ylamino)-5-fluoropyrimidin-2-ylamino)phenyl)piperazine-1-carboxylate | | |
| 161 | 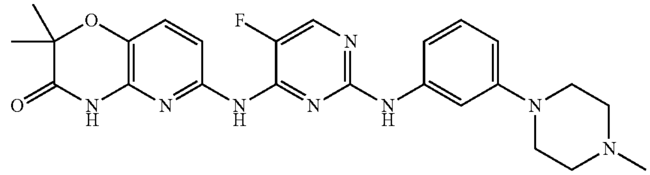 | 6-(5-fluoro-2-(3-(4-methylpiperazin-1-yl)phenylamino)pyrimidin-4-ylamino)-2,2-dimethyl-2H-pyrido[3,2-b][1,4]oxazin-3(4H)-one | A | B |
| 162 | 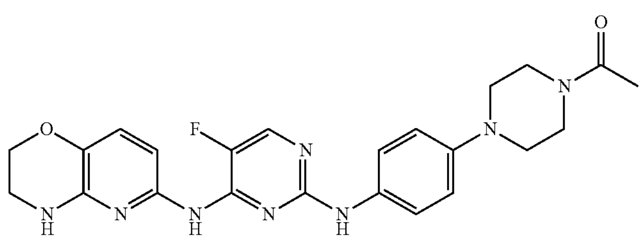 [SMILES: CC(=O)N1CCN(c2ccc(Nc3ncc(F)c(Nc4ccc5c(n4)NCCO5)n3)cc2)CC1] | 1-(4-(4-(4-(3,4-dihydro-2H-pyrido[3,2-b][1,4]oxazin-6-ylamino)-5-fluoropyrimidin-2-ylamino)phenyl)piperazin-1-yl)ethanone | | |
| 163 | 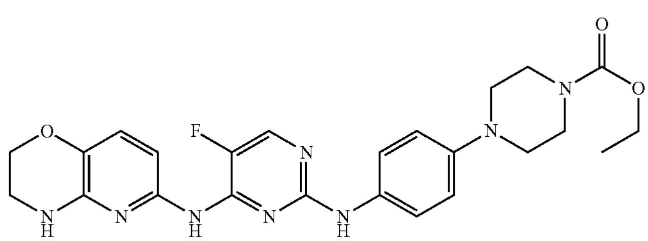 [SMILES: CCOC(=O)N1CCN(c2ccc(Nc3ncc(F)c(Nc4ccc5c(n4)NCCO5)n3)cc2)CC1] | ethyl 4-(4-(4-(3,4-dihydro-2H-pyrido[3,2-b][1,4]oxazin-6-ylamino)-5-fluoropyrimidin-2-ylamino)phenyl)piperazine-1-carboxylate | | D |
| 164 | 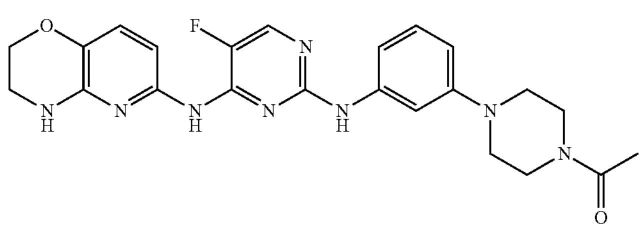 [SMILES: CC(=O)N1CCN(c2cccc(Nc3ncc(F)c(Nc4ccc5c(n4)NCCO5)n3)c2)CC1] | 1-(4-(3-(4-(3,4-dihydro-2H-pyrido[3,2-b][1,4]oxazin-6-ylamino)-5-fluoropyrimidin-2-ylamino)phenyl)piperazin-1-yl)ethanone | | D |
| 165 | 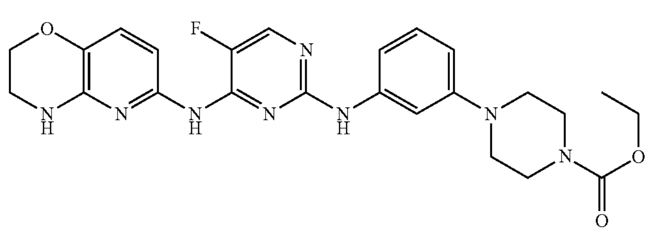 [SMILES: CCOC(=O)N1CCN(c2cccc(Nc3ncc(F)c(Nc4ccc5c(n4)NCCO5)n3)c2)CC1] | ethyl 4-(3-(4-(3,4-dihydro-2H-pyrido[3,2-b][1,4]oxazin-6-ylamino)-5-fluoropyrimidin-2-ylamino)phenyl)piperazine-1-carboxylate | | D |

TABLE 1-continued

| # | Structure | Name | PLK1 IC$_{50}$ (µM) biochemical assay | PLK1 IC$_{50}$ (µM) cellular assay |
|---|-----------|------|---|---|
| 166 | 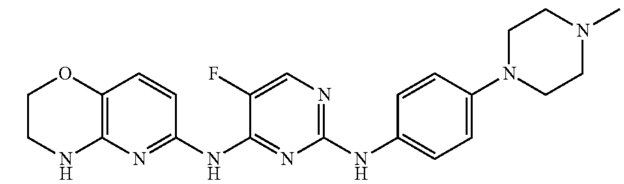 [SMILES: CN1CCN(c2ccc(Nc3ncc(F)c(Nc4ccc5c(n4)NCCO5)n3)cc2)CC1] | N4-(3,4-dihydro-2H-pyrido[3,2-b][1,4]oxazin-6-yl)-5-fluoro-N2-(4-(4-methylpiperazin-1-yl)phenyl)pyrimidine-2,4-diamine | | D |
| 167 | 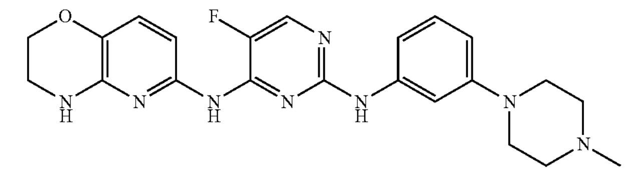 [SMILES: CN1CCN(c2cccc(Nc3ncc(F)c(Nc4ccc5c(n4)NCCO5)n3)c2)CC1] | N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine | A | A |
| 168 | p-TSA salt | N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine p-toluene sulfonic acid salt | A | A |
| 169 | HCl salt | N4-(3,4-dihydro-2H-pyrido[3,2-b][1,4]oxazin-6-yl)-5-fluoro-N2-(3-(4-methylpiperazin-1-yl)phenyl)pyrimidine-2,4-diamine hydrochloride salt | A | A |
| 170 | 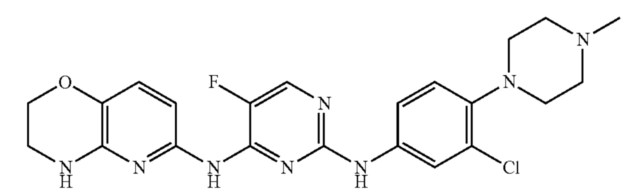 [SMILES: CN1CCN(c2ccc(Nc3ncc(F)c(Nc4ccc5c(n4)NCCO5)n3)cc2Cl)CC1] | N2-(3-chloro-4-(4-methylpiperazin-1-yl)phenyl)-N4-(3,4-dihydro-2H-pyrido[3,2-b][1,4]oxazin-6-yl)-5-fluoropyrimidine-2,4-diamine | | |
| 171 | 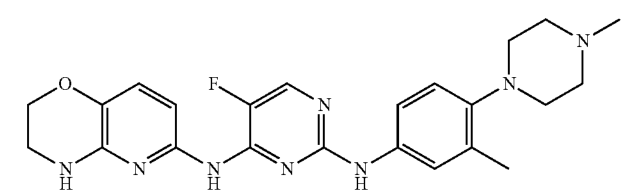 [SMILES: Cc1cc(Nc2ncc(F)c(Nc3ccc4c(n3)NCCO4)n2)ccc1N1CCN(C)CC1] | N4-(3,4-dihydro-2H-pyrido[3,2-b][1,4]oxazin-6-yl)-5-fluoro-N2-(3-methyl-4-(4-methylpiperazin-1-yl)phenyl)pyrimidine-2,4-diamine | | |
| 172 | 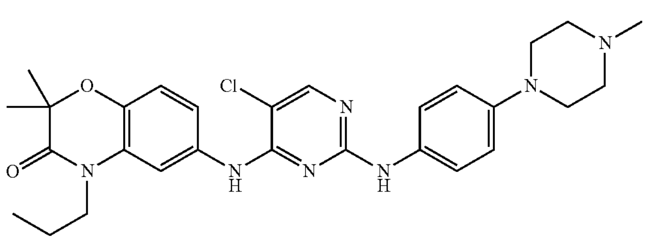 | 6-(5-chloro-2-(4-(4-methylpiperazin-1-yl)phenylamino)pyrimidin-4-ylamino)-2,2-dimethyl-4-propyl-2H-benzo[b][1,4]oxazin-3(4H)-one | | |

TABLE 1-continued

| # | Structure | Name | PLK1 IC$_{50}$ (µM) biochemical assay | PLK1 IC$_{50}$ (µM) cellular assay |
|---|---|---|---|---|
| 173 | 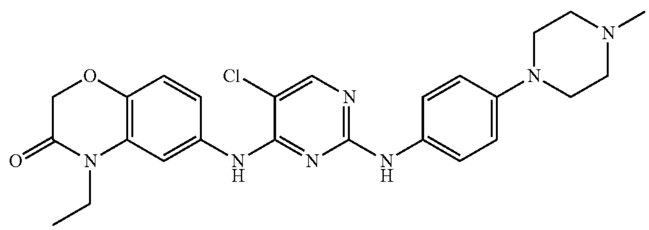 [SMILES: CCN1C(=O)COc2ccc(Nc3nc(Nc4ccc(N5CCN(C)CC5)cc4)ncc3Cl)cc21] | 6-(5-chloro-2-(4-(4-methylpiperazin-1-yl)phenylamino)pyrimidin-4-ylamino)-4-ethyl-2H-benzo[b][1,4]oxazin-3(4H)-one | B | B |
| 174 | 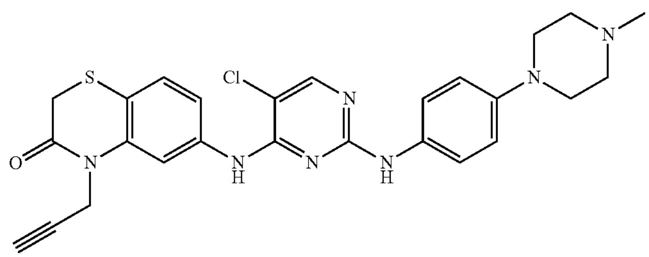 [SMILES: C#CCN1C(=O)CSc2ccc(Nc3nc(Nc4ccc(N5CCN(C)CC5)cc4)ncc3Cl)cc21] | 6-(5-chloro-2-(4-(4-methylpiperazin-1-yl)phenylamino)pyrimidin-4-ylamino)-4-(prop-2-ynyl)-2H-benzo[b][1,4]thiazin-3(4H)-one | | |
| 175 | 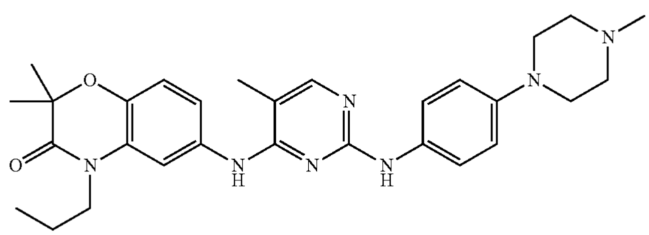 | 2,2-dimethyl-6-(5-methyl-2-(4-(4-methylpiperazin-1-yl)phenylamino)pyrimidin-4-ylamino)-4-propyl-2H-benzo[b][1,4]oxazin-3(4H)-one | | |
| 176 | 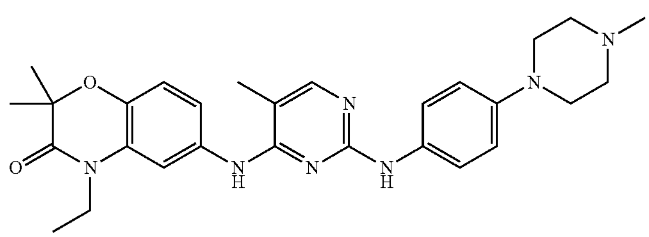 | 4-ethyl-2,2-dimethyl-6-(5-methyl-2-(4-(4-methylpiperazin-1-yl)phenylamino)pyrimidin-4-ylamino)-2H-benzo[b][1,4]oxazin-3(4H)-one | | |
| 177 | 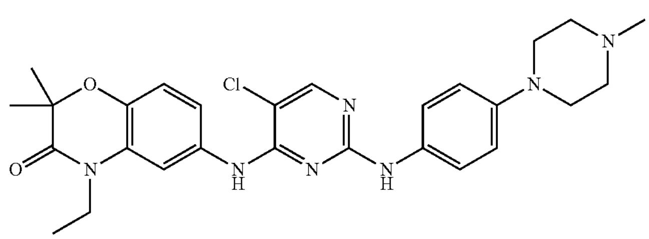 | 6-(5-chloro-2-(4-(4-methylpiperazin-1-yl)phenylamino)pyrimidin-4-ylamino)-4-ethyl-2,2-dimethyl-2H-benzo[b][1,4]oxazin-3(4H)-one | | |
| 178 | 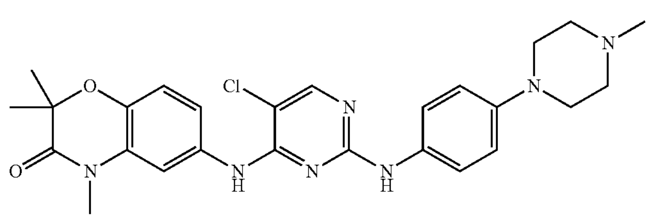 | 6-(5-chloro-2-(4-(4-methylpiperazin-1-yl)phenylamino)pyrimidin-4-ylamino)-2,2,4-trimethyl-2H-benzo[b][1,4]oxazin-3(4H)-one | | |

TABLE 1-continued

| # | Structure | Name | PLK1 IC$_{50}$ (μM) bio-chemical assay | PLK1 IC$_{50}$ (μM) cellular assay |
|---|---|---|---|---|
| 179 | 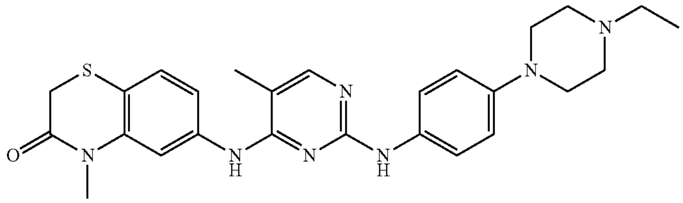 [SMILES: CCN1CCN(c2ccc(Nc3ncc(C)c(Nc4ccc5c(c4)N(C)C(=O)CS5)n3)cc2)CC1] | 6-(2-(4-(4-ethylpiperazin-1-yl)phenylamino)-5-methylpyrimidin-4-ylamino)-4-methyl-2H-benzo[b][1,4]thiazin-3(4H)-one | | |
| 180 | 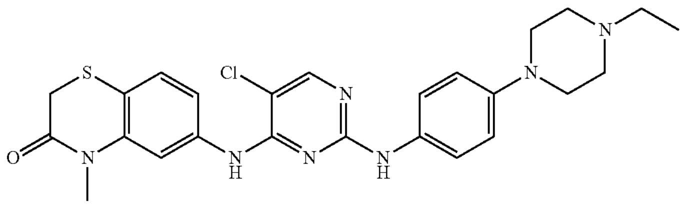 [SMILES: CCN1CCN(c2ccc(Nc3ncc(Cl)c(Nc4ccc5c(c4)N(C)C(=O)CS5)n3)cc2)CC1] | 6-(5-chloro-2-(4-(4-ethylpiperazin-1-yl)phenylamino)pyrimidin-4-ylamino)-4-methyl-2H-benzo[b][1,4]thiazin-3(4H)-one | | |
| 181 | 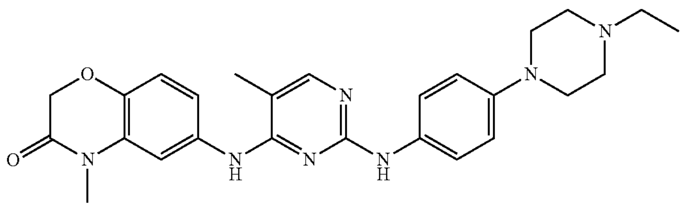 [SMILES: CCN1CCN(c2ccc(Nc3ncc(C)c(Nc4ccc5c(c4)N(C)C(=O)CO5)n3)cc2)CC1] | 6-(2-(4-(4-ethylpiperazin-1-yl)phenylamino)-5-methylpyrimidin-4-ylamino)-4-methyl-2H-benzo[b][1,4]oxazin-3(4H)-one | | |
| 182 | 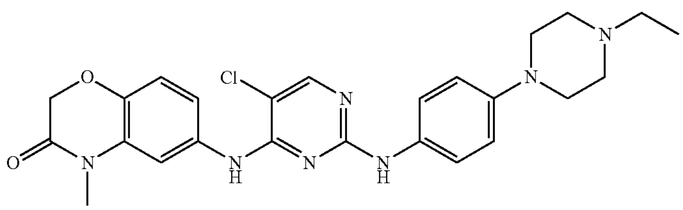 [SMILES: CCN1CCN(c2ccc(Nc3ncc(Cl)c(Nc4ccc5c(c4)N(C)C(=O)CO5)n3)cc2)CC1] | 6-(5-chloro-2-(4-(4-ethylpiperazin-1-yl)phenylamino)pyrimidin-4-ylamino)-4-methyl-2H-benzo[b][1,4]oxazin-3(4H)-one | | |
| 183 | 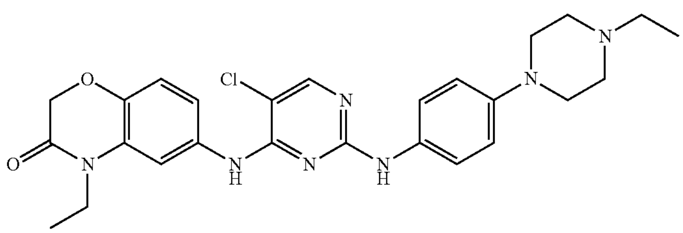 [SMILES: CCN1CCN(c2ccc(Nc3ncc(Cl)c(Nc4ccc5c(c4)N(CC)C(=O)CO5)n3)cc2)CC1] | 6-(5-chloro-2-(4-(4-ethylpiperazin-1-yl)phenylamino)pyrimidin-4-ylamino)-4-ethyl-2H-benzo[b][1,4]oxazin-3(4H)-one | B | B |
| 184 | 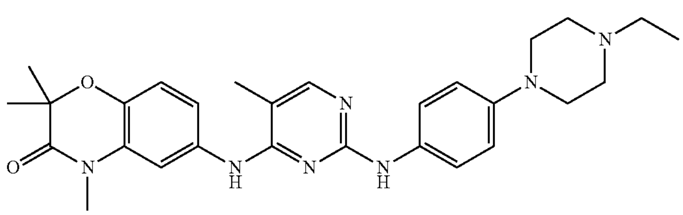 [SMILES: CCN1CCN(c2ccc(Nc3ncc(C)c(Nc4ccc5c(c4)N(C)C(=O)C(C)(C)O5)n3)cc2)CC1] | 6-(2-(4-(4-ethylpiperazin-1-yl)phenylamino)-5-methylpyrimidin-4-ylamino)-2,2,4-trimethyl-2H-benzo[b][1,4]oxazin-3(4H)-one | | |
| 185 | 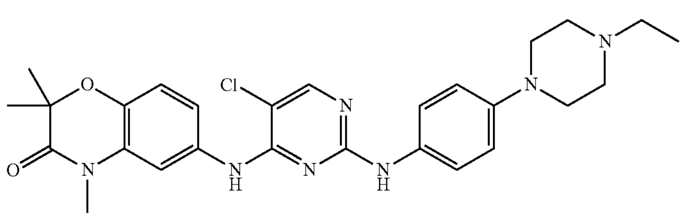 [SMILES: CCN1CCN(c2ccc(Nc3ncc(Cl)c(Nc4ccc5c(c4)N(C)C(=O)C(C)(C)O5)n3)cc2)CC1] | 6-(5-chloro-2-(4-(4-ethylpiperazin-1-yl)phenylamino)pyrimidin-4-ylamino)-2,2,4-trimethyl-2H-benzo[b][1,4]oxazin-3(4H)-one | | |

TABLE 1-continued

| # | Structure | Name | PLK1 IC$_{50}$ (μM) biochemical assay | PLK1 IC$_{50}$ (μM) cellular assay |
|---|---|---|---|---|
| 186 | 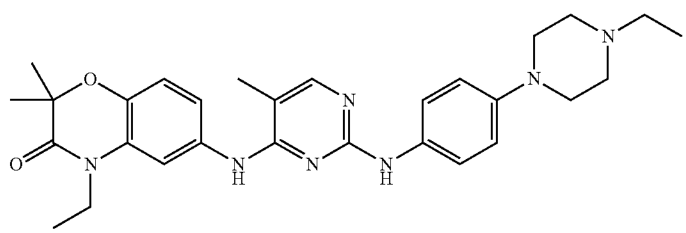 [SMILES: CCN1CCN(c2ccc(Nc3ncc(C)c(Nc4ccc5c(c4)N(CC)C(=O)C(C)(C)O5)n3)cc2)CC1] | 4-ethyl-6-(2-(4-(4-ethylpiperazin-1-yl)phenylamino)-5-methylpyrimidin-4-ylamino)-2,2-dimethyl-2H-benzo[b][1,4]oxazin-3(4H)-one | | |
| 187 | 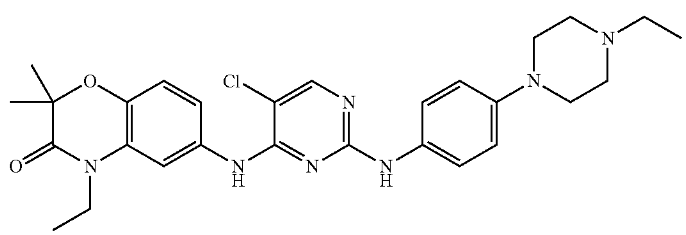 [SMILES: CCN1CCN(c2ccc(Nc3ncc(Cl)c(Nc4ccc5c(c4)N(CC)C(=O)C(C)(C)O5)n3)cc2)CC1] | 6-(5-chloro-2-(4-(4-ethylpiperazin-1-yl)phenylamino)pyrimidin-4-ylamino)-4-ethyl-2,2-dimethyl-2H-benzo[b][1,4]oxazin-3(4H)-one | | |
| 188 | 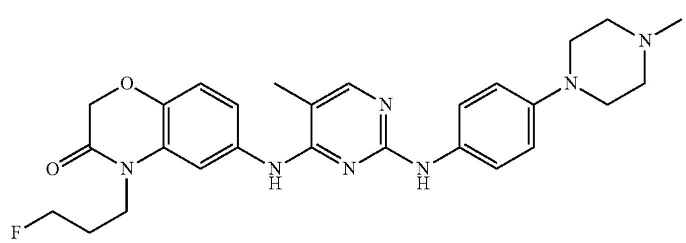 [SMILES: Cc1cnc(Nc2ccc(N3CCN(C)CC3)cc2)nc1Nc1ccc2c(c1)N(CCCF)C(=O)CO2] | 4-(3-fluoropropyl)-6-(5-methyl-2-(4-(4-methylpiperazin-1-yl)phenylamino)pyrimidin-4-ylamino)-2H-benzo[b][1,4]oxazin-3(4H)-one | B | B |
| 189 | 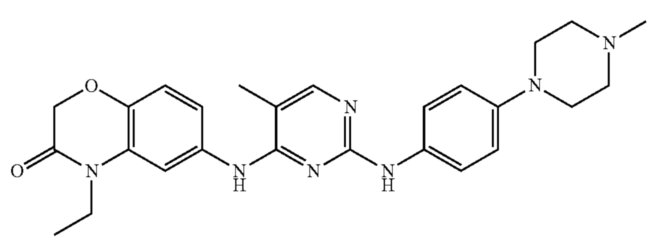 [SMILES: CCN1C(=O)COc2ccc(Nc3nc(Nc4ccc(N5CCN(C)CC5)cc4)ncc3C)cc21] | 4-ethyl-6-(5-methyl-2-(4-(4-methylpiperazin-1-yl)phenylamino)pyrimidin-4-ylamino)-2H-benzo[b][1,4]oxazin-3(4H)-one | B | B |
| 190 | 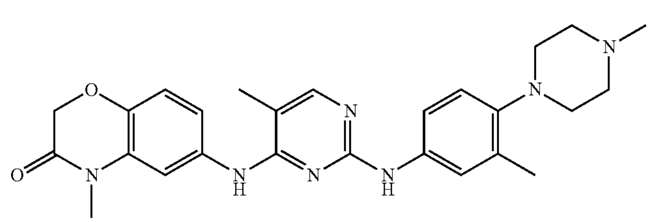 [SMILES: Cc1cc(Nc2ncc(C)c(Nc3ccc4c(c3)N(C)C(=O)CO4)n2)ccc1N1CCN(C)CC1] | 4-methyl-6-(5-methyl-2-(3-methyl-4-(4-methylpiperazin-1-yl)phenylamino)pyrimidin-4-ylamino)-2H-benzo[b][1,4]oxazin-3(4H)-one | | |
| 191 | 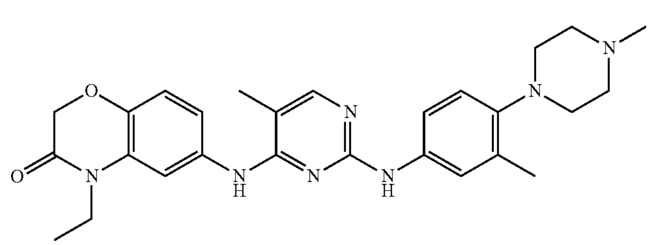 [SMILES: CCN1C(=O)COc2ccc(Nc3nc(Nc4ccc(N5CCN(C)CC5)c(C)c4)ncc3C)cc21] | 4-ethyl-6-(5-methyl-2-(3-methyl-4-(4-methylpiperazin-1-yl)phenylamino)pyrimidin-4-ylamino)-2H-benzo[b][1,4]oxazin-3(4H)-one | C | D |

TABLE 1-continued

| # | Structure | Name | PLK1 IC$_{50}$ (μM) biochemical assay | PLK1 IC$_{50}$ (μM) cellular assay |
|---|---|---|---|---|
| 192 | 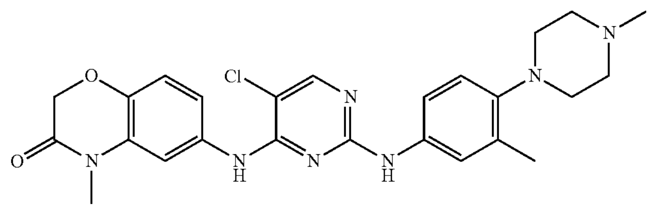 [SMILES: Cc1cc(Nc2ncc(Cl)c(Nc3ccc4c(c3)N(C)C(=O)CO4)n2)ccc1N1CCN(C)CC1] | 6-(5-chloro-2-(3-methyl-4-(4-methylpiperazin-1-yl)phenylamino)pyrimidin-4-ylamino)-4-methyl-2H-benzo[b][1,4]oxazin-3(4H)-one | | |
| 193 | 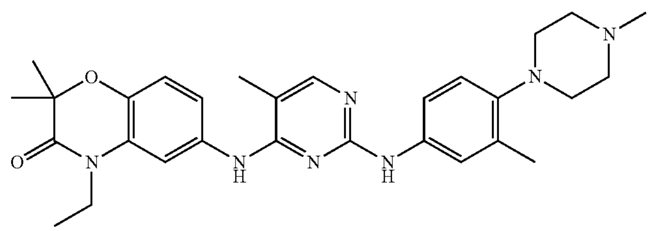 | 4-ethyl-2,2-dimethyl-6-(5-methyl-2-(3-methyl-4-(4-methylpiperazin-1-yl)phenylamino)pyrimidin-4-ylamino)-2H-benzo[b][1,4]oxazin-3(4H)-one | | |
| 194 | 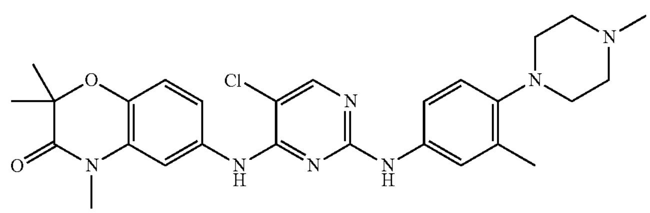 | 6-(5-chloro-2-(3-methyl-4-(4-methylpiperazin-1-yl)phenylamino)pyrimidin-4-ylamino)-2,2,4-trimethyl-2H-benzo[b][1,4]oxazin-3(4H)-one | | |
| 195 | 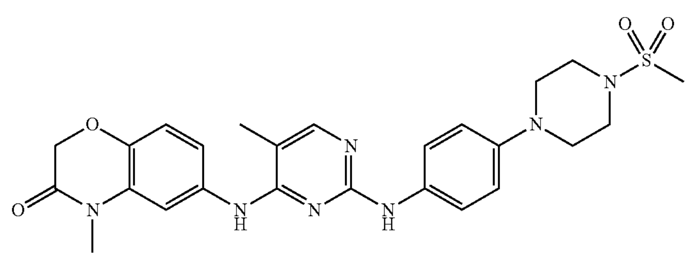 [SMILES: Cc1cnc(Nc2ccc(N3CCN(S(C)(=O)=O)CC3)cc2)nc1Nc1ccc2c(c1)N(C)C(=O)CO2] | 4-methyl-6-(5-methyl-2-(4-(4-(methylsulfonyl)piperazin-1-yl)phenylamino)pyrimidin-4-ylamino)-2H-benzo[b][1,4]oxazin-3(4H)-one | | |
| 196 | 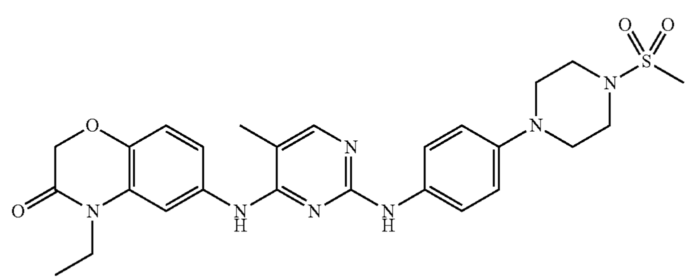 [SMILES: CCN1C(=O)COc2ccc(Nc3nc(Nc4ccc(N5CCN(S(C)(=O)=O)CC5)cc4)ncc3C)cc21] | 4-ethyl-6-(5-methyl-2-(4-(4-(methylsulfonyl)piperazin-1-yl)phenylamino)pyrimidin-4-ylamino)-2H-benzo[b][1,4]oxazin-3(4H)-one | B | C |
| 197 | 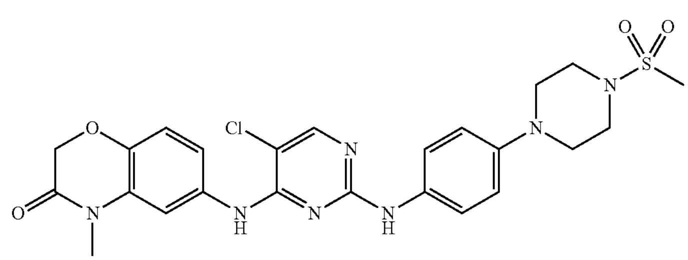 [SMILES: CN1C(=O)COc2ccc(Nc3nc(Nc4ccc(N5CCN(S(C)(=O)=O)CC5)cc4)ncc3Cl)cc21] | 6-(5-chloro-2-(4-(4-(methylsulfonyl)piperazin-1-yl)phenylamino)pyrimidin-4-ylamino)-4-methyl-2H-benzo[b][1,4]oxazin-3(4H)-one | D | B |

| # | Structure | Name | PLK1 IC$_{50}$ (μM) biochemical assay | PLK1 IC$_{50}$ (μM) cellular assay |
|---|---|---|---|---|
| 198 | 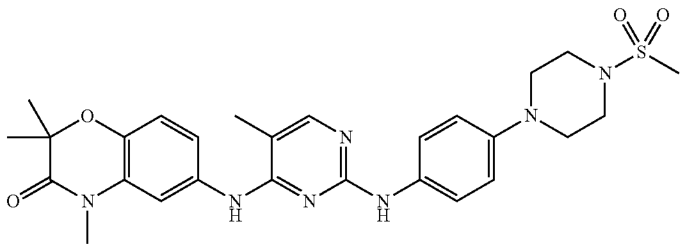 | 2,2,4-trimethyl-6-(5-methyl-2-(4-(4-(methylsulfonyl)piperazin-1-yl)phenylamino)pyrimidin-4-ylamino)-2H-benzo[b][1,4]oxazin-3(4H)-one | | |
| 199 | 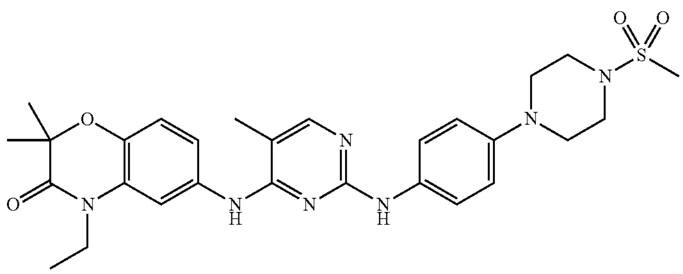 | 4-ethyl-2,2-dimethyl-6-(5-methyl-2-(4-(4-(methylsulfonyl)piperazin-1-yl)phenylamino)pyrimidin-4-ylamino)-2H-benzo[b][1,4]oxazin-3(4H)-one | | |
| 200 | 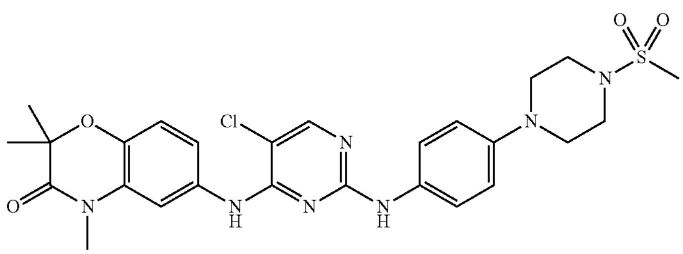 | 6-(5-chloro-2-(4-(4-(methylsulfonyl)piperazin-1-yl)phenylamino)pyrimidin-4-ylamino)-2,2,4-trimethyl-2H-benzo[b][1,4]oxazin-3(4H)-one | | |
| 201 | 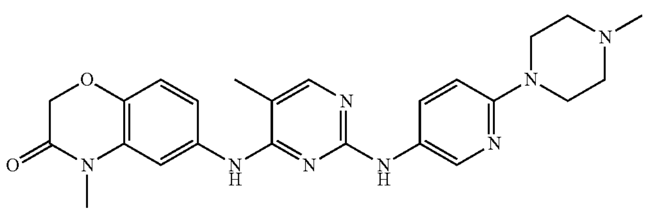 [SMILES: Cc1cnc(Nc2ccc(N3CCN(C)CC3)nc2)nc1Nc1ccc2c(c1)N(C)C(=O)CO2] | 4-methyl-6-(5-methyl-2-(6-(4-methylpiperazin-1-yl)pyridin-3-ylamino)pyrimidin-4-ylamino)-2H-benzo[b][1,4]oxazin-3(4H)-one | | |
| 202 | 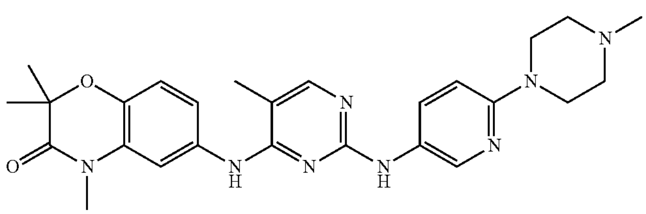 | 2,2,4-trimethyl-6-(5-methyl-2-(6-(4-methylpiperazin-1-yl)pyridin-3-ylamino)pyrimidin-4-ylamino)-2H-benzo[b][1,4]oxazin-3(4H)-one | | D |
| 203 | 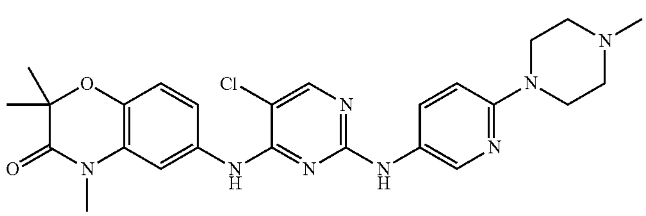 | 6-(5-chloro-2-(6-(4-methylpiperazin-1-yl)pyridin-3-ylamino)pyrimidin-4-ylamino)-2,2,4-trimethyl-2H-benzo[b][1,4]oxazin-3(4H)-one | | |

TABLE 1-continued

| # | Structure | Name | PLK1 IC$_{50}$ (μM) biochemical assay | PLK1 IC$_{50}$ (μM) cellular assay |
|---|---|---|---|---|
| 204 | 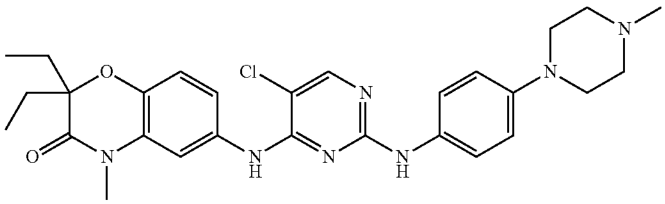 [SMILES: CCC1(CC)Oc2ccc(Nc3nc(Nc4ccc(N5CCN(C)CC5)cc4)ncc3Cl)cc2N(C)C1=O] | 6-(5-chloro-2-(4-(4-methylpiperazin-1-yl)phenylamino)pyrimidin-4-ylamino)-2,2-diethyl-4-methyl-2H-benzo[b][1,4]oxazin-3(4H)-one | | |
| 205 | 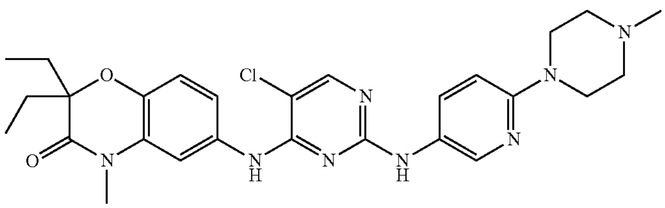 [SMILES: CCC1(CC)Oc2ccc(Nc3nc(Nc4ccc(N5CCN(C)CC5)nc4)ncc3Cl)cc2N(C)C1=O] | 6-(5-chloro-2-(6-(4-methylpiperazin-1-yl)pyridin-3-ylamino)pyrimidin-4-ylamino)-2,2-diethyl-4-methyl-2H-benzo[b][1,4]oxazin-3(4H)-one | | |
| 206 | 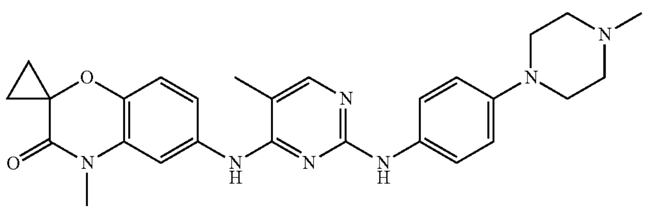 [SMILES: Cc1cnc(Nc2ccc(N3CCN(C)CC3)cc2)nc1Nc1ccc2c(c1)N(C)C(=O)C1(CC1)O2] | 4-methyl-6-(5-methyl-2-(4-(4-methylpiperazin-1-yl)phenyl-amino)pyrimidin-4-ylamino)spiro[benzo[b][1,4]oxazine-2,1'-cyclopropan]-3(4H)-one | | |
| 207 | 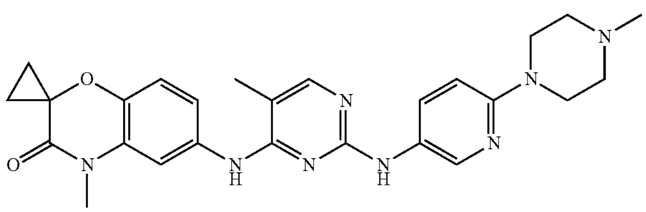 [SMILES: Cc1cnc(Nc2ccc(N3CCN(C)CC3)nc2)nc1Nc1ccc2c(c1)N(C)C(=O)C1(CC1)O2] | 4-methyl-6-(5-methyl-2-(6-(4-methylpiperazin-1-yl)pyridin-3-ylamino)pyrimidin-4-ylamino)spiro[benzo[b][1,4]oxazine-2,1'-cyclopropan]-3(4H)-one | | |
| 208 | 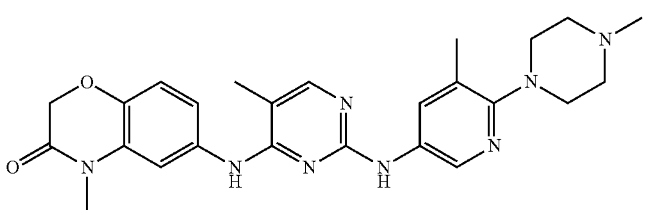 | 4-methyl-6-(5-methyl-2-(5-methyl-6-(4-methylpiperazin-1-yl)pyridin-3-ylamino)pyrimidin-4-ylamino)-2H-benzo[b][1,4]oxazin-3(4H)-one | | |
| 209 | 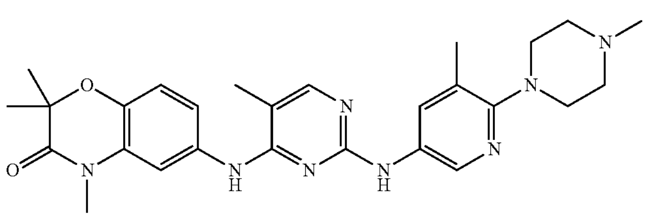 | 2,2,4-trimethyl-6-(5-methyl-2-(5-methyl-6-(4-methylpiperazin-1-yl)pyridin-3-ylamino)pyrimidin-4-ylamino)-2H-benzo[b][1,4]oxazin-3(4H)-one | | |
| 210 | 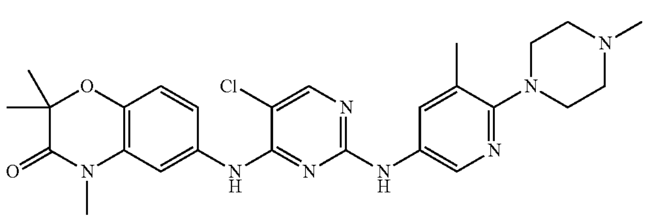 | 6-(5-chloro-2-(5-methyl-6-(4-methylpiperazin-1-yl)pyridin-3-ylamino)pyrimidin-4-ylamino)-2,2,4-trimethyl-2H-benzo[b][1,4]oxazin-3(4H)-one | | |

TABLE 1-continued

| # | Structure | Name | PLK1 IC$_{50}$ (µM) bio-chemical assay | PLK1 IC$_{50}$ (µM) cellular assay |
|---|---|---|---|---|
| 211 | 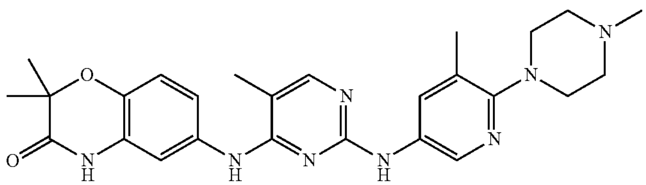 | 2,2-dimethyl-6-(5-methyl-2-(5-methyl-6-(4-methylpiperazin-1-yl)pyridin-3-ylamino)pyrimidin-4-ylamino)-2H-benzo[b][1,4]oxazin-3(4H)-one | | |
| 212 | 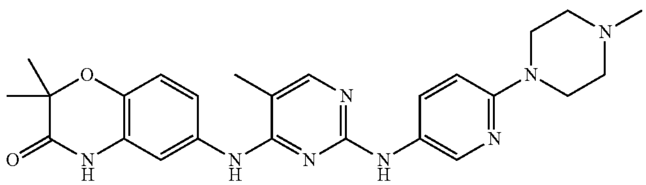 | 2,2-dimethyl-6-(5-methyl-2-(6-(4-methylpiperazin-1-yl)pyridin-3-ylamino)pyrimidin-4-ylamino)-2H-benzo[b][1,4]oxazin-3(4H)-one | | |

One of ordinary skill in the art will appreciate that many of the compounds and prodrugs described herein, as well as the various compound species specifically described and/or illustrated herein, may exhibit the phenomena of tautomerism, conformational isomerism, geometric isomerism and/or optical isomerism. For example, the compounds and prodrugs may include one or more chiral centers and/or double bonds and as a consequence may exist as stereoisomers, such as double-bond isomers (i.e., geometric isomers), enantiomers and diastereomers and mixtures thereof, such as racemic mixtures. As another example, the compounds and prodrugs may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. In cases of limited rotation around the 2,4-pyrimidinediamine core structure, atropisomers are also possible and are also specifically included in the compounds and/or prodrugs of the invention.

Depending upon the nature of the various substituents, the 2,4-pyrimidinediamine compounds and prodrugs may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (egg, methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The 2,4-pyrimidinediamine compounds and prodrugs, as well as the salts thereof, may also be in the form solvates (e.g., hydrates) and N-oxides, as are well-known in the art.\
Methods of Synthesis The 2,4-pyrimidinediamine compounds of the invention may be synthesized via a variety of different synthetic routes using commercially available starting materials and/or starting materials prepared by conventional synthetic methods. Suitable exemplary methods that may be routinely adapted to synthesize the 2,4-pyrimidinediamine compounds of the invention are found in U.S. Pat. No. 5,958,935, the disclosure of which is incorporated herein by reference. Specific examples describing the synthesis of numerous 2,4-pyrimidinediamine compounds, as well as intermediates therefore, are described in U.S. application Ser. No. 10/355,543, filed Jan. 31, 2003 (US2004/0029902A1), the contents of which are incorporated herein by reference. Suitable exemplary methods that may be routinely used and/or adapted to synthesize active 2,4-substituted pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO005/016893), the disclosures of which are incorporated herein by reference. All of the compounds described herein may be prepared by routine adaptation of these methods.

Specific exemplary synthetic methods for the 2,4-substituted pyrimidinediamines described herein are also described in Example 1, below. Those of skill in the art will also be able to readily adapt these examples for the synthesis of additional 2,4-substituted pyrimidinediamines as described herein.

An exemplary synthetic route that can be used to synthesize the 2,4-substituted pyrimidinediamines compounds of the invention are described in Scheme (I) below. One of ordinary skill in the art could routinely adapt this method to synthesize the 2,4-substituted pyrimidinediamine compounds described herein. As well, in the publications incorporated herein, numerous alternative synthesis examples are described in detail.

In one exemplary embodiment, the compounds can be synthesized from substituted or unsubstituted uracils as illustrated in Scheme (I), below:

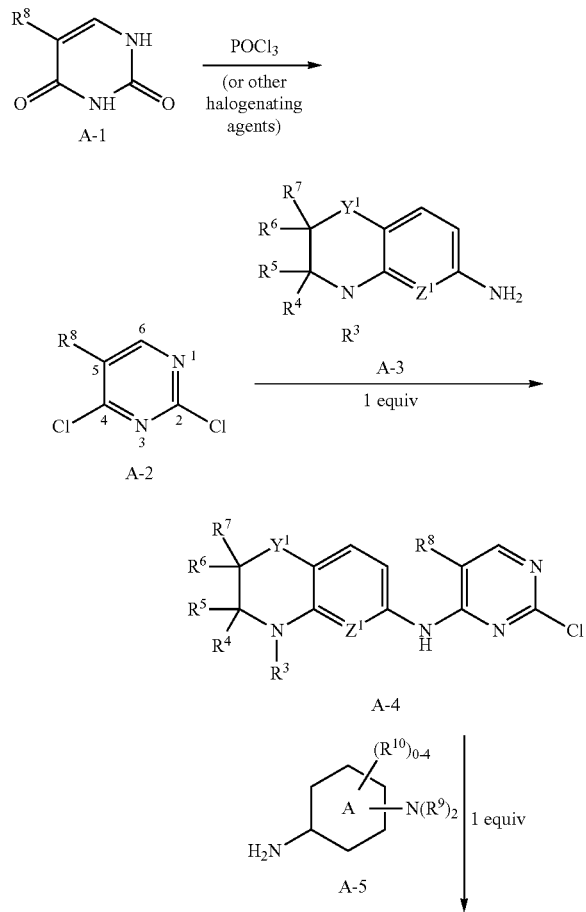

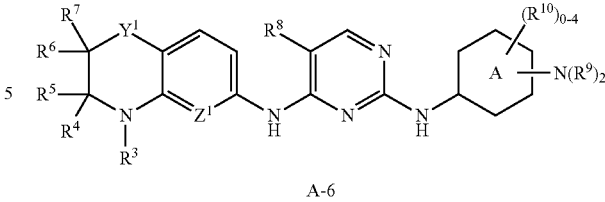

In Scheme (I), ring A, and the other variables are as defined herein for Formula I. According to Scheme (I), uracil A-1 is dihalogenated at the 2- and 4-positions using a standard halogenating agent such as $POCl_3$ (or other standard halogenating agent) under standard conditions to yield 2,4-dichloropyrimidine A-2. Depending upon the $R^8$ substituent, in pyrimidinediamine A-2, the chloride at the C4 position is more reactive towards nucleophiles than the chloride at the C2 position. This differential reactivity can be exploited to synthesize 2,4-pyrimidinediamines A-6 (and ultimately compounds of Formula I, via regioselective alkylation e.g., if $R^1$ and $R^2$ are not H (as they are in A-6)) by first reacting 2,4-dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6, a compound of Formula I, where $R^1$ and $R^2$ are H.

Typically, the C4 halide is more reactive towards nucleophiles, as illustrated in the Scheme. However, as will be recognized by skilled artisans, the identity of the X substituent may alter this reactivity. For example, when X is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions can be used: heat to 175° C. in ethanol for 5-20 min. In a Smith Reactor (Personal Chemistry, Uppsala, Sweden) in a sealed tube (at 20 bar pressure).

The uracil A-1 starting materials can be purchased from commercial sources or prepared using standard techniques of organic chemistry. Commercially available uracils that can be used as starting materials in Scheme (I) include, by way of example and not limitation, uracil (Aldrich #13,078-8; CAS Registry 66-22-8); 5-bromouracil (Aldrich #85, 247-3; CAS Registry 51-20-7; 5-fluorouracil (Aldrich #85, 847-1; CAS Registry 51-21-8); 5-iodouracil (Aldrich #85, 785-8; CAS Registry 696-07-1); 5-nitrouracil (Aldrich #85, 276-7; CAS Registry 611-08-5); 5-(trifluoromethyl)-uracil (Aldrich #22, 327-1; CAS Registry 54-20-6). Additional 5-substituted uracils are available from General Intermediates of Canada, Inc., Edmonton, Calif. and/or Interchim, Cedex, France, or can be prepared using standard techniques. Myriad textbook references teaching suitable synthetic methods are provided infra.

Amines A-3 and A-5 can be purchased from commercial sources or, alternatively, can be synthesized utilizing standard techniques. For example, suitable amines can be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines A-3 and A-5 and/or substituent $R^8$ on uracil A-1 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis,* 3d Edition, John Wiley & Sons, Inc., New York (1999) and the references cited therein (hereinafter "Greene & Wuts").

Thus, protecting group refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and additionally, in Harrison et al., *Compendium of Synthetic Organic Methods,* Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethane-sulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups) and allyl ethers.

Myriad references teaching methods useful for synthesizing pyrimidines generally, as well as starting materials described in Scheme (I) are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume 16, Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry,* 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclic Chemistry,* $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry,* $4^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

EXAMPLE 1

Ethyl 4-(3-(5-fluoro-4-(3-oxo-3,4-dihydro-2H-pyrido[3,2-b][1,4]oxazin-6-ylamino)pyrimidin-2-ylamino)phenyl) piperazine-1-carboxylate, compound number 154 in Table 1, was synthesized according to Scheme (I), using 6-amino-2H-pyrido[3,2-b][1,4]oxazin-3(4H)-one and 2,4-dichloro-5-fluorouracil (A-2 where $R^8$ is F), followed by addition of ethyl 4-(3-aminophenyl)piperazine-1-carboxylate to the corresponding 2-chloropyrimidine intermediate (A-4).

$^1$H NMR (CDCl3): d 1.14 (t, J=7.2 Hz, 3H), 3.00 (t, J=5.1 Hz, 4H), 3.46 (t, J=5.1 Hz, 4H), 4.00 (q, J=7.2 Hz, 2H), 4.47 (s, 2H), 6.55 (dd, J=1.8 and 8.4 Hz, 1H), 6.90 (dd, J=1.2 and 7.8 Hz, 1H), 6.98 (t, J=2.1 Hz, 1H), 7.04 (d, J=8.7 Hz, 1H), 7.08

The remaining compounds described herein were made in an analogous manner.

Utility

The presently disclosed compounds, including the various salts, prodrugs, hydrates and N-oxide forms, and pharmaceutical formulations thereof, may be used to treat diseases or conditions associated with a kinase activity, such as enhanced PLK1 activity. Thus, in a specific embodiment, the 2,4-pyrimidinediamine compounds (and the various forms described herein) may be used to treat disorders associated with abnormal cell proliferation in mammal subjects, including humans. The compound may act cytotoxically to kill the abnormally proliferating cells, or cytostatically to inhibit proliferation without killing the cell.

Methods generally include administering to the subject an amount of a compound of the invention, or a salt, prodrug, hydrate or N-oxide thereof, effective to treat the disorder. In one embodiment, the subject is a mammal, including, but not limited to, bovine, horse, feline, canine, rodent, or primate. In another embodiment, the subject is a human.

A variety of cellular proliferative disorders may be treated with the compounds of the present invention. In one embodiment, the compounds are used to treat various cancers in afflicted subjects. Cancers are traditionally classified based on the tissue and cell type from which the cancer cells originate. Carcinomas are considered cancers arising from epithelial cells while sarcomas are considered cancers arising from connective tissues or muscle. Other cancer types include leukemias, which arise from hematopoietic cells, and cancers of nervous system cells, which arise from neural tissue. For non-invasive tumors, adenomas are considered benign epithelial tumors with glandular organization while chondomas are benign tumor arising from cartilage. In the present invention, the described compounds may be used to treat proliferative disorders encompassed by carcinomas, sarcomas, leukemias, neural cell tumors, and non-invasive tumors.

In a specific embodiment, the compounds are used to treat solid tumors arising from various tissue types, including, but not limited to, cancers of the bone, breast, respiratory tract (e.g., bladder), brain reproductive organs, digestive tract, urinary tract, eye, liver, skin, head, neck, thyroid, parathyroid, and metastatic forms thereof.

Specific proliferative disorders include the following: a) proliferative disorders of the breast include, but are not limited to, invasive ductal carcinoma, invasive lobular carcinoma, ductal carcinoma, lobular carcinoma in situ, and metastatic breast cancer; b) proliferative disorders of the skin include, but are not limited to, basal cell carcinoma, squamous cell carcinoma, malignant melanoma, and Karposi's sarcoma; c) proliferative disorders of the respiratory tract include, but are not limited to, small cell and non-small cell lung carcinoma, bronchial adenoma, pleuropulmonary blastoma, and malignant mesothelioma; d) proliferative disorders of the brain include, but are not limited to, brain stem and hyptothalamic glioma, cerebellar and cerebral astrocytoma, medullablastoma, ependymal tumors, oligodendroglial, meningiomas, and neuroectodermal and pineal tumors; e) proliferative disorders of the male reproductive organs include, but are not limited to, prostate cancer, testicular cancer, and penile cancer f) proliferative disorders of the female reproductive organs include, but are not limited to, uterine cancer (endometrial), cervical, ovarian, vaginal, vulval cancers, uterine sarcoma, ovarian germ cell tumor; g) proliferative disorders of the digestive tract include, but are not limited to, anal, colon, colorectal, esophageal, gallbladder, stomach (gastric), pancreatic cancer, pancreatic cancer-Islet cell, rectal, small-intestine, and salivary gland cancers; h) proliferative disorders of the liver include, but are not limited to, hepatocellular carcinoma, cholangiocarcinoma, mixed hepatocellular cholangiocarcinoma, and primary liver cancer; i) proliferative disorders of the eye include, but are not limited to, intraocular melanoma, retinoblastoma, and rhabdomyosarcoma; j) proliferative disorders of the head and cancers include, but are not limited to, laryngeal, hypopharyngeal, nasopharyngeal, oropharyngeal cancers, and lip and oral cancer, squamous neck cancer, metastatic paranasal sinus cancer; k) proliferative disorders of the lymphomas include, but are not limited to, various T cell and B cell lymphomas, non-Hodgkin's lymphoma, cutaneous T cell lymphoma, Hodgkin's disease, and lymphoma of the central nervous system; l) leukemias include, but are not limited to, acute myeloid leukemia, acute lymphoblastic leukemia, chronic lymphocytic leukemia, chronic myelogenous leukemia, and hair cell leukemia, m) proliferative disorders of the thyroid include thyroid cancer, thymoma, and malignant thymoma; n) proliferative disorders of the urinary tract include, but are not limited to, bladder cancer; o) sarcomas include, but are not limited to, sarcoma of the soft tissue, osteosarcoma, malignant fibrous histiocytoma, lymphosarcoma, and rhabdomyosarcoma.

It is to be understood that the descriptions of proliferative disorders is not limited to the conditions described above, but encompasses other disorders characterized by uncontrolled growth and malignancy. It is further understood that proliferative disorders include various metastatic forms of the tumor and cancer types described herein. The compounds of the present invention may be tested for effectiveness against the disorders described herein, and a therapeutically effective regimen established. Effectiveness, as further described below, includes reduction or remission of the tumor, decreases in the rate of cell proliferation, or cytostatic or cytotoxic effect on cell growth.

Combination Therapies

The compounds of the present invention may be used alone, in combination with one another, or as an adjunct to, or in conjunction with, other established antiproliferative therapies. Thus, the compounds of the present invention may be used with traditional cancer therapies, such as ionization radiation in the form of gamma-rays and X-rays, delivered externally or internally by implantation of radioactive compounds, and as a follow-up to surgical removal of tumors.

In another aspect, the compounds of the present invention may be used with other chemotherapeutic agents useful for the disorder or condition being treated. These compounds may be administered simultaneously, sequentially, by the same route of administration, or by a different route.

In one embodiment, the present compounds may be used with other anti-cancer or cytotoxic agents. Various classes of anti-cancer and anti-neoplastic compounds include, but are not limited to, alkylating agents, antimetabolites, vinca alkyloids, taxanes, antibiotics, enzymes, cytokines, platinum coordination complexes, substituted ureas, tyrosine kinase inhibitors, hormones and hormone antagonists. Exemplary alkylating agents include, by way of example and not limitation, mechlorothamine, cyclophosphamide, ifosfamide, melphalan, chlorambucil, ethyleneimines, methylmelamines, alkyl sulfonates (for example, busulfan), and carmustine. Exemplary antimetabolites include, by way of example and not limitation, folic acid analogs, such as methotrexate; pyrimidine analog fluorouracil, cytosine arabinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as anti-neoplastic agents includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds, such as hydroxyprogesterone caproate and medroxyprogesterone; and anti-estrogen compounds, such as tamoxifen.

Additional chemotherapeutic agents useful in combination with the presently disclosed compounds include, without limitation, HDAC inhibitors (e.g., MGCD0103 and vorinostat), HSP 90 inhibitors (such as, 17-AAG), BCL-2 inhibitors, thalidomide, lenalidomide, mTOR inhibitors (such as, rapamycin, CCl-779), sorafenib, doxorubicine, gemcitabine, dexamethasone, melphalan, proteasome inhibitors (e.g., bortezomib, NPI052), monoclonal antibodies (such as, gemtuzumab, alemtuzumab, ibritumomab tiuxaetan, tositumomab, iodine-131 tositumomab, trastuzumab, bevacizumab, rituximab and anti-TRAIL death receptor antibodies), cytokines (such as interferon-alpha and interferon-gamma, interleukin-2, and GM-CSF), and the like.

These and other chemotherapeutic agents useful in treating cancer are described in the Merck Index, 13th Ed. (O'Neil M. J. et al., ed.) Merck Publishing Group (2001), "Commonly Used Antineoplastic Drugs", *The Merck Manuals Online Medical Library For HealthCare Professionals* at www.mercksource.com, and Goodman and Gilmans The Pharmacological Basis of Therapeutics, 10th Edition, Hardman, J. G. and Limbird, L. E. eds., pg. 1381-1287, McGraw Hill, (1996), each of which are incorporated by reference herein.

Additional anti-proliferative compounds useful in combination with the compounds of the present invention include, by way of example and not limitation, antibodies directed against growth factor receptors (for example, anti-Her2); antibodies for activating T cells (for example, anti-CTLA-4 antibodies); and cytokines such as interferon-alpha and interferon-gamma, interleukin-2, and GM-CSF.

Formulations and Administration

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stabilizers. The active compounds or prodrugs may be administered per se, or as pharmaceutical compositions, including an active compound or prodrug.

Pharmaceutical compositions including the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see Remington's Pharmaceutical Sciences, 15.sup.th Ed., Hoover, J. E. ed., Mack Publishing Co. (2003).

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc, as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges including gelatin) may be formulated containing a powder mix of the compound and a suitable powder base such as lactose or starch.

For ocular administration, the active compound(s) or prodrug(s) may be formulated as a solution, emulsion, suspension, etc, suitable for administration to the eye. A variety of vehicles suitable for administering compounds to the eye are known in the art. Specific none limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s), Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, include metal or plastic foil, such as a blister pack. The pack or dispenser device may be accompanied by instructions for administration.

Effective Dosages

The active compound(s) or prodrug(s) of the invention, or compositions thereof will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an IC50 of the particular compound as measured in an in vitro assay, such as the in vitro assays described in the Examples section. Calculating dosages to achieve such circulating blood or serum concentrations talking into account the bioavailability of the particular compound is well within the capabilities of skilled artisans. For guidance, the reader is referred to Fingi & Woodbury, "General Principles," In: Goodman and Gilman's The Pharmaceutical Basis of Therapeutics, Chapter 1, pp. 1-46, latest edition, Pagamonon Press, and the references cited therein.

Initial dosages may also be estimated from in vivo data, such as animal models. Animal models useful for testing the efficacy of compounds to treat or prevent the various diseases described above are well-known in the art. Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) LD50/ED50 effect is the therapeutic index (LD50 is the dose lethal to 50% of the population and ED50 is the dose therapeutically effective in 50% of the population). Compounds(s) that exhibit high therapeutic indices are preferred.

Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may include a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

EXAMPLES

The ability of compounds described herein to inhibit PLK1 was demonstrated in a biochemical PLK1 ELISA assay using an artificial PLK1 substrate and in a cellular assay using cultured human chronic myelogenous leukemia K562 cells overexpressing the natural PLK1 substrate, CDC25C protein. Inhibition of PLK1 was measured by quantifying phosphorylation of PLK1 substrates using chemiluminescent and fluorogenic probes. The protocols for these assays are provided below.

The $IC_{50}$ values for tested compounds are presented in Table 1, both for the biochemical non-cellular ELISA assay, and for the cellular assay.

Many compounds exhibit $IC_{50}$ values of less than 10 μM in biochemical ELISA assay. These compounds include compound Nos. 3, 4-6, 15-21, 23-30, 32-56, 95-97, 101, 107-111, 114-116, 120, 122, 125, 127-134, 157, 161, 167-169, 173, 183, 188, 189, 191 and 196. Of these, many compounds exhibit $IC_{50}$ values of less than 0.01 μM in biochemical ELISA assay: compound Nos. 5, 6, 17, 19, 25, 26, 36, 40, 42, 48, 49, 50, 51, 55, 122, 127-130, 134, 157, and 168-169.

For many compounds inhibition of Aurora B kinase was measured simultaneously with PLK1 inhibition in a cellular assay. For many compounds high PLK1/Aurora B selectivities were observed (for example representative compounds exhibited a significantly lower $IC_{50}$ for PLK1 than $IC_{50}$ for Aurora B). For example, in one aspect the disclosed PLK1 inhibitors inhibit PLK1 at least about 1.2-fold more potently than they inhibit Aurora B, such as from about 1.2-fold to about 1000-fold, from about 2-fold to about 500-fold or from about 10-fold to about 100-fold more potently.

In Vitro PLK1 ELISA Assay

1. Preparation of Assay Plates.

Costar 96-well black or white solid flat high binding plates (Fisher Scientific, Catalog No. 07-200-591) were coated with Neutravidin (Pierce, Catalog No. 31000) using the following protocol. A 0.01 mg/mL solution of Neutravidin in 1× Phosphate Buffered Saline ("PBS", Cellgro/Mediatech, Catalog No. 21-040-CV) was added to each well (100 μL/well) and was incubated for 18-24 hours at 4° C. The plates were then washed with 1× Phosphate Buffer Saline—Tween ("PBST", Calbiochem, Catalog No. 524653) buffer using a plate washer. The plates were treated with bovine serum albumin ("BSA", Sigma, Catalog No. A7906) to block non-specific binding sites, by adding a 2% BSA solution in 1×PBST buffer to each well (100 μL/well) and incubating the plates for 1 hour at room temperature. The plates were then washed with 1×PBST buffer using a plate washer.

2. PLK1-Catalyzed Phosphorylation Reaction

An aqueous buffer solution A having the following composition was prepared:

20 mM HEPES (Cellgro/Mediatech, Catalog No. 25-060Ci), pH 7.2;

5 mM $MgCl_2$ (Sigma, Catalog No. M2393);

2 mM $MnCl_2.4H_2O$ (EM Biosciences, Catalog No. MX0185-2);

0.01% Brij-35 (Sigma, Catalog No. B4184);

1 mM Dithiothreitol ("DTT", Fluka, Catalog No. B4184).

Next, the substrate solution B was prepared by adding 2.6 μL of 10 mM ATP (Sigma, Catalog No. A7699) and 6.4 μL of the 1 mM PLK1 substrate, CHK2-derived peptide Biotin-SSLETVSTQELYSIP (custom synthesized at Anaspec) SEQ ID: No. 1, to 4691 μL of the buffer solution A. The concentration of the ATP in solution B is 5.44 μM (1.36×); the concentration of the PLK1 substrate in solution B is 1.36 μM (1.36×).

Compound solutions C of varying concentrations for each compound were prepared by dissolving each compound in dimethylsulfoxide (DMSO, Sigma, Catalog No. D2650) to varying concentrations, followed by adding 2 μL of each solution to 38 μL of the buffer solution A, thereby forming 10× compound solutions in 5% DMSO.

A PLK1 solution D was prepared by adding 8.4 μL of 100 μg/mL PLK1 (Cell Signalling, Catalog No. 7728) to 1392 μL of the buffer solution A, thereby forming 0.6 μg/mL (6×) PLK1 solution.

The aqueous 1.36× substrate solution B was added to each well (44 μL/well) resulting in binding of the substrate to the plate via biotin/neutravidin interaction. Then 10× compound solutions C for each tested compound at each tested concentration were added to each well (6 μL/well). Next, 6×PLK1 solution D was added to each well (10 μL/well).

The final concentrations of tested compounds in each well were 10 μM, 3.3 μM, 1.1 μM, 0.36 μM, 0.12 μM, 0.04 μM, 0.014 μM, and 0.005 μM.

The obtained reaction mixtures were incubated in the wells for 45 minutes at room temperature, allowing PLK1-catalyzed phosphorylation of the substrate to proceed. The plates were then washed with 1×PBST solution using a plate washer, such that the bound phosphorylated or unphosphorylated substrate remains attached to the wells upon washing.

3. Plate Development

The washed plates were developed by treating the plates with a primary antibody that is specific for the phosphorylated substrate, followed by treatment with a secondary antibody that is specific for the primary antibody, and that is capable of catalyzing a reaction that results in a chemiluminescent readout. The chemiluminescent readout was used to quantify the substrate phosphorylation, and, consequently, to determine $IC_{50}$ values for PLK1 inhibition, and was measured using a luminometer (Perkin Elmer/Wallac plate reader). The plate development protocol is described below.

A mixed antibody solution E was prepared by adding 1 μL of the primary antibody, rabbit p-CHK2(T68) (Rockland, Catalog No. 401280), and 1 μL of the secondary antibody, HRP-goat anti-rabbit IgG (Jackson Immunoresearch Catalog No. 111-035-003) to 10000 μL of 0.1% BSA in 1×PBST buffer.

An ELISA substrate solution F was obtained from Thermo Scientific (Supersignal ELISA Pico Catalog No. 37069) and contained 3,000 μL of solution A (Stable Peroxide Solution, Prod #1859677), 3,000 μL of solution B (Luminol Enhancer Solution, Prod #1859676) and 6,000 μL of water.

After the plates were washed, a mixed antibody solution E was added to each well (100 μL/well) and the plate was incubated for 60 minutes at room temperature. The plate was then washed with 1×PBST buffer solution using a plate washer. Next, an ELISA substrate solution was added to each well (100 μL/well) and chemiluminescence at each well was measured using Perkin Elmer/Wallac plate reader. IC50 values for the tested compounds were then determined based on quantification of chemiluminescence.

4. Results

The $IC_{50}$ data for the tested compounds are reported in Table 1.

Cellular PLK1 Assay

1. Culturing of K562 Cells

Human chronic myelogenous leukemia K562 cells (American Tissue Culture Collection) overexpressing CDC25C, were grown in Growth Medium having the following composition: Iscove Dulbecco's Modified Eagle's Medium ("Iscove DMEM", Mediatech/Cellgro, Cat. #10-013-CV), 10% Fetal Bovine Serum ("FBS", SAFC Biosciences, Cat. #12106-500M), and 1% penicillin/streptomycin ("pen-strep", Mediatech/Cellgro, Cat. #30-002-CI). The cells were plated in 96 well round bottom tissue culture plates (Fisher, Costar* Cell Culture plates, Cat. #07-200-95) at 100,000 cells per 50 μL of Growth Medium per well. Nocodazole (Sigma, Cat. # M1404) was added to the growth media to arrest the cells in the G2 or M phase, at 333 nM concentration. The cells were incubated with nocodazole for 18 hours at 37° C. prior to addition of tested compounds.

2. Treatment of Cells with the Tested Compounds

Solutions of tested compounds in DMSO at different concentrations were prepared using serial dilutions. Each compound was tested at 8 concentration points, 10 μM, 3.3 μM, 1.11 μM, 0.37 μM, 0.12 μM, 0.04 μM, 0.014 μM, 0.005 μM, duplicate replicates.

Two controls were performed: "DMSO alone" control in which nocodazole and DMSO were present but no compounds were added, and "nocodazole alone" control, in which only nocodazole was present, but neither DMSO nor compounds were added.

The solutions of compounds were prepared by diluting 10 mM compound 1:1 in DMSO (5 μL 10 mM compound and 5 μL DMSO), followed by 1:3 serial dilutions of compound in DMSO performed by diluting 3 μL of higher concentration compound solution serially into 6 μL DMSO to give 3-fold dilutions. Next, 3 μL of each compound solution at each concentration was transferred to 750 μL of Growth Medium. In "DMSO alone" control 3 μL of DMSO alone was added to 750 μL of Growth Medium.

After the diluted compounds were mixed well in the Growth Medium, 50 μL of each compound solution in DMSO/Growth Medium was transferred to each well of the 96-plate containing cells in 50 μL of Growth Medium/Nocodazole.

The cells and compounds were incubated for 120 minutes at 37° C., in an atmosphere containing 5% $CO_2$.

3. Fixation and Permeabilization of the Cells

After the cells were incubated with compounds, the cells were spun down at 1,000 rpm for 5 minutes at 4° C. and supernatants were removed by flicking the plates. Cells were then washed with 200 μl of ice cold PBS, spun down again and supernatants removed. Cells were then fixed and permeabilized by addition of 100 μL/well of Fixation and Permeabilization Solution (1× buffer provided in BD Biosciences Cytofix/Cytoperm™ Fixation/Permeabilization kit, Cat. #554714) and incubation for 20 minutes at room temperature. The fixative was then removed by centrifugation (5 minutes at 2,000 rpm), and plates were flicked to remove the fixative and washed twice, each time with 200 μL/well BD Perm/Wash buffer (10× concentrate provided in BD Biosciences Cytofix/Cytoperm™ Fixation/Permeabilization kit, Cat. #554714, 1× buffer prepared by dilution in distilled H2O).

4. Staining

Cells were spun down at 1,000 rpm for 5 minutes at 4° C. Supernatants were removed by flicking the plates. A solution of a primary antibody specific for cdc25cp-Ser198 was prepared by diluting Rabbit cdc25c (Ser198) antibody (Cell Signaling, #9529L) 1:50 in a Fluorescence Activated Cell Sorting ("FACS") Buffer (2% FBS in PBS). The cell pellets were resuspended in 50 μL of the primary antibody solution. 50 μL of FACS buffer was added to unstained controls. Staining was allowed to proceed overnight at room temperature.

The plates were then washed by addition of 200 μL of FACS Buffer to each well, were centrifuged and the supernatant was removed.

Next, 50 μL/well of a secondary antibody anti rabbit PE (R-Phycoerythrin conjugated goat F(ab')2 Anti-Rabbit IgG (Biosource™), Invitrogen, Cat no ALI4407) was added to each cell pellet at 1:1,000 dilution with FACS buffer and was incubated for 1 hour at room temperature.

Plates were washed with 200 μL of FACS buffer, were centrifuged and were resuspended in 80 μL of FACS buffer for analysis.

The plates were analyzed using Automatic Micro-Sampling System (AMS) on the FACSCalibur™ flow cytometer (BD Biosciences), collecting 10,000 cells per well.

5. Results $IC_{50}$ values for the assayed compounds were determined based on the fluorescent readouts obtained in flow cytometric analysis. The results are presented in Table 1.

Cellular Aurora B Assay

Cellular Aurora B assay can be performed separately or concurrently with the PLK1 assay. In one example Aurora B assay was performed concurrently with the PLK1 assay. The cells were grown, treated with the tested compounds and fixed as described above. During staining in addition to cdc25cp-Ser198 primary antibody (for phosphorylated PLK1 substrate) a primary antibody for Aurora B substrate, mouse phospho-histone H3 antibody (Cell Signaling #9706L) was used (1:100 dilution in FACS buffer). The cells were resuspended in 50 μL of diluted primary antibodies solution mixture. After staining and washing as described above, secondary antibodies were added. In addition to anti rabbit PE secondary antibody, an anti mouse APC secondary antibody (Allophycocyanin crosslinked goat anti mouse antibody, Invitrogen, Cat. # M30005) was used (50 μL/well of secondary antibody mixture). The mixture was diluted with FACS buffer and incubated as described above. The plates were processed as described above and were analyzed using the AMS on the FACSCalibur™ flow cytometer (BD Biosciences), collecting 10,000 cells per well.

Although various details have been omitted for clarity's sake, various design alternatives may be implemented. Therefore, the present examples are to be considered as illustrative and not restrictive, and the invention is not to be limited to the details given herein, but may be modified within the scope of the appended claims.

We claim:
1. 6-(2-(2-ethoxy-5-(4-methylpiperazin-1-yl)phenylamino)-5-fluoropyrimidin-4-ylamino)-2H-pyrido[3,2-b][1,4]oxazine-3(4H)-one,

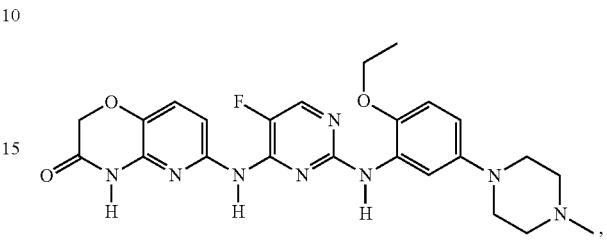

or a solvate, pharmaceutically acceptable salt, or N-oxide thereof.

2. A method of treating a disease or condition, comprising administering to a mammal a therapeutically effective amount of 6-(2-(2-ethoxy-5-(4-methylpiperazin-1-yl)phenylamino)-5-fluoropyrimidin-4-ylamino)-2H-pyrido[3,2-b][1,4]oxazine-3(4H)-one,

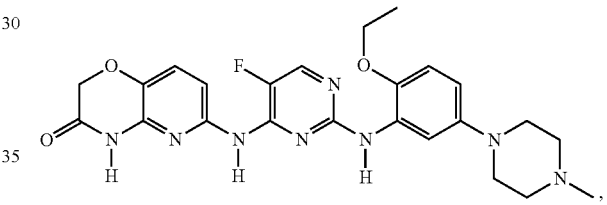

or a solvate, pharmaceutically acceptable salt, or N-oxide thereof, wherein the disease or condition is ductal carcinoma, invasive lobular carcinoma, lobular carcinoma in situ, metastatic breast cancer, basal cell carcinoma, squamous cell carcinoma, malignant melanoma, Kaposi's sarcoma, small cell lung carcinoma, non-small cell lung carcinoma, bronchial adenoma, pleuropulmonary blastoma, malignant mesothelioma, brain stem glioma, hyptothalamic glioma, cerebellar astrocytoma, cerebral astrocytoma, medullablastoma, ependymal tumors, oligodendroglial, meningiomas, neuroectodermal tumor, pineal tumor, prostate cancer, testicular cancer, penile cancer, uterine cancer (endometrial), cervical cancer, ovarian cancer, vaginal cancer, vulval cancer, uterine sarcoma, ovarian germ cell tumor, anal cancer, colon cancer, colorectal cancer, esophageal cancer, gallbladder cancer, stomach (gastric) cancer, pancreatic cancer, pancreatic cancer-Islet cell, rectal cancer, small-intestine cancer, salivary gland cancer, hepatocellular carcinoma, cholangiocarcinoma, mixed hepatocellular cholangiocarcinoma, primary liver cancer, intraocular melanoma, retinoblastoma, rhabdomyosarcoma, laryngeal cancer, hypopharyngeal cancer, nasopharyngeal cancer, oropharyngeal cancers, lip cancer, oral cancer, squamous neck cancer, metastatic paranasal sinus cancer, T cell lymphoma, B cell lymphoma, non-Hodgkin's lymphoma, cutaneous T cell lymphoma, Hodgkin's disease, lymphoma of the central nervous system, acute myeloid leukemia, acute lymphoblastic leukemia, chronic lymphocytic leukemia, chronic myelogenous leukemia, hair cell leukemia, thyroid cancer, thymoma, malignant thymoma, bladder cancer, soft tissue sarcoma, osteosarcoma, malignant fibrous histiocytoma, lymphosarcoma, or rhabdomyosarcoma.

3. A pharmaceutical composition, comprising 6-(2-(2-ethoxy-5-(4-methylpiperazin-1-yl)phenylamino)-5-fluoropyrimidin-4-ylamino)-2H-pyrido[3,2-b][1,4]oxazine-3(4H)-one,

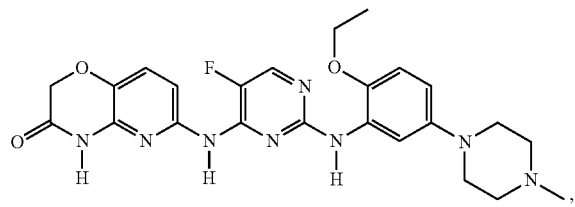 [SMILES: CCOc1ccc(N2CCN(C)CC2)cc1Nc1ncc(F)c(Nc2ccc3c(n2)NC(=O)CO3)n1]

or a solvate, pharmaceutically acceptable salt, or N-oxide thereof.

4. The composition according to claim 3 formulated for topical administration, ocular administration, oral administration, buccal administration, systemic administration, nasal administration, injection administration, transdermal administration, rectal administration, or vaginal administration.

5. The composition according to claim 3 formulated for inhalation or insufflation.

6. The composition according to claim 3 further comprising a suspending agent, a stabilizing agent, a dispersing agent, a buffer, a dextrose solution, a penetrant, a binding agent, a filler, a lubricant, a disintegrant, a wetting agent, a coating agent, a suspending agent, an emulsifying agent, a preservative, a flavoring agent, a coloring agent, a sweetening agent, or combinations thereof.

7. A method for inhibiting an activity of a kinase, comprising contacting the kinase with an effective amount of 6-(2-(2-ethoxy-5-(4-methylpiperazin-1-yl)phenylamino)-5-fluoropyrimidin-4-ylamino)-2H-pyrido[3,2-b][1,4]oxazine-3(4H)-one,

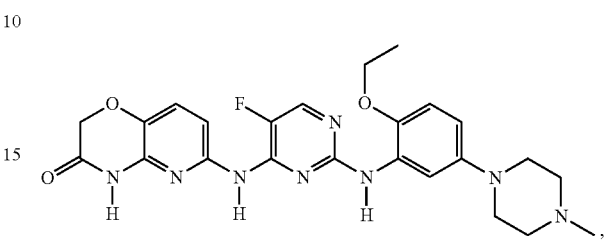

or a solvate, pharmaceutically acceptable salt or N-oxide thereof.

8. The method according to claim 7 wherein the kinase is a PLK.

9. The method according to claim 7 wherein the kinase is selected from PLK1, PLK2, PLK3 or PLK4.

10. The method according to claim 7 wherein the kinase is PLK1.

11. The method according to claim 7 comprising contacting the kinase in vivo.

* * * * *